(12) United States Patent
Askem et al.

(10) Patent No.: US 11,395,870 B2
(45) Date of Patent: Jul. 26, 2022

(54) NEGATIVE PRESSURE WOUND THERAPY APPARATUSES AND METHODS FOR USING THE SAME

(71) Applicant: Smith & Nephew Asia Pacific Pte. Limited, Singapore (SG)

(72) Inventors: Ben Alan Askem, Leeds (GB); Anthony Jonathan Bedford, Cambridge (GB);

(Continued)

(73) Assignee: Smith & Nephew Asia Pacific Pte. Limited, Singapore (SG)

( * ) Notice: Subject to any disclaimer, the term of this patent is extended or adjusted under 35 U.S.C. 154(b) by 341 days.

(21) Appl. No.: 16/486,131

(22) PCT Filed: Feb. 15, 2018

(86) PCT No.: PCT/IB2018/000229
§ 371 (c)(1),
(2) Date: Aug. 14, 2019

(87) PCT Pub. No.: WO2018/150268
PCT Pub. Date: Aug. 23, 2018

(65) Prior Publication Data
US 2019/0358372 A1    Nov. 28, 2019

Related U.S. Application Data

(60) Provisional application No. 62/584,053, filed on Nov. 9, 2017, provisional application No. 62/459,537, filed
(Continued)

(51) Int. Cl.
*A61M 1/00* (2006.01)
*A61F 13/00* (2006.01)

(52) U.S. Cl.
CPC ......... *A61M 1/74* (2021.05); *A61F 13/00068* (2013.01); *A61M 1/0001* (2013.01);
(Continued)

(58) Field of Classification Search
CPC .... A61M 1/0001; A61M 1/0023; A61M 1/74; A61M 1/90; A61M 2205/14;
(Continued)

(56) References Cited

U.S. PATENT DOCUMENTS

D239,019 S    3/1976 Flinn
4,498,850 A   2/1985 Perlov et al.
(Continued)

FOREIGN PATENT DOCUMENTS

DE    102015215165 A1    2/2017
EP    0883430 B1    1/2007
(Continued)

OTHER PUBLICATIONS

Jenkins R.W., et al., "Mechanisms of Resistance to Immune Checkpoint Inhibitors," British Journal of Cancer, Jan. 2, 2018, vol. 118, https://doi.org/10.1038/bjc.2017.434, pp. 9-16.
(Continued)

*Primary Examiner* — Kai H Weng
(74) *Attorney, Agent, or Firm* — Knobbe, Martens, Olson & Bear, LLP

(57) ABSTRACT

Embodiments of negative pressure wound therapy systems, apparatuses, and methods for operating the systems and apparatuses are disclosed. In some embodiments, the apparatus includes a negative pressure source, a connector port, at least one switch, and a controller. The negative pressure source is connected through the connector port to either (i) a wound dressing having a canister configured to store fluid aspirated from the wound or (ii) a wound dressing without a canister between the connector port and the wound dress-
(Continued)

ing. The controller determines, based on a signal received from the at least one switch, whether the canister is positioned in the fluid flow path and adjusts one or more operational parameters of negative pressure wound therapy based on the determination. The switch is activated by the connection of either the canister or canisterless wound dressing to the apparatus.

13 Claims, 79 Drawing Sheets

(72) Inventors: Kevin Bendele, Fort Worth, TX (US); Ali Khishdoost Borazjani, Hull (GB); Nicola Brandolini, Beverley (GB); Ian Charles Culverhouse, Bristol (GB); Otteh Edubio, Hull (GB); James Maxwell Eelbeck, Bristol (GB); Matt Ekman, Hull (GB); Matthew Keith Fordham, Saffron Walden (GB); Philip Gowans, Rawcliffe (GB); Michael James Hayers, Kingston upon Hull (GB); Mark Richard Hesketh, Sandy (GB); James Daniel Homes, Bristol (GB); Allan Kenneth Frazer Grugeon Hunt, Beverley (GB); Mark Edward Jones, St Neots (GB); William Kelbie, Inverness (GB); Reece Knight, Kingston upon Hull (GB); David Mcleod, Bristol (GB); Nisha Mistry, Dubai (AE); Samuel John Mortimer, Kingston upon Hull (GB); Fatoona Mosa, Hull (GB); Matthew Murphy, Dubai (AE); Michael Paton, Royston (GB); Neil Harry Patrick, Hull (GB); Louis della-Porta, Hull (GB); Felix Clarence Quintanar, Hull (GB); Lee Michael Rush, St. Petersburg, FL (US); Carl Dean Saxby, Kingston upon Hull (GB); Hannah Bailey Sidebottom, Lincoln (GB); Daniel Lee Steward, Kingston upon Hull (GB); Catherine Thaddeus, Scunthorpe (GB); Simon Tyson, Singapore (SG); David Ronald Upton, New Hill, NC (US); William Jacob Ward, Apex, NC (US); Nicholas Warrington, Cambridge (GB)

Related U.S. Application Data on Feb. 15, 2017, provisional application No. 62/459,511, filed on Feb. 15, 2017, provisional application No. 62/459,528, filed on Feb. 15, 2017, provisional application No. 62/459,524, filed on Feb. 15, 2017, provisional application No. 62/459,525, filed on Feb. 15, 2017.

(52) U.S. Cl.
CPC .......... *A61M 1/90* (2021.05); *A61M 2205/14* (2013.01); *A61M 2205/3313* (2013.01); *A61M 2205/3317* (2013.01); *A61M 2205/3344* (2013.01); *A61M 2205/3375* (2013.01); *A61M 2205/584* (2013.01)

(58) Field of Classification Search
CPC .. A61M 2205/3313; A61M 2205/3317; A61M 2205/3344; A61M 2205/3375; A61M 2205/584; A61M 2205/587; A61M 2209/086; A61M 2209/088; A61F 13/00068

See application file for complete search history.

(56) References Cited

U.S. PATENT DOCUMENTS

| 4,731,076 | A | 3/1988 | Noon et al. |
|---|---|---|---|
| D357,735 | S | 4/1995 | McPhee |
| 5,514,088 | A | 5/1996 | Zakko |
| 5,712,795 | A | 1/1998 | Layman et al. |
| 6,027,490 | A | 2/2000 | Radford et al. |
| 6,203,291 | B1 | 3/2001 | Stemme et al. |
| 6,232,680 | B1 | 5/2001 | Bae et al. |
| 6,396,407 | B1 | 5/2002 | Kobayashi |
| D475,132 | S | 5/2003 | Randolph |
| 7,004,915 | B2 | 2/2006 | Boynton et al. |
| 7,022,113 | B2 | 4/2006 | Lockwood et al. |
| 7,070,584 | B2 | 7/2006 | Johnson et al. |
| 7,214,202 | B1 | 5/2007 | Vogel et al. |
| D581,042 | S | 11/2008 | Randolph et al. |
| D590,934 | S | 4/2009 | Randolph et al. |
| 7,608,066 | B2 | 10/2009 | Vogel |
| 7,611,500 | B1 | 11/2009 | Lina et al. |
| D625,801 | S | 10/2010 | Pidgeon et al. |
| 7,857,806 | B2 | 12/2010 | Karpowicz et al. |
| D630,313 | S | 1/2011 | Pidgeon et al. |
| D630,725 | S | 1/2011 | Pidgeon et al. |
| 7,927,319 | B2 | 4/2011 | Lawhorn |
| D645,137 | S | 9/2011 | Gonzalez |
| 8,021,348 | B2 | 9/2011 | Risk, Jr. et al. |
| 8,062,272 | B2 | 11/2011 | Weston |
| 8,066,243 | B2 | 11/2011 | Svedman et al. |
| 8,070,735 | B2 | 12/2011 | Koch et al. |
| D654,164 | S | 2/2012 | Cole et al. |
| D660,409 | S | 5/2012 | Taggerty et al. |
| 8,215,929 | B2 | 7/2012 | Shen et al. |
| 8,216,197 | B2 | 7/2012 | Simmons et al. |
| 8,226,620 | B2 | 7/2012 | Giezendanner et al. |
| 8,308,714 | B2 | 11/2012 | Weston et al. |
| 8,317,774 | B2 | 11/2012 | Adahan |
| 8,366,692 | B2 | 2/2013 | Weston et al. |
| 8,409,160 | B2 | 4/2013 | Locke et al. |
| 8,480,641 | B2 | 7/2013 | Jacobs |
| 8,540,688 | B2 | 9/2013 | Eckstein et al. |
| 8,641,693 | B2 | 2/2014 | Locke et al. |
| 8,668,677 | B2 | 3/2014 | Eckstein et al. |
| 8,858,517 | B2 | 10/2014 | Pan et al. |
| 8,905,985 | B2 | 12/2014 | Allen et al. |
| 9,050,398 | B2 | 6/2015 | Armstrong et al. |
| 9,084,845 | B2 | 7/2015 | Adie et al. |
| 9,138,531 | B2 | 9/2015 | Yodfat et al. |
| 9,199,010 | B2 | 12/2015 | Yao et al. |
| D750,222 | S | 2/2016 | Chang |
| D750,235 | S | 2/2016 | Maurice |
| D757,260 | S | 5/2016 | Lombardi, III et al. |
| 9,327,063 | B2 | 5/2016 | Locke et al. |
| 9,333,281 | B2 | 5/2016 | Giezendanner et al. |
| 9,415,199 | B2 | 8/2016 | Tsai |
| 9,427,505 | B2 | 8/2016 | Askem et al. |
| 9,445,948 | B2 | 9/2016 | Smola |
| D773,658 | S | 12/2016 | Bow |
| 9,586,036 | B2 | 3/2017 | Masuda et al. |
| D788,293 | S | 5/2017 | Eckstein et al. |
| D791,939 | S | 7/2017 | Turturro et al. |
| D792,586 | S | 7/2017 | Becker |
| 9,737,649 | B2 | 8/2017 | Begin et al. |
| D797,275 | S | 9/2017 | Evans et al. |
| D802,744 | S | 11/2017 | Bjelovuk et al. |
| 9,901,664 | B2 | 2/2018 | Askem |
| D813,374 | S | 3/2018 | Bjelovuk et al. |
| D814,016 | S | 3/2018 | Bjelovuk et al. |
| 9,923,401 | B2 | 3/2018 | Jung |
| D815,726 | S | 4/2018 | Bjelovuk et al. |
| D815,727 | S | 4/2018 | Bjelovuk et al. |
| D820,980 | S | 6/2018 | Maurice |

(56) References Cited

U.S. PATENT DOCUMENTS

| | | |
|---|---|---|
| 10,124,093 B1 | 11/2018 | Francis et al. |
| 10,155,070 B2 | 12/2018 | Childress et al. |
| D842,460 S | 3/2019 | Gierse et al. |
| D851,759 S | 6/2019 | Jones et al. |
| D852,356 S | 6/2019 | Steele et al. |
| 2002/0013545 A1 | 1/2002 | Soltanpour et al. |
| 2002/0030002 A1 | 3/2002 | Verkaart et al. |
| 2002/0098097 A1 | 7/2002 | Singh |
| 2002/0161317 A1 | 10/2002 | Risk et al. |
| 2004/0068224 A1 | 4/2004 | Couvillon, Jr. et al. |
| 2005/0234485 A1 | 10/2005 | Seegert et al. |
| 2006/0281398 A1 | 12/2006 | Yokomizo et al. |
| 2009/0216205 A1 | 8/2009 | Ryan et al. |
| 2009/0299306 A1 | 12/2009 | Buan |
| 2010/0022990 A1 | 1/2010 | Karpowicz et al. |
| 2010/0155465 A1 | 6/2010 | Mollstam et al. |
| 2010/0244780 A1 | 9/2010 | Turner et al. |
| 2011/0006876 A1 | 1/2011 | Moberg et al. |
| 2011/0060300 A1 | 3/2011 | Weig et al. |
| 2011/0076170 A1 | 3/2011 | Fujisaki et al. |
| 2011/0196291 A1 | 8/2011 | Vischer et al. |
| 2012/0109083 A1 | 5/2012 | Coulthard et al. |
| 2012/0289913 A1 | 11/2012 | Eckstein et al. |
| 2013/0012772 A1 | 1/2013 | Gunday et al. |
| 2013/0025692 A1 | 1/2013 | Heide et al. |
| 2013/0053795 A1 | 2/2013 | Coulthard et al. |
| 2013/0131616 A1 | 5/2013 | Locke |
| 2013/0237937 A1 | 9/2013 | Ramella et al. |
| 2013/0274718 A1 | 10/2013 | Yao et al. |
| 2014/0023533 A1 | 1/2014 | Ishii et al. |
| 2014/0276488 A1 | 9/2014 | Locke et al. |
| 2015/0174320 A1 | 6/2015 | Grant et al. |
| 2015/0231021 A1 | 8/2015 | Smith et al. |
| 2015/0246164 A1 | 9/2015 | Heaton et al. |
| 2015/0320916 A1 | 11/2015 | Croteau et al. |
| 2016/0015872 A1 | 1/2016 | Luckemeyer et al. |
| 2016/0015957 A1* | 1/2016 | Tieck .................. A61J 1/1481 604/533 |
| 2016/0101278 A1 | 4/2016 | Norris et al. |
| 2016/0213843 A1 | 7/2016 | Despa et al. |
| 2016/0250398 A1 | 9/2016 | Barr et al. |
| 2016/0271305 A1 | 9/2016 | Kurihara et al. |
| 2016/0303358 A1 | 10/2016 | Croizat et al. |
| 2017/0189588 A1 | 7/2017 | Croizat et al. |
| 2017/0189666 A1 | 7/2017 | Sealfon et al. |
| 2017/0216501 A1 | 8/2017 | Armstrong et al. |
| 2017/0224975 A1 | 8/2017 | Peer et al. |
| 2017/0296716 A1 | 10/2017 | Middleton et al. |
| 2017/0319758 A1 | 11/2017 | Eddy et al. |
| 2017/0354767 A1 | 12/2017 | Carr et al. |
| 2018/0001000 A1 | 1/2018 | Herwig et al. |
| 2018/0021178 A1 | 1/2018 | Locke et al. |
| 2018/0104391 A1 | 4/2018 | Luxon et al. |
| 2018/0140466 A1 | 5/2018 | Hunt |
| 2018/0250459 A1 | 9/2018 | Kimball et al. |
| 2018/0318476 A1 | 11/2018 | Askem et al. |
| 2019/0192744 A1 | 6/2019 | Greener et al. |
| 2021/0077670 A1 | 3/2021 | Long et al. |

FOREIGN PATENT DOCUMENTS

| | | |
|---|---|---|
| EP | 2 255 837 | 12/2010 |
| EP | 3124059 A1 | 2/2017 |
| EP | 3124060 A1 | 2/2017 |
| FR | 2939320 A1 | 6/2010 |
| GB | 1220857 A | 1/1971 |
| JP | S5647279 U | 4/1981 |
| JP | H01101978 A | 4/1989 |
| JP | H0796029 A | 4/1995 |
| JP | 2007218241 A | 8/2007 |
| JP | 6047279 B2 | 12/2016 |
| WO | WO-9605873 A1 | 2/1996 |
| WO | WO-03081762 A1 | 10/2003 |
| WO | WO-2008033788 A2 | 3/2008 |
| WO | WO-2009071924 A1 | 6/2009 |
| WO | WO-2011075706 A1 | 6/2011 |
| WO | WO-2011094410 A2 | 8/2011 |
| WO | WO-2012004298 A1 | 1/2012 |
| WO | WO-2012100624 A1 | 8/2012 |
| WO | WO-2013015827 A2 | 1/2013 |
| WO | WO-2013064852 A1 | 5/2013 |
| WO | WO-2013078214 A1 | 5/2013 |
| WO | WO-2014115819 A1 | 7/2014 |
| WO | WO 2014/164655 | 10/2014 |
| WO | WO-2015197462 A1 | 12/2015 |
| WO | WO 2016/103035 | 6/2016 |
| WO | WO-2016103031 A1 | 6/2016 |
| WO | WO-2016109048 A1 | 7/2016 |
| WO | WO 2017/027850 | 2/2017 |
| WO | WO-2017044138 A1 | 3/2017 |
| WO | WO-2017062042 A1 | 4/2017 |
| WO | WO-2017160412 A1 | 9/2017 |
| WO | WO-2017197357 A1 | 11/2017 |
| WO | WO-2018009873 A1 | 1/2018 |
| WO | WO-2018009880 A1 | 1/2018 |
| WO | WO-2018036823 A1 | 3/2018 |
| WO | WO-2018041854 A1 | 3/2018 |
| WO | WO-2018150263 A1 | 8/2018 |
| WO | WO-2018150267 A2 | 8/2018 |
| WO | WO-2018150268 A1 | 8/2018 |
| WO | WO-2018167199 A1 | 9/2018 |
| WO | WO-2018195101 A1 | 10/2018 |
| WO | WO-2019063467 A1 | 4/2019 |
| WO | WO-2019129581 A2 | 7/2019 |

OTHER PUBLICATIONS

International Preliminary Reporton Patentability for Application No. PCT/IB2018/000204, dated Aug. 29, 2019, 9 pages.

International Preliminary Reporton Patentability for Application No. PCT/IB2018/000220, dated Aug. 29, 2019, 16 pages.

International Preliminary Report on Patentability for Application No. PCT/IB2018/000229, dated Aug. 29, 2019, 15 pages.

International Search Report and Written Opinion for Application No. PCT/IB2018/000204, dated Jun. 7, 2018, 10 pages.

International Search Report and Written Opinion for Application No. PCT/IB2018/000220, dated Sep. 25, 2018, 22 pages.

Invitation to Pay Additional Fees and Partial Search Report for Application No. PCT/IB2018/000229, dated Jun. 4, 2018, 22 pages.

Invitation to Pay Additional Fees and Partial Search Report for Application No. PCT/IB2018/000220, dated May 30, 2018, 23 pages.

Wikipedia, "Battery Charger," retrieved from https://web.archive.org/web/20181109005000/https://en.wikipedia.org/wiki/Battery_charger, on Nov. 9, 2018, 12 pages.

International Search Report and Written Opinion, re PCT Application No. PCT/IB2018/000229, dated Jul. 30, 2018.

* cited by examiner

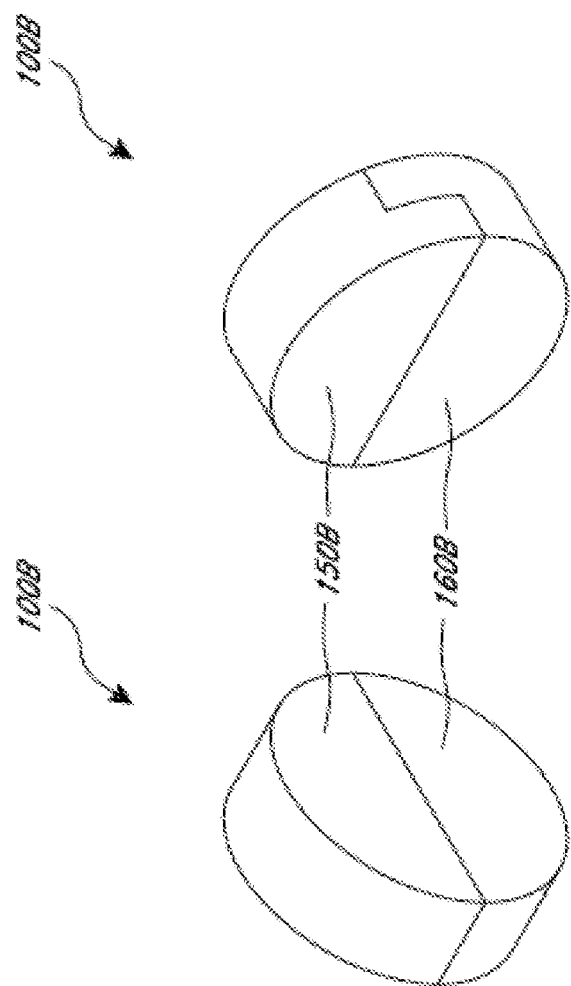
FIG. 9B
FIG. 9C
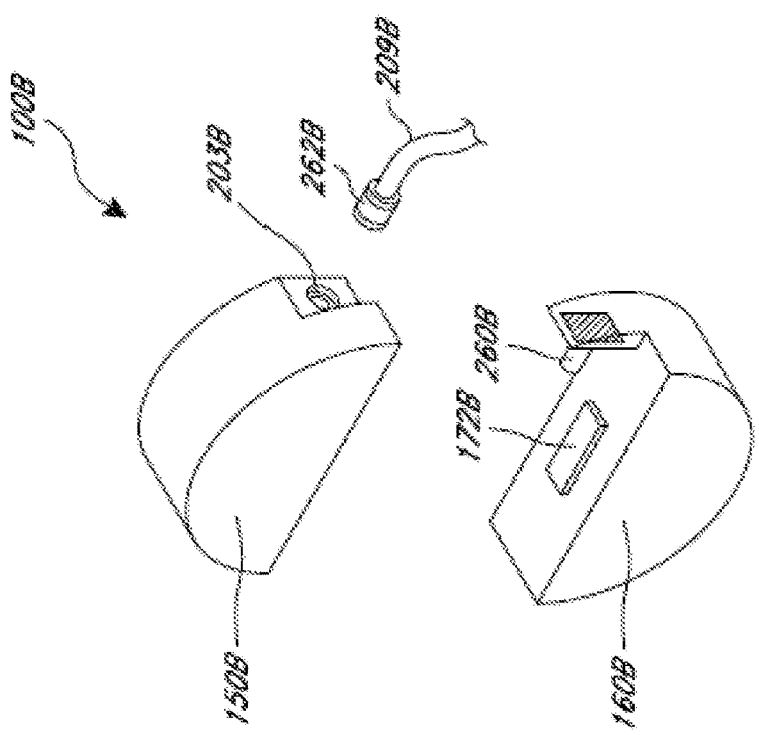
FIG. 9A

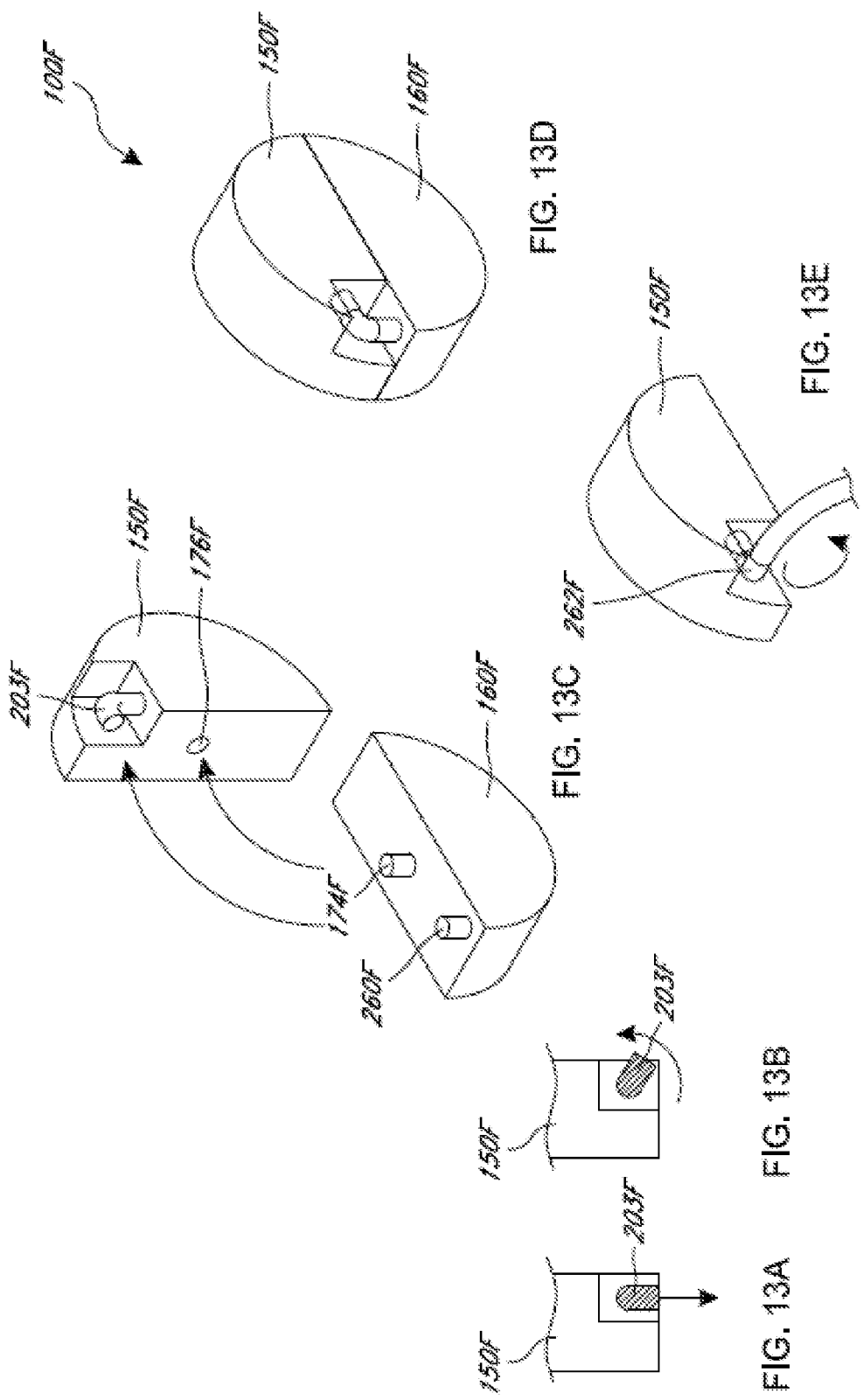

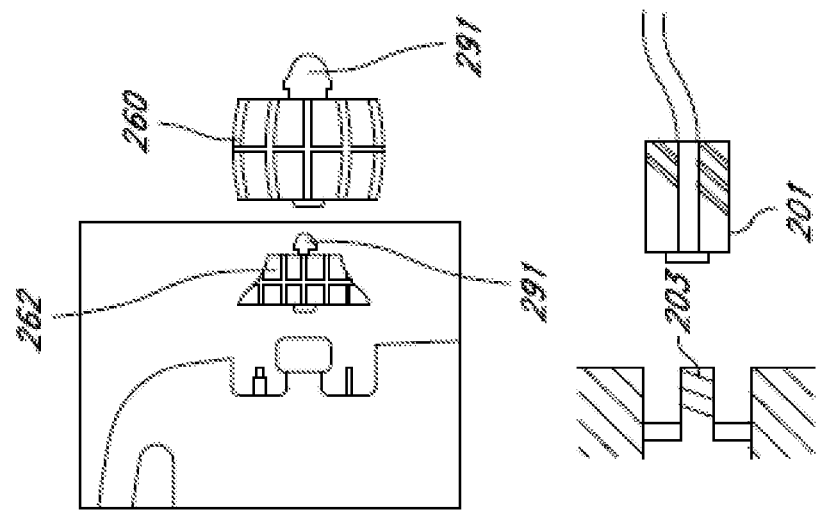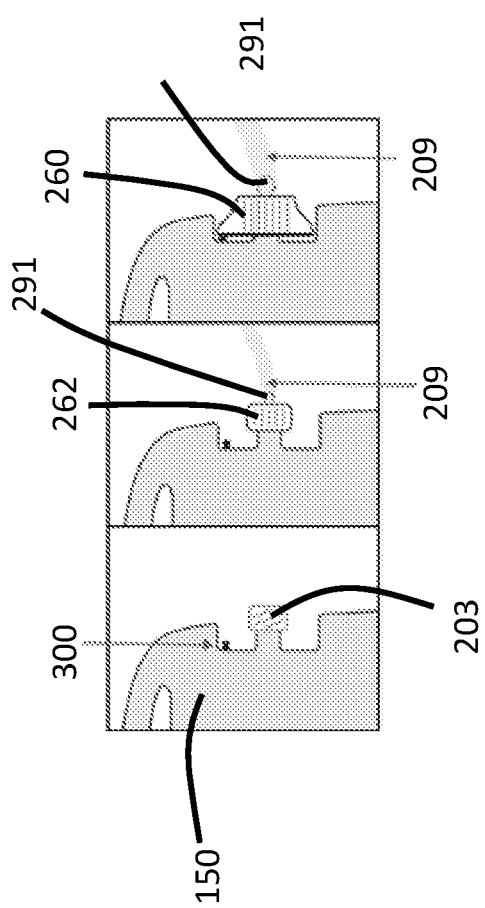
FIG. 20

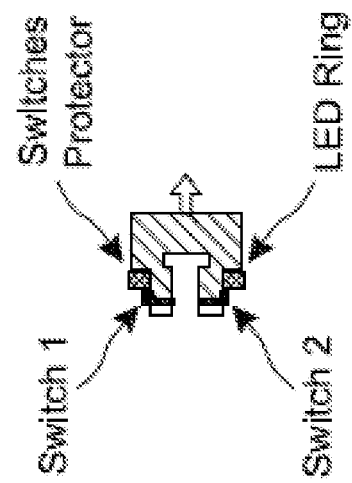
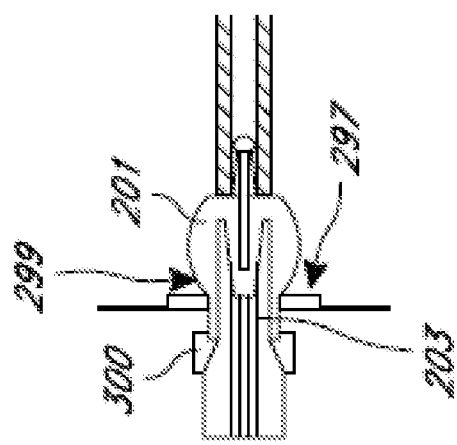
FIG. 22

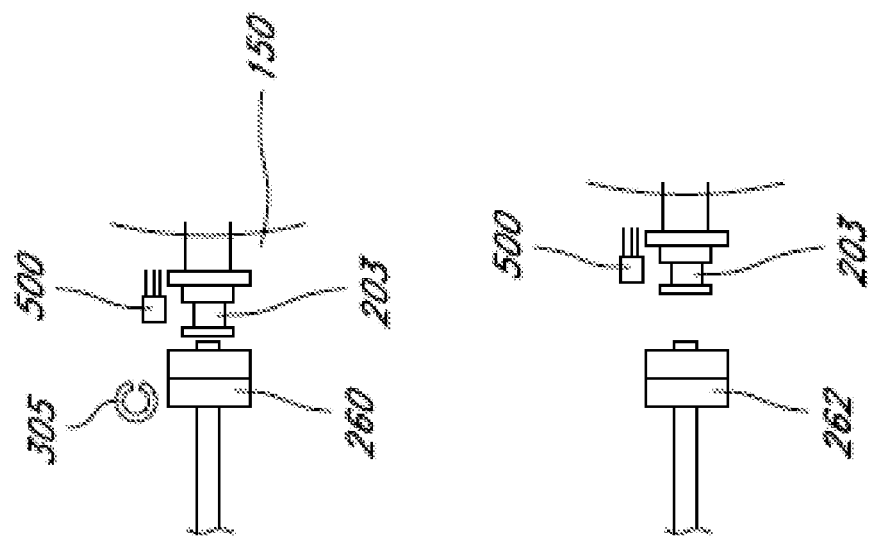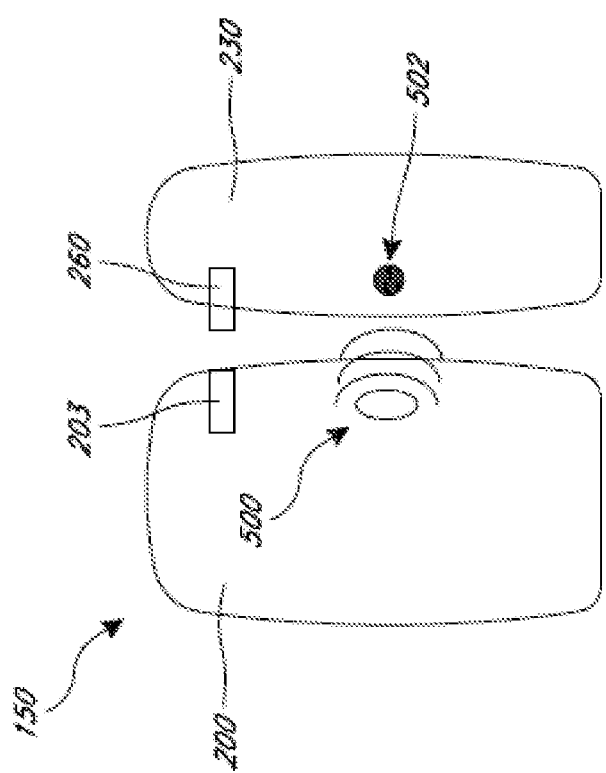
FIG. 24

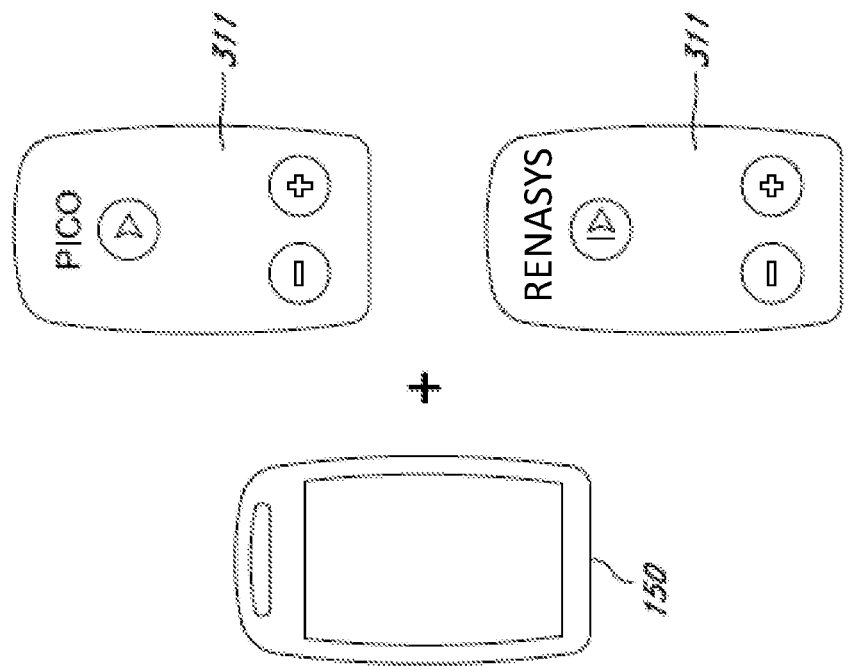
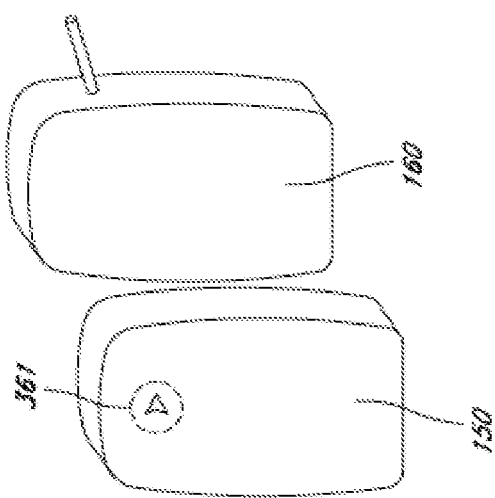
FIG. 25

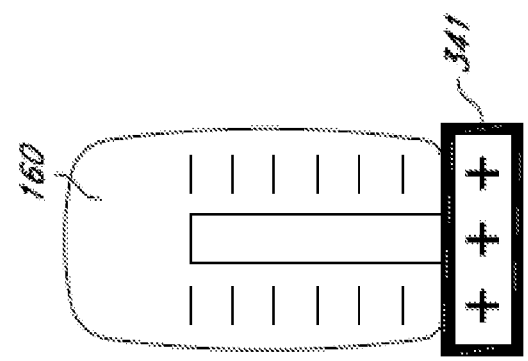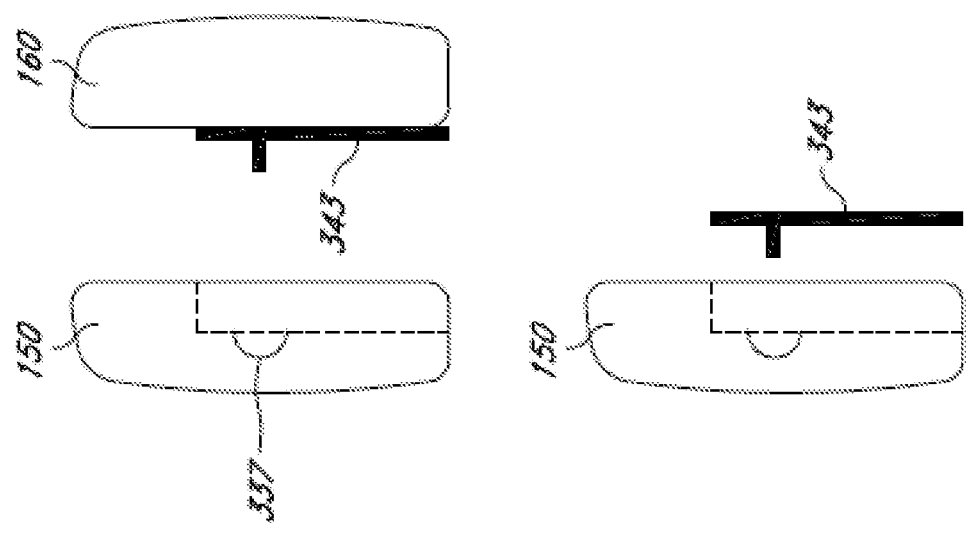
FIG. 34

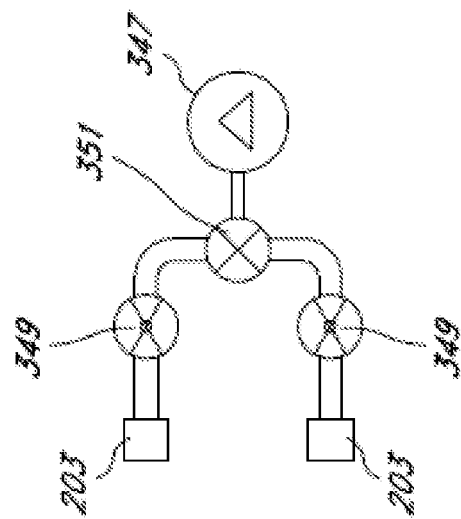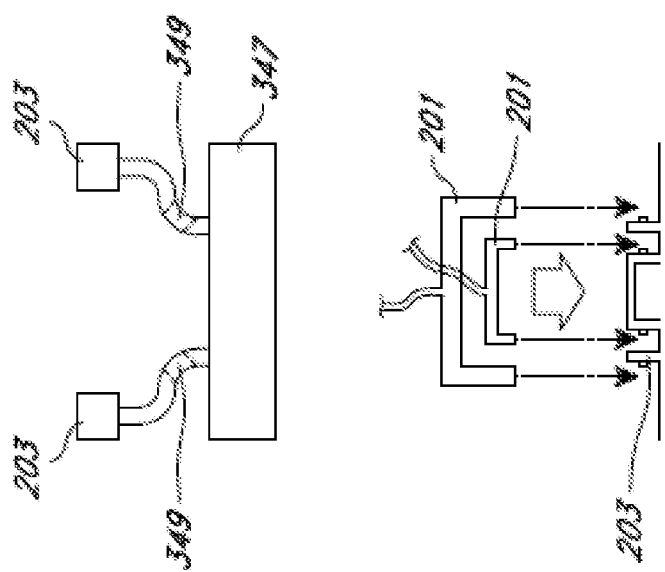
FIG. 36

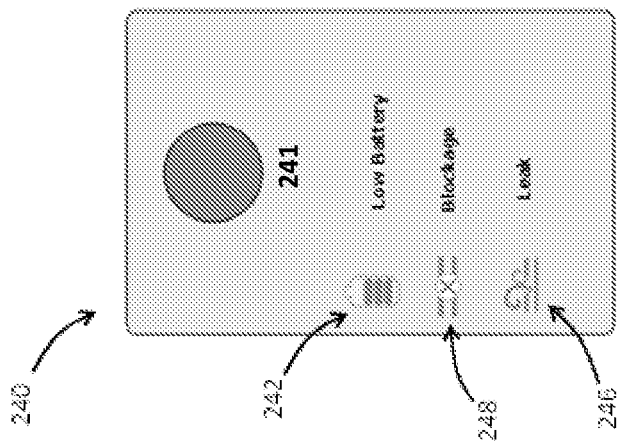
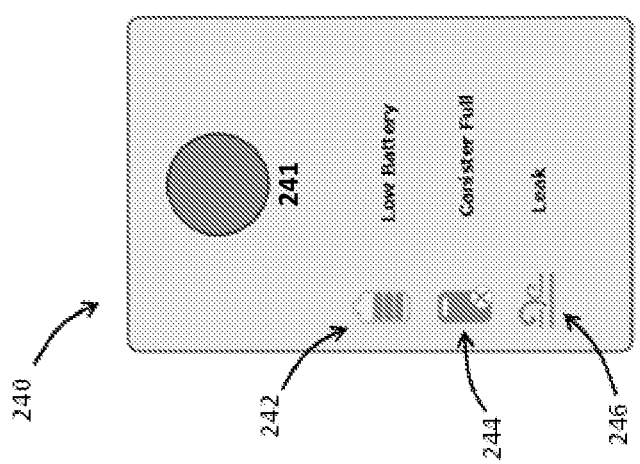
FIG. 38

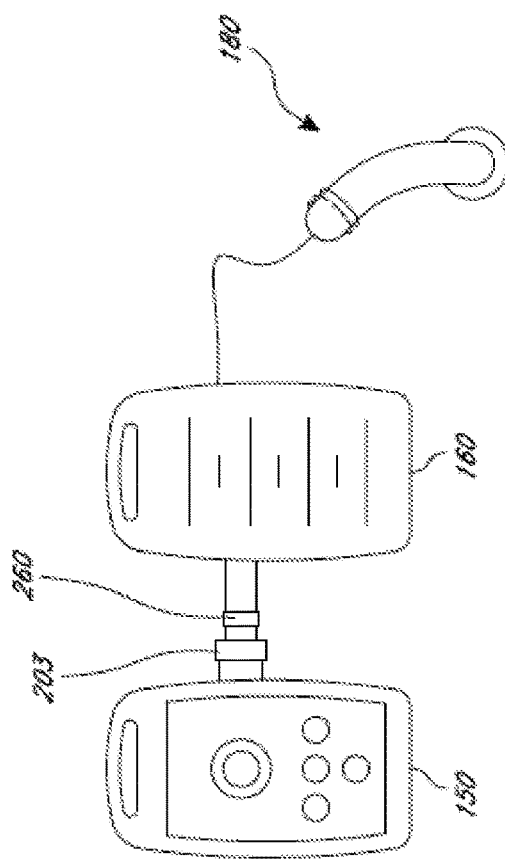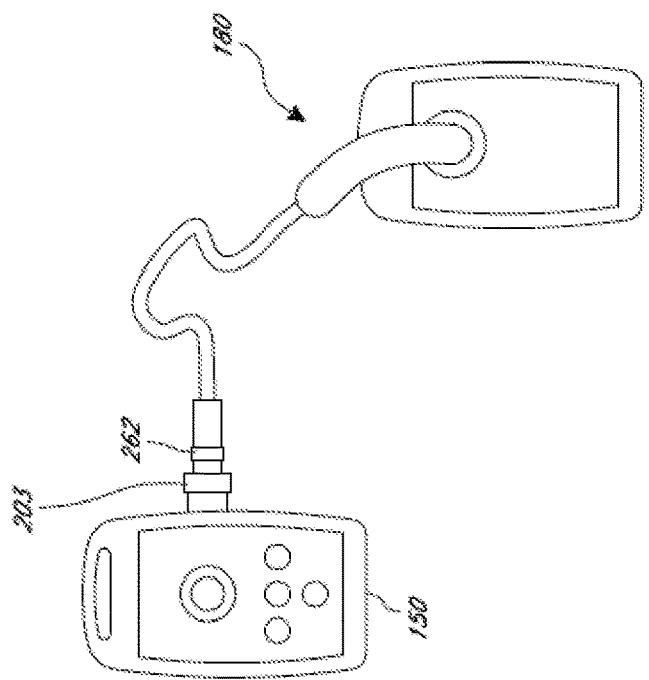
FIG. 43

NEGATIVE PRESSURE WOUND THERAPY APPARATUSES AND METHODS FOR USING THE SAME

CROSS-REFERENCE TO RELATED APPLICATIONS

The present disclosure is a U.S. national stage application of International Patent Application No. PCT/IB2018/000229, filed Feb. 15, 2018, which claims the benefit of U.S. Provisional Application No. 62/459,511, filed Feb. 15, 2017, and entitled "NEGATIVE PRESSURE WOUND THERAPY APPARATUSES AND METHODS FOR USING THE SAME," and to U.S. Provisional Application No. 62/459,524, filed Feb. 15, 2017, and entitled "NEGATIVE PRESSURE WOUND THERAPY APPARATUSES AND METHODS FOR USING THE SAME," and to U.S. Provisional Application No. 62/459,525, filed Feb. 15, 2017, and entitled "NEGATIVE PRESSURE WOUND THERAPY APPARATUSES AND METHODS FOR USING THE SAME," and to U.S. Provisional Application No. 62/459,537, filed Feb. 15, 2017, and entitled "NEGATIVE PRESSURE WOUND THERAPY APPARATUSES AND METHODS FOR USING THE SAME," and to U.S. Provisional Application No. 62/459,528, filed Feb. 15, 2017, and entitled "NEGATIVE PRESSURE WOUND THERAPY APPARATUSES AND METHODS FOR USING THE SAME," and to U.S. Provisional Application No. 62/584,053, filed Nov. 9, 2017, and entitled "NEGATIVE PRESSURE WOUND THERAPY APPARATUSES AND METHODS FOR USING THE SAME," the entirety of each of which applications is hereby incorporated by reference.

BACKGROUND

Embodiments or arrangements disclosed herein relate to methods and apparatuses for dressing and treating a wound with topical negative pressure (TNP) therapy. For example, but without limitation, any embodiments disclosed herein may relate to treating a wound with reduced pressure provided from a pump kit. Although not required, any embodiments of the pump kit can be sterile. As another non-limiting example, any embodiments disclosed herein relate to apparatuses and methods for controlling the operation of a TNP system.

Many different types of wound dressings are known for aiding in the healing process of a human or animal. These different types of wound dressings include many different types of materials and layers, for example, pads such as gauze pads or foam pads. Topical negative pressure ("TNP") therapy, sometimes referred to as vacuum assisted closure, negative pressure wound therapy, or reduced pressure wound therapy, is widely recognized as a beneficial mechanism for improving the healing rate of a wound. Such therapy is applicable to a broad range of wounds such as incisional wounds, open wounds and abdominal wounds or the like.

TNP therapy assists in the closure and healing of wounds by reducing tissue edema; encouraging blood flow; stimulating the formation of granulation tissue; removing excess exudates, and may reduce bacterial load and thus reduce the potential for infection of the wound. Furthermore, TNP therapy permits less outside disturbance of the wound and promotes more rapid healing.

SUMMARY

Embodiments of the present disclosure relate to apparatuses and methods for wound treatment. Some of the wound treatment apparatuses described herein comprise a pump system or assembly for providing negative pressure to a wound site. Wound treatment apparatuses may also comprise wound dressings that may be used in combination with the pump assemblies described herein, and connectors for connecting the wound dressings to the pump assemblies.

In some embodiments, a negative pressure wound therapy apparatus is disclosed. The apparatus includes a negative pressure source, a connector port, at least one switch disposed at the connector port, and a controller. The negative pressure source provides, via a fluid flow path, negative pressure to a wound. The connector port is in fluid communication with an inlet of the negative pressure source and is fluidically connected either (i) to a canister configured to store fluid aspirated from the wound or (ii) to a wound dressing without a canister between the connector port and the wound dressing. The controller determines, based on a signal received from the at least one switch, whether the canister is positioned in the fluid flow path and adjusts one or more operational parameters of negative pressure wound therapy based on the determination.

The apparatus of the preceding paragraph can further include one or more of the following features: The at least one switch can be disposed within a recess of the connector port. The at least one switch can be activated when a canister connector is inserted into the recess and not activated when a dressing connector is inserted into the recess. The at least one switch can include a plurality of switches, and the controller can be further configured to determine that the canister is connected when each of the plurality of switches is activated. The at least one switch can include a plurality of switches, and the controller can be further configured to determine that the canister is connected when at least some of the plurality of switches are activated. The plurality of switches can include first and second switches positioned on opposite walls of the recess. The at least one switch can be a radial switch or a rotational switch. The at least one switch can include a fluid-contacting switch that, when negative pressure is provided by the negative pressure source, at least some fluid flowing through the fluid flow path comes into contact with the fluid-contacting switch. The at least one switch can include an electrical switch. The at least one switch can be positioned in the fluid flow path. The at least one switch can detect a change of a magnetic field generated by a magnet of the canister. The magnet detected by the at least one switch can be substantially spherical. The at least one switch can include a Hall effect sensor. The at least one switch can include at least one of a capacitive sensor, an inductive sensor, an infrared sensor, an ultrasonic sensor, an optical sensor, or a photodetector. The apparatus can further include a user interface configured to indicate at least some operational parameters, and the controller can adjust the user interface based on the determination. The apparatus can further include a canister having a canister connector and a dressing having a dressing connector, the canister connector and the dressing connector being adapted to be attached to the connector port.

In some embodiments, a method for operating a negative pressure wound therapy apparatus is disclosed. The method includes: in response to a canister or a wound dressing without a separate canister being fluidically connected to a connector port of a negative pressure source, determining whether the canister or the wound dressing without a separate canister is connected to the connector port, and adjusting provision of negative pressure from the negative pressure source based on the determination. The method is performed under control of a controller. The step of determining whether the canister or the wound dressing without a separate canister is connected to the connector port includes detecting the activation of at least one switch disposed at the connector port.

The method of the preceding paragraph can further include one or more of the following features: The at least one switch can be disposed within a recess of the connector port. The at least one switch can include first and second switches, and detecting activation of the at least one switch can include detecting activation of the first and second switches. The at least one switch can include a plurality of switches, and detecting activation of the plurality of switches can include detecting activation of at least some of the plurality of switches. The step of determining that the canister is connected to the connector port can include detecting a change of a magnetic field generated by the canister. The method can further include adjusting a user interface configured to provide at least one operational parameter of the apparatus based on the determination.

In some embodiments, a negative pressure wound therapy system is disclosed. The system includes a pump assembly, a canister, and a controller. The pump assembly has a connector port and a switch disposed on the pump assembly. The canister slidably attaches to the pump assembly and has an inlet through which wound exudate can enter the canister. The canister has a canister connector that forms a fluidic seal with the connector port when the canister is attached to the pump assembly. The switch moves between an actuated position and an unactuated position when the canister slides relative to the pump assembly. The controller detects whether the switch is in the actuated or unactuated position. The controller adjusts, based on a detection of the position of the switch, one or more operational parameters of the pump assembly.

The system of the preceding paragraph can further include one or more of the following features: The pump assembly can operate in a canistered operational mode when the switch is in the actuated position and can operate in a canisterless operational mode when the switch is in the unactuated position. When the canister is slidably removed from the pump assembly, the fluidic seal between the canister connector and the connector port can be broken before the switch moves from the actuated position to the unactuated position. When the canister is slidably attached to the pump assembly, the switch can move from the unactuated position to the actuated position before the fluidic seal is formed between the canister connector and the connector port. The canister connector can include a central opening sized to receive at least a portion of the connector port. The pump assembly can include a housing portion that circumferentially surrounds the connector port and extends along a longitudinal axis of the connector port. A gap between the housing portion and the connector port can be sized to receive at least a portion of the canister connector when the canister connector is attached to the connector port. The system can further include a sealing element disposed on an outer surface of the portion of the canister connector. The sealing element can form a seal between the canister connector and the housing portion when the canister is attached to the pump assembly. The switch can be disposed within a recess of the pump assembly. The canister can further include a fin that slides into the recess when the canister is attached to the pump assembly. The fin can have a top surface, and the switch can slide along the top surface when the switch is in the activated position. The system can further include a second switch that can be actuated by the canister connector when the canister connector is fluidically connected to the connector port. The system can further include a third switch that can be actuated by a canisterless connector when the canisterless connector is fluidically connected to the connector port. The third switch can be actuated by the canister connector when the canister connector is fluidically connected to the connector port, and the second switch can be unactuated when a canisterless connector is fluidically connected to the connector port. The second switch can include a magnetic sensor, and the canister can include a magnet. The system can further include a LED ring that can light when the connector port is fluidically connected to a connector. The LED ring can light a first color when the connector port is fluidically connected to a canister connector and can light a second color when the connector port is fluidically connected to a canisterless connector. The one or more operational parameters of the pump assembly can include a magnitude of a negative pressure generated by the pump assembly.

In some embodiments, a negative pressure wound therapy system is disclosed. The system includes a pump assembly, a canister, a switch, and a controller. The pump assembly includes a connector port. The canister fluidically connects with the pump assembly. The canister has an inlet through which wound exudate can enter the canister. The canister has a canister connector that forms a fluidic seal with the connector port. The switch is disposed on the pump assembly and detects whether the canister is fluidically connected with the pump assembly. The controller adjusts, based on a detection of a configuration of the switch, one or more operational parameters of the pump assembly. The system is arranged so that fluidically connecting the canister to the pump assembly changes the configuration of the switch from a first configuration to a second configuration before the fluidic seal is formed between the canister connector and connector port. The system is further arranged so that fluidically disconnecting the canister from the pump assembly changes the configuration of the switch from the second configuration to the first configuration after the fluidic seal is broken between the canister connector and the connector port.

The system of the preceding paragraph can further include the feature that the switch changes from the first configuration to the second configuration by slidably connecting the canister to the pump assembly.

In some embodiments, a negative pressure wound therapy system is disclosed. The system includes a pump assembly having a negative pressure source. The pump assembly includes a canister connector port and a canisterless connector port disposed on the pump assembly. The canister connector port is fluidically connected to the negative pressure source by a first flow path. The canisterless connector port is fluidically connected to the negative pressure source by a second flow path. The pump assembly includes a detector within the pump assembly. The detector detects at least one of a canister connector being fluidically attached to the canister connector port or a canisterless connector being fluidically attached to the canisterless connector port.

The system of the preceding paragraph can further include one or more of the following features: The pump assembly can further include a controller that, based on the detection by the detector, adjusts one or more operational parameters of the pump assembly. When the canister is connected to the canister connector port, a portion of the canister can block the canisterless connector port and thereby prevent the canisterless connector from being attached to the canisterless connector port. The canister connector can fluidically attach to the canister connector port by a rotation of the canister connector about the canisterless connector port. Fluidically attaching the canister connector to the canister connector port can block at least a portion of the second flow path. The first flow path and the second flow path can pass through a manifold. The canister connector port can have a shape that is different from a shape of the canisterless connector port, thereby preventing a canisterless connector from being inadvertently attached to the canister connector port. The system can include a cover that is movable between a first position and a second position. The canister connector port can be blocked from being attached to the canister connector when the cover is in a first position. The canister connector port can be unblocked from being attached to the canister connector when the cover is in the second position. The cover can move from the first position to the second position when a prong on the canister engages a latch on the pump assembly. The cover can be sized to block one but not both of the canister connector port and the canisterless connector port, and the cover can be movable between a first position and a second position, wherein the cover blocks the canister connector port when the cover is in the first position, and wherein the cover blocks the canisterless connector port when the cover is in the second position. The cover can slide between the first and second positions. At least a portion of the cover can pivot away from the pump assembly to allow the canister connector to be attached to the canister connector port. The system can further include a switch that is actuated by the cover, the detector being adapted to detect whether the switch is actuated by the cover.

In some embodiments, a negative pressure wound therapy system is disclosed. The system includes a pump assembly, a connector port, and a detector. The pump assembly includes a negative pressure source and a pressure sensor. The connector port is disposed on the pump assembly. The detector is disposed at or near the connector port and detects whether the connector port is fluidically attached to a canister connector or a canisterless connector based on a change to an electrical circuit, the change being caused by an attachment of the canister connector or the canisterless connector to the connector port.

The system of the preceding paragraph can further include one or more of the following features: The electrical circuit can be closed by a conductor disposed on one but not on the other of the canister connector and the canisterless connector, the electrical circuit remaining open when the other of the canister connector and the canisterless connector is fluidically connected to the connector port. The detector can include a sensor that detects a property of a connector connected to the connector port, the property of the connector being selected from the group consisting of a color, an electrical resistance, and a presence of a magnet.

In some embodiments, a negative pressure wound therapy system is disclosed. The system includes a pump assembly, a connector port, and a detector. The pump assembly includes a negative pressure source and a pressure sensor. The connector port is disposed on the pump assembly. The detector detects whether a connector attached to the connector port is a canister connector or a canisterless connector based on a deformation of the connector in response to a pressure generated by the negative pressure source.

The system of the preceding paragraph can further include one or more of the following features: The connector can include a check valve. The connector can be fluidically connected to a canister having a flexible membrane. The connector can include a mechanical flap.

In some embodiments, a negative pressure wound therapy apparatus is disclosed. The apparatus includes a negative pressure source, a detector, and a controller. The negative pressure source provides, via a fluid flow path, negative pressure to a wound covered by a wound dressing. The detector detects if a canister is positioned in the fluid flow path between the negative pressure source and the wound. The controller is coupled to the detector and controls, based on a first indication from the detector that the canister is positioned in the fluid flow path, the negative pressure source to provide negative pressure to the wound according to a first mode of operation, wherein a negative pressure level provided by the negative pressure source is adjustable by a user in the first mode of operation. Based on a second indication from the detector that the canister is not positioned in the fluid flow path, the controller controls the negative pressure source to provide negative pressure to the wound according to a second mode of operation different from the first mode of operation, wherein the negative pressure level provided by the negative pressure source is not adjustable by the user in the second mode of operation.

The apparatus of the preceding paragraph can further include one or more of the following features: The apparatus can include a pressure sensor that detects a pressure level in the fluid flow path. The controller can be further adapted to detect at least one of a blockage or leakage in the fluid flow path based at least in part on the pressure level detected by the pressure sensor, the detection being performed differently in the first and second modes of operation. The controller can, without interruption of the provision of negative pressure to the wound, switch from the first mode of operation to the second mode of operation in response to the second indication from the detector and switch from the second mode of operation to the first mode of operation in response to the first indication from the detector. The apparatus can further include a housing enclosing the negative pressure source, the housing having a recess. The detector can include an optical detector positioned in the recess, the optical detector can include a light source that emits light and a light detector that detects emitted light. The canister can include a protrusion that at least partially fits within the recess when the canister is positioned in the fluid flow path. The optical detector can be adapted to detect presence of the canister based on detection, by the light detector, of occlusion by the protrusion of the canister of the emitted light. The optical detector can be adapted to detect improper positioning of the canister based on a partial occlusion of the emitted light and proper positioning of the canister based on a substantially complete occlusion of the emitted light. The canister can include an indicator that provides information about one or more characteristics of the canister. The detector can be adapted to detect the indicator and provide information about the one or more characteristics of the canister to the controller. The controller can operate the negative pressure source based on the one or more characteristics of the canister. The canister can include a housing and a magnet embedded in the housing, and the detector can include a magnetic field detector that can detect presence of the magnet. The magnet can be spherical. The detector can include at least one of: a proximity detector, an optical detector, an RFID detector, or a bar code detector.

In some embodiments, a method of operating a negative pressure wound therapy apparatus having a negative pressure source is disclosed. The method includes detecting if a canister is positioned in a fluid flow path fluidically connecting the negative pressure source to a wound dressing. The method further includes, based on a first indication that the canister is positioned in the fluid flow path, providing negative pressure from the negative pressure source according to a first mode of operation and adjusting a negative pressure level. The method further includes, based on a second indication that the canister is not positioned in the fluid flow path, providing negative pressure from the negative pressure source according to a second mode of operation different from the first mode of operation and preventing adjustment of the negative pressure level. The method is performed under control of a controller.

The method of the preceding paragraph can further include one or more of the following features: monitoring a pressure level in the fluid flow path and detecting at least one of a blockage or leakage in the fluid flow path based at least in part on the pressure level in the fluid flow path, the detection being performed differently in the first and second modes of operation. The method can further include, without interruption of the provision of negative pressure, switching from the first mode of operation to the second mode of operation in response to the second indication and switching from the second mode of operation to the first mode of operation in response to the first indication. The method can further include detecting an improper positioning of the canister in the fluid flow path. The method can further include detecting if the canister is present in the fluid flow path by detecting based on at least one of: proximity detection, optical detection, RFID detection, or bar code detection.

In some embodiments, a negative pressure wound therapy apparatus is disclosed. The apparatus includes a pump assembly, a mode switch, and a controller. The pump assembly provides, via a fluid flow path, negative pressure to a wound covered by a wound dressing. The mode switch indicates whether a canister is positioned in the fluid flow path between the pump assembly and the wound. The controller is coupled to the mode switch. The controller detects an activation state of the mode switch, wherein if the mode switch indicates the presence of a canister in the fluid flow path between the pump assembly and the wound, the controller operates in a canister mode, and if the mode switch does not indicate the presence of a canister in the fluid flow path between the pump assembly and the wound, the controller operates in a canisterless mode. The controller is further adapted to activate the pump assembly to initiate an initial pump down based on operational parameters determined based on the activation state of the mode switch. The controller is further adapted to evaluate a pass condition based on the activation state of the mode switch. The controller is further adapted to operate the pump assembly to initiate a maintenance mode when the pass condition is met. The controller is further adapted such that during the initial pump down and before initiating maintenance mode, if a change in the activation state of the mode switch is detected, the pump assembly is deactivated and cannot be re-activated until a power cycling of the pump assembly occurs.

The apparatus of the preceding paragraph can further include one or more of the following features: The controller can disable the mode switch after the pump assembly initiates the maintenance mode. In the canisterless mode of operation, after the pump assembly initiates the maintenance mode, the controller can disable the mode switch such that the mode switch cannot be enabled until a power cycling of the pump assembly occurs. If a leak is detected, the controller can activate a leak alert and deactivate the pump assembly such that the pump assembly cannot be re-activated until a power cycling of the pump assembly occurs. After the pump assembly initiates the maintenance mode, if a change in the activation state of the mode switch is detected, the controller can activate a leak alert. After the pump assembly initiates the maintenance mode, if a change in the activation state of the mode switch is detected, the controller can deactivate the pump assembly such that the pump assembly cannot be re-activated until a power cycling of the pump assembly occurs. During the initial pump down and before initiating maintenance mode, if a change in the activation state of the mode switch is detected, the controller can activate a leak alert. During the initial pump down and before initiating maintenance mode, if a change in the activation state of the mode switch is detected, the controller can deactivate the pump assembly such that the pump assembly cannot be re-activated until a power cycling of the pump assembly occurs. The pump assembly can include an on/off switch to be operated by a user to perform power cycling. The pump assembly can include one or more buttons configured to activate and deactivate the pump assembly and/or to select desired negative pressure settings. The apparatus can allow the desired negative pressure settings to be selectable by a user only in a canister mode of operation.

In some embodiments, a negative pressure wound therapy system is disclosed. The system includes a pump assembly, a canister, and a strap anchor. The pump assembly includes a connector port. The canister has an internal volume and is configured to be slidably connected to the pump assembly. The canister includes a canister connector that provides a flow path to the internal volume of the canister. The strap anchor is configured for connecting a strap to the wound therapy system. The strap anchor is arranged so that the connector port is superior to at least 80% of the internal volume of the canister when the wound therapy system is suspended from a strap connected to the strap anchor.

The system of the preceding paragraph can further include one or more of the following features: The canister connector receives the connector port into an internal lumen of the canister connector to establish a flow path between the pump assembly and the internal volume of the canister. The strap anchor is disposed on the pump assembly. The pump seats onto a recessed bed of the canister when the connector port is fluidically connected to the canister port. The negative pressure wound therapy system has a substantially disc-shaped form when the connector port is fluidically connected to the canister connector. The system includes a stop filter. The stop filter is disposed between the connector port and the canister connector. The canister further comprises a canister seam surface that contacts a pump seam surface when the connector port is fluidically connected to the canister connector. The canister seam surface has a horizontal portion and a ramped portion. The ramped portion is inclined toward the pump assembly relative to the horizontal portion by a canister angle. The connector port is disposed within the ramped portion of the canister seam surface. The canister angle is between 27 degrees and 33 degrees.

In some embodiments, a negative pressure wound therapy system is disclosed. The system includes a pump assembly and a canister. The pump assembly includes a connector port. The canister has an internal volume and is configured to be slidably connected to the pump assembly such that the connector port and the canister connector are fluidically coupled to one another to form a flow path between the pump assembly and the internal volume of the canister. The negative pressure wound therapy system has a substantially disc-shaped form. The canister has a base diametrically opposed to the pump assembly. The base truncates the substantially disc-shaped form of the negative pressure wound therapy system. The connector port is positioned superior to at least 80% of the internal volume of the canister when the wound therapy system is supported by the base.

The system of the preceding paragraph can further include one or more of the following features: The canister connector receives the connector port into an internal lumen of the canister connector to establish a flow path between the pump assembly and the internal volume of the canister. The base truncates the disc-shaped form of the negative pressure wound therapy system by a span characterized by a base angle that is between 45 degrees and 90 degrees. In some embodiments, the base angle is between 63 degrees and 77 degrees. The negative pressure wound therapy system further includes a stop filter. The stop filter is disposed between the connector port and the canister connector. The canister further comprises a canister seam surface that contacts a pump seam surface when the connector port is fluidically connected to the canister connector. The canister seam surface has a horizontal portion and a ramped portion. The ramped portion is inclined toward the pump assembly relative to the horizontal portion by a canister angle. The connector port is disposed within the ramped portion of the canister seam surface. The canister angle is between 27 degrees and 33 degrees.

In some embodiments, a negative pressure apparatus is disclosed. The apparatus includes a pump assembly, a canister, and a filter. The pump assembly includes an attachment member for connecting a strap. The attachment member is positioned on a first side of the pump assembly. The canister is configured to be slidably connected to the pump assembly. The canister comprises a flat bottom surface and a top surface configured to slidably engage with a bottom surface of the pump assembly. The top surface of the canister is configured to slidably engage with the bottom surface of the pump assembly by sliding the canister relatively from the first side of the pump assembly toward a second side of the pump assembly opposite the first side until the canister reaches a stop. After the pump assembly and canister are connected, the canister has a first side aligned with the first side of the pump assembly and a second side aligned with the second side of the pump assembly. The top surface of the canister is configured to slidably disengage from the bottom surface of the pump assembly by sliding the canister relatively from the second side of the pump assembly toward the first side of the pump assembly. The filter is positioned within the canister at or near the top surface of the canister and at or near the first side of the canister, such that when the pump assembly and canister are connected together, if the pump assembly and canister are either hanging from the strap or the flat bottom surface of the canister is positioned on a support surface, the filter is located at or near an upper end of the canister with respect to a direction of gravity.

The apparatus of the preceding paragraph can further include one or more of the following features: The top surface of the canister has a ramped portion and a horizontal portion. The horizontal portion is substantially parallel to the bottom surface of the canister. The ramped portion is inclined relative to the horizontal portion by a canister angle. The canister angle is between 27 degrees and 33 degrees. The pump assembly comprises a top surface opposite the bottom surface of the pump assembly. The bottom surface includes an inclined portion and a base portion. The inclined portion is angled toward the top surface relative to the base portion. The inclined portion is angled toward the top surface relative to the base portion by an angle between 27 degrees and 33 degrees. The pump assembly comprises a connector port disposed in an inclined portion of the bottom surface of the pump assembly. The canister has a canister connector disposed in a ramped portion of the top surface of the canister. When the canister is connected to the pump assembly and the pump assembly is suspended from the attachment member, the top surface of the canister has a ramped portion that is supported by an inclined portion of the bottom surface of the pump assembly.

In some embodiments, a negative pressure wound therapy apparatus is disclosed. The apparatus includes a negative pressure source and a connector port. The negative pressure source is configured to provide, via a fluid flow path, negative pressure to a wound. The connector port is in fluid communication with an inlet of the negative pressure source. The connector port is configured to be fluidically connected either to a canister configured to store fluid aspirated from the wound or to a wound dressing without a canister between the connector port and the wound dressing. The connector port includes a first sealing surface spaced apart from a second sealing surface. The first sealing surface is adapted to form a fluidic seal with a canister connector of the canister. The second sealing surface is adapted to form a fluidic seal with a canisterless connector of the wound dressing.

The apparatus of the preceding paragraph can further include one or more of the following features: The first sealing surface is disposed radially outward of the second sealing surface. The second sealing surface includes a luer lock fitting. The second sealing surface includes a tapered shaft adapted to form an interference fit with an internal surface of the canisterless connector. The first sealing surface includes a base portion sized to fit inside an opening of the canister connector. The second sealing surface is circumferentially surrounded by the canister connector when the first sealing surface forms a fluidic seal with the canister connector. The first sealing surface remains an uncovered outer surface of the pump assembly when the second sealing surface forms a fluidic seal with the canisterless connector. The first sealing surface includes an O-ring. The second sealing includes a tapered surface having a Morse taper.

Any of the features, components, or details of any of the arrangements or embodiments disclosed in this application, including without limitation any of the pump embodiments and any of the negative pressure wound therapy embodiments disclosed below, are interchangeably combinable with any other features, components, or details of any of the arrangements or embodiments disclosed herein to form new arrangements and embodiments.

BRIEF DESCRIPTION OF THE DRAWINGS

Embodiments of the present disclosure will now be described hereinafter, by way of example only, with reference to the accompanying drawings in which:

FIG. 9A shows an embodiment of the TNP system that has a disc-shaped form when the canister is attached to the pump assembly.

FIG. 9B is a rear perspective view of the TNP system of FIG. 9A.

FIG. 9C is a front perspective view of the TNP system of FIG. 9A.

FIGS. 13A-E show an embodiment of a TNP system with a pump assembly that includes a rotatable connector port.

FIG. 20 illustrates connector switch embodiments that include mechanical switches.

FIG. 22 illustrates connector switch embodiments that include an LED indicator ring that lights when a sealing connection has been made.

FIG. 24 illustrates connector switch embodiments that include a magnetic sensor.

FIG. 25 illustrates connector switch embodiments that include an RFID reader

FIG. 34 illustrates a TNP system having a battery cover that signals whether a canister connector or a canisterless connector is connected to the pump assembly.

FIG. 36 illustrates a TNP system having two connector ports connected to a manifold.

FIG. 38 illustrates an embodiment of a user interface of the TNP system.

FIG. 43 illustrates an embodiment of a TNP system that has a canister connector with a bore size that is larger than that of a canisterless connector.

DETAILED DESCRIPTION

Overview

Embodiments disclosed herein relate to systems and methods of treating a wound with reduced pressure. As is used herein, reduced or negative pressure levels, such as –X mmHg, represent pressure levels relative to normal ambient atmospheric pressure, which can correspond to 760 mmHg (or 1 atm, 2993 inHg, 101.325 kPa, 14.696 psi, etc.). Accordingly, a negative pressure value of –X mmHg reflects absolute pressure that is X mmHg below, for example, 760 mmHg or, in other words, an absolute pressure of (760–X) mmHg. In addition, negative pressure that is "less" or "smaller" than X mmHg corresponds to pressure that is closer to atmospheric pressure (e.g., –40 mmHg is less than –60 mmHg). Negative pressure that is "more" or "greater" than –X mmHg corresponds to pressure that is farther from atmospheric pressure (e.g., –80 mmHg is more than –60 mmHg). In some embodiments, local ambient atmospheric pressure is used as a reference point, and such local atmospheric pressure may not necessarily be, for example, 760 mmHg.

Embodiments of the present disclosure are generally applicable to use in topical negative pressure (TNP) or reduced pressure therapy systems. Briefly, negative pressure wound therapy assists in the closure and healing of many forms of "hard to heal" wounds by reducing tissue edema, encouraging blood flow and granular tissue formation, or removing excess exudate and can reduce bacterial load (and thus infection risk). In addition, the therapy allows for less disturbance of a wound leading to more rapid healing. TNP therapy systems can also assist in the healing of surgically closed wounds by removing fluid. In some embodiments, TNP therapy helps to stabilize the tissue in the apposed position of closure. A further beneficial use of TNP therapy can be found in grafts and flaps where removal of excess fluid is important and close proximity of the graft to tissue is required in order to ensure tissue viability.

Negative Pressure System

Figure 1:
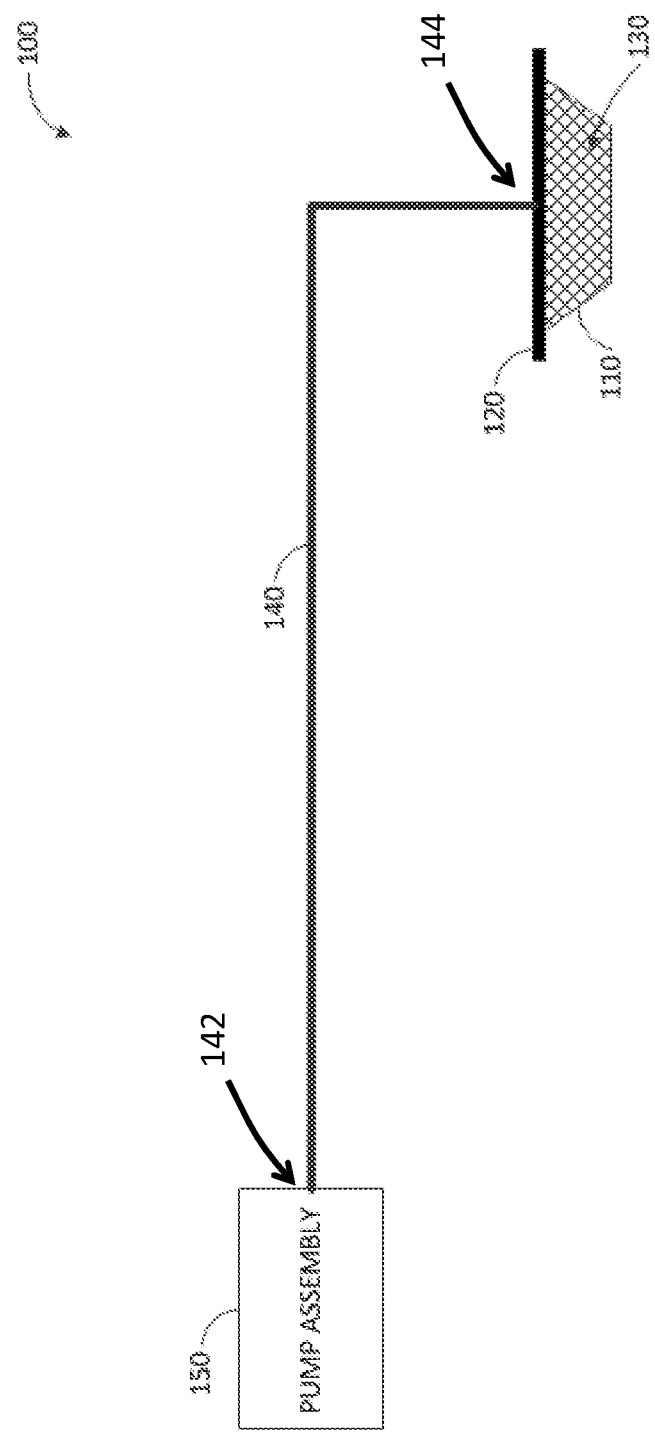
FIG. 1 illustrates a reduced pressure wound therapy system including a pump assembly according to some embodiments.

FIG. 1 illustrates an embodiment of a negative or reduced pressure wound treatment (or TNP) system 100 comprising a wound filler 130 placed inside a wound cavity 110, the wound cavity 110 sealed by a wound cover 120. In some embodiments, one or more of the wound filler 130, the wound cover 120, or any other component, such as a contact layer (not shown), make up a wound dressing. The system 100 includes a negative pressure wound therapy apparatus or a pump assembly 150 configured to provide reduced pressure to the wound. For example, a conduit 140 having at least one lumen can provide a fluid flow path between the pump assembly 150 and the wound. The conduit 140 can have a pump end 142 that is fluidically connected to the pump assembly 150 and a wound end 144 that is inserted under or through the wound cover 120. The conduit 140 can communicate a negative pressure at the pump end 142 to the wound end 144.

Figure 2B:
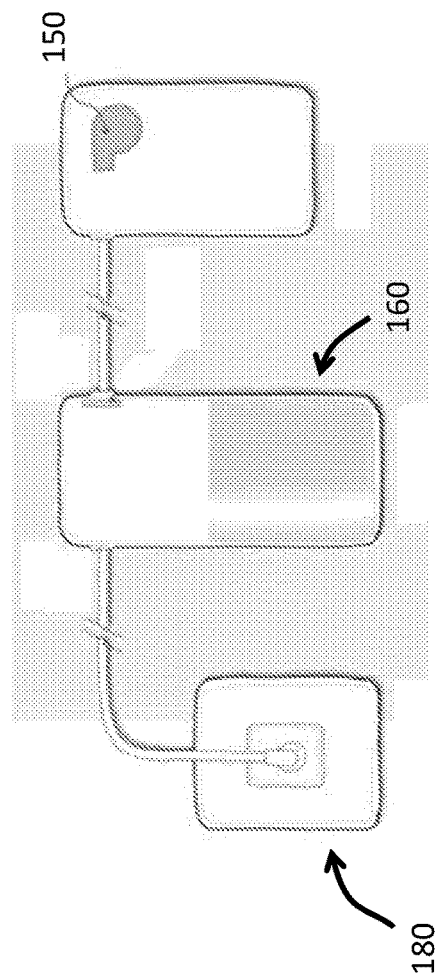
FIG. 2B illustrates a reduced pressure wound therapy system operating in a canister mode of operation.
Figure 2A:
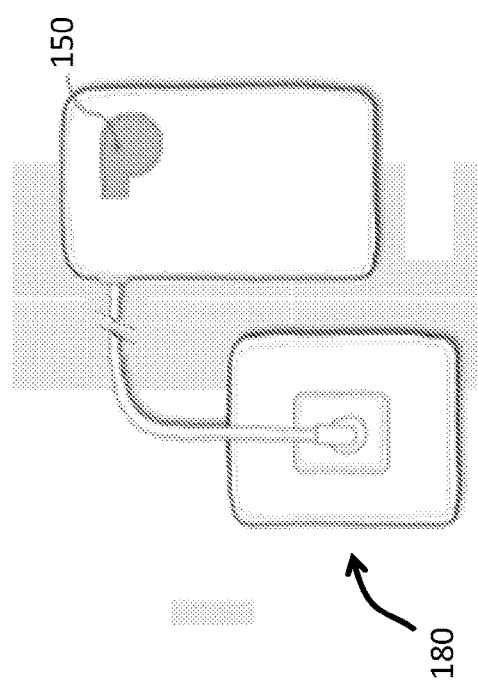
FIG. 2A illustrates a reduced pressure wound therapy system operating in a canisterless mode of operation.

FIGS. 2A-2B illustrate that the reduced pressure wound therapy system can be configured to operate with and without a canister (e.g., canister and canisterless modes). FIG. 2A shows an embodiment of the TNP system 100 that has a wound dressing 180 connected directly to the pump assembly 150 (e.g., canisterless mode). FIG. 2B shows an embodiment of the TNP system 100 that has a canister 160 interposed between a wound dressing 180 and the pump assembly 150 (e.g., canister mode). At the beginning of the application of negative pressure wound therapy to a wound when the wound is in the early stages of the healing process and exudes a significant volume of exudate, the reduced pressure wound therapy system may operate with a canister. In this mode of operation, the negative pressure wound therapy system may operate with a foam or gauze RENASYS™ dressing sold by Smith & Nephew or any other suitable dressing. Operation of the reduced pressure wound therapy system with a canister may sometimes be referred to herein as "RENASYS™", "RENASYS™-mode", or derivatives thereof. As the wound is progressing through the healing process and is starting to exude a smaller volume of exudate, the canister may be removed and the negative pressure wound therapy system may operate with an absorbent dressing, such as the PICO™ dressing sold by Smith & Nephew or any other suitable dressing that retains the wound exudate within the dressing. Further details of absorbent dressings such as the PICO™ dressing are found in U.S. Pat. No. 9,061,095, filed on Apr. 21, 2011, and incorporated in its entirety by reference herein. Operation of the reduced pressure wound therapy system without a canister may sometimes be referred to herein as "PICO™", "PICO™-mode", or derivatives thereof.

Pump Assembly

Figure 3A:
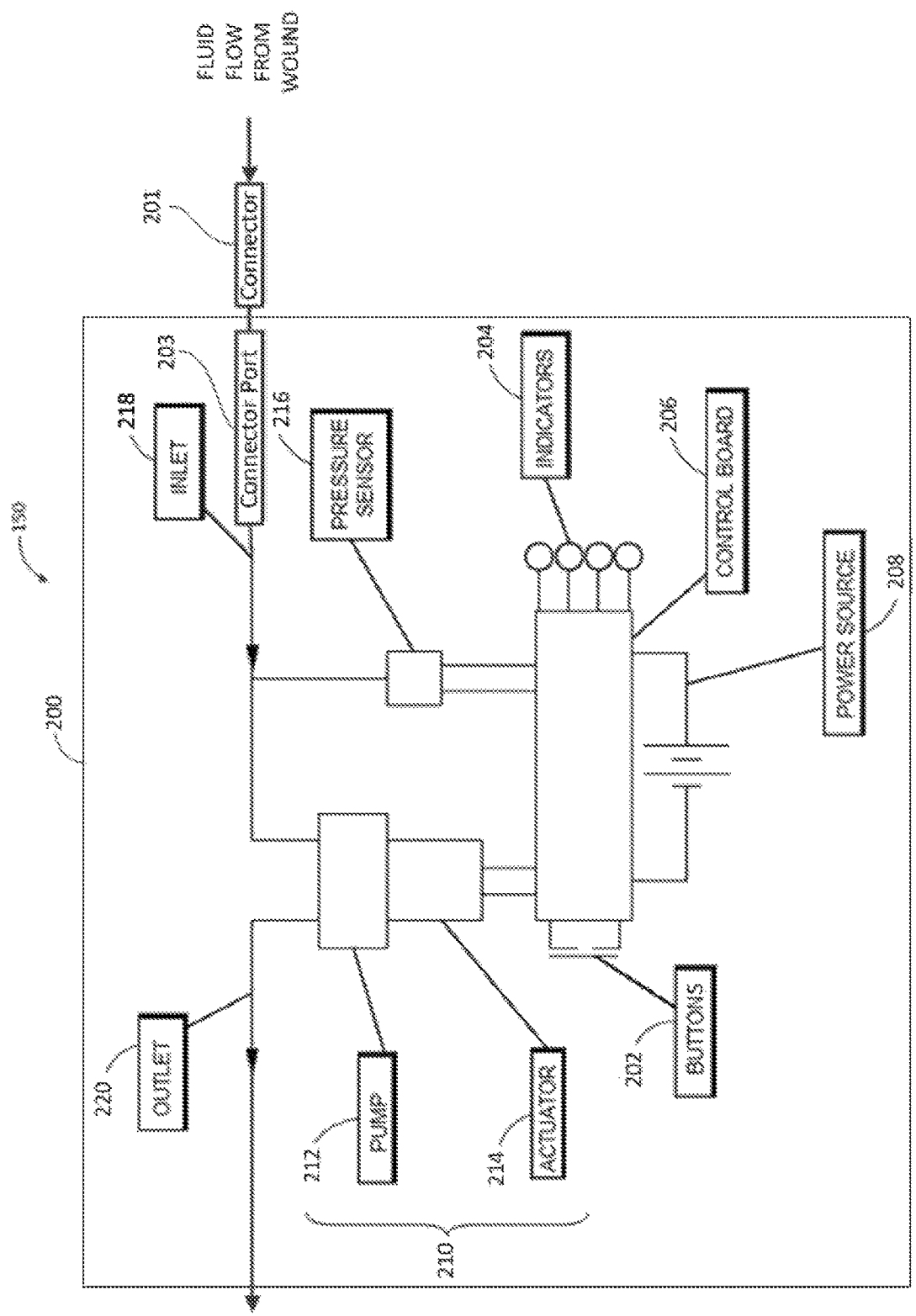
FIGS. 3A-3B illustrates a schematic of a reduced pressure wound therapy system including a pump assembly according to some embodiments.

FIG. 3A illustrates a schematic of the pump assembly 150 according to some embodiments. The pump assembly 150 can include a housing 200 that encloses or supports at least some components of the pump assembly 150. The pump assembly 150 can include one or more switches or buttons 202, one or more indicators 204, and a control board 206, The one or more buttons 202 and the one or more indicators 204 (which collectively make up a user interface) can be in electrical communication with the control board 206, which can include one or more controllers and memory. The one or more buttons 202 can be used for any suitable purpose for controlling an operation of the pump assembly 150. For example, the one or more buttons 202 can be used to activate the pump system 150, pause the pump assembly 150, and clear system indicators such as one or more of the one or more indications 204. The one or more buttons 202 can by any type of switch or button, such as a touchpad, touch screen, keyboard, and so on. In some embodiments, the one or more buttons 202 can be a press button. In various implementations, one or more buttons 202 can be included on a touchscreen interface.

The pump assembly 150 can include a connector port 203 adapted to receive a connector 201. The connector 201 can be a part of the canister or the wound dressing that is attached to the pump assembly 150, as described above. The connector 201 can be removably attached to the connector port 203. In some arrangements, a first connector 201 can be removed from the pump assembly 150 and replaced with a second connector 201 that is then attached to the pump assembly 150. For example, a first connector 201 that is connected to a RENASYS™ dressing can be removed from the connector port 203 and replaced with a second connector 201 that connected to a PICO™ dressing, thereby allowing the pump assembly 150 to be switched from canister to a canisterless mode of operation. As described in more detail below, the connector 201 and/or pump assembly 150 can be adapted to allow the pump assembly 150 to detect whether a canister or canisterless connector 201 is attached to the connector port 203. In some arrangements, the operation of the pump assembly 150 can be adjusted according to whether the pump assembly 150 detects a canister or a cansterless connector 201 is connected to the connector port 203.

In some embodiments, the connector port 203 can include one or more connector switches in electrical communication with the control board 206, which can include one or more controllers. The one or more connector switches can be configured to engage one or more connectors of the canister or the dressing. In some embodiments, the one or more connector switches can advantageously permit the pump assembly 150 (e.g., the control board 206) to differentiate between a canister connection and a dressing connection. In some embodiments, one or more of the connectors 201 can include one or more connector switches in addition to or in lieu of the one or more connector switches of the connector port 203. The connector switches contemplated herein can be mechanical, electrical, optical, and/or magnetic, or any other suitable switch, and can include sensors and the like. The connector switches can be configured to close or open an electrical circuit, thereby permitting the control board 206 to detect whether the connector switch is engaged or disengaged. For example, as described in more detail below, the connector port 203 can include a connector switch that is actuated by a portion of a connector 201 that couples a canister to the connector port 203. The connector switch can be further configured so that the switch is not actuated by a connector 201 that couples a dressing to the connector port 203, thereby allowing the control board 206 to detect whether a canister or a dressing is attached to the connector port 203. In some arrangements, the pump assembly 150 can be configured so that the connector switch is activated by a connector 201 that couples a dressing to the connector port 203 and is not activated by a connector 201 that couples a canister to the connector port 203.

With continued reference to FIG. 3A, the one or more indicators 204 can indicate one or more operating or failure conditions of the pump assembly 150. Each of the one or more indicators 204 may provide an indication regarding a different operating or failure condition. In some implementations, an active (e.g., lit) indicator of the one or more indicators 204 can represent a certain operation condition for the pump assembly 150. For example, a dressing indicator of the one or more indicators 204 can provide an indication as to presence of leaks in the TNP system 100, and an active dressing indicator can represent a leak. As another example, a dressing capacity indicator of the one or more indicators 204 can provide an indication as to the remaining fluid capacity of the wound dressing or canister, and an active dressing capacity indicator can represent that the wound dressing or canister is at or nearing capacity. As yet another example, a battery indicator of the one or more indicators 204 can provide an indication as to remaining capacity or life of a power source, such as batteries, and an active battery indicator can represent a low capacity. In some embodiments, the one or more indicators 204 can represent a combination of one or more of the above operating or failure conditions of the pump assembly 150 or other operating or failure conditions for the pump assembly 150.

In some implementations, the one or more indicators 204 can be icons. For example, the one or more indicators 204 can be activated (e.g., lit) via an illumination source such as LEDs (not shown) of pump assembly 150. The one or more indicators 204 can, for instance, be of a different color, two different colors (e.g., two indicators can share the same color), or same color. In some embodiments, the pump assembly 150 can include visual, audible, tactile, and other types of indicators or alarms configured to signal to the user various operating conditions. Such conditions include system on/off, standby, pause, normal operation, dressing problem, leak, error, and the like. The indicators can include speakers, displays, light sources, etc., or combinations thereof. In various implementations, one or more buttons indicators 204 can be included on a touchscreen interface.

The pump assembly 150 can be powered by a power source 208 such as a battery power cell or any other suitable power source. The pump assembly 150 can also include a source of negative pressure 210, which can include a pump 212 powered by an actuator 214, such as an electric motor. In some embodiments, the actuator 214 is integrated into the pump 212. The negative pressure source 210 can be a rotary diaphragm pump or other diaphragm pump, a piezoelectric pump, a peristaltic pump, a piston pump, a rotary vane pump, a liquid ring pump, a scroll pump, a diaphragm pump operated by a piezoelectric transducer, a pump operated by a voice coil actuator, or any other suitable pump or micropump or any combinations of the foregoing. The pump assembly 150 can also include one or more pressure sensors 216 that measure pressure in the fluid flow path.

The pump assembly 150 can further include an inlet 218 to connect the pump assembly 150 to the wound dressing. For example, the inlet 218 can be connected to the connector port 203 and the connector 201 that is in fluid communication with the wound dressing via a fluid flow path.

The pump assembly 150 can also include an outlet 220. The outlet 220 can vent or exhaust gas to the atmosphere. In some embodiments, a filter (not shown) can be interposed between the outlet 220 and the atmosphere. The filter can provide filtration of the gas prior to venting the gas to the atmosphere. The filter can be a bacterial filter, odor filter, or any combination thereof. In some embodiments, a dampening component (not shown), such as a noise dampening component, can be interposed between the outlet 220 and the atmosphere. The dampening component can reduce the noise generated by the pump assembly 150 during operation. In some implementations, the pump assembly 150 can communicate information, such as information related to provision of negative pressure therapy, to one or more remote devices. Such communication can be performed using a wired or wireless interface.

Figure 3B:
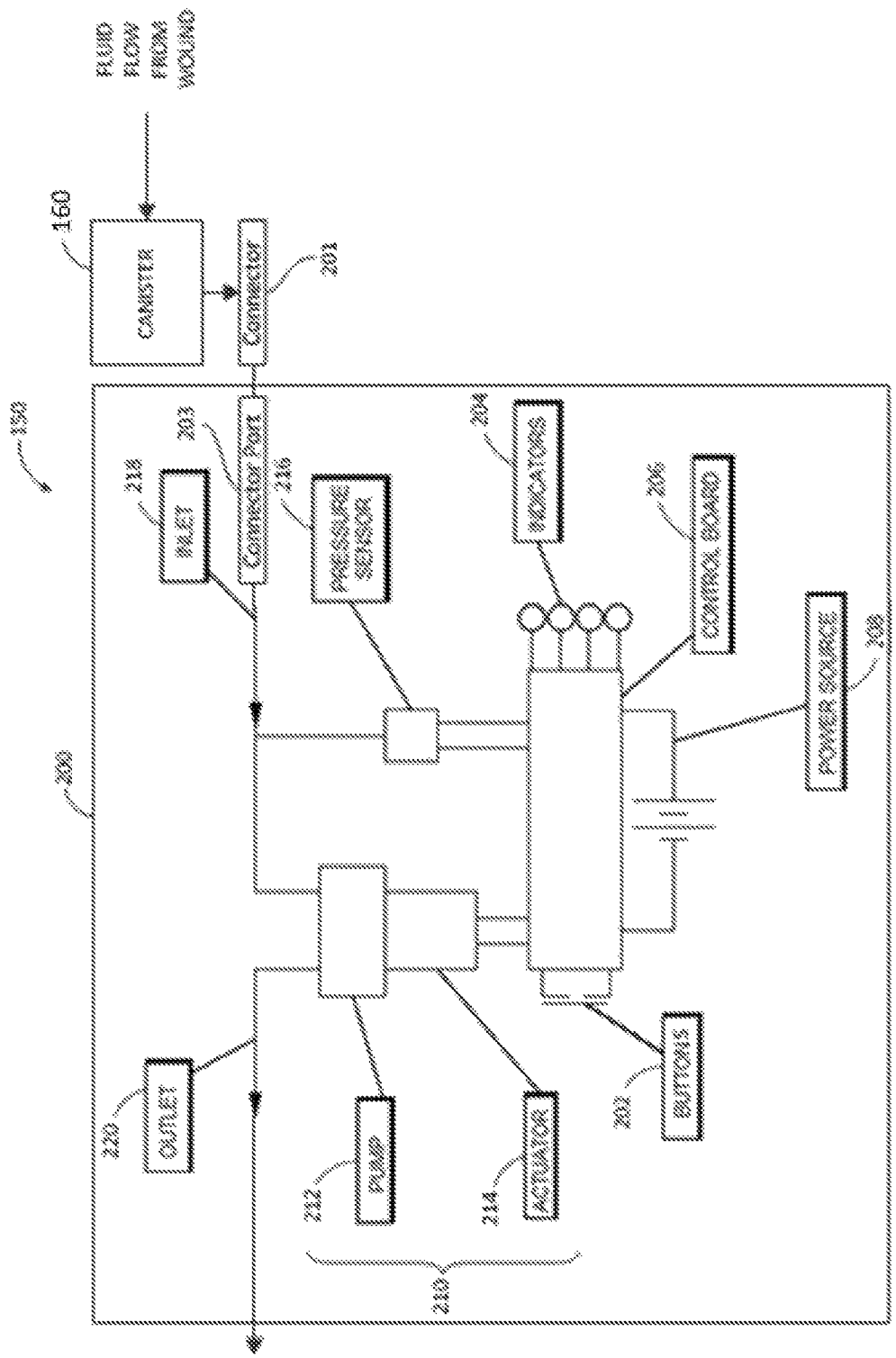

FIG. 3B illustrates the pump assembly 150 of FIG. 3A with a canister 160 additionally positioned in a fluid flow path between the inlet 218 and the wound dressing. In the illustrated embodiment, the connector 201 fluidically connects the canister 160 to the connector port 203. As discussed further below, the connector 201 can be configured to signal to the pump assembly 150 whether the connector port 203 is connected to a wound dressing directly or whether a canister 160 is disposed between the connector 203 and the wound dressing.

In some embodiments, the control board 206 (e.g., a controller) adjusts one or more operational parameters of negative pressure wound therapy depending on whether the pump assembly is connected to the canister or the dressing. For example, in canisterless mode, the level of negative pressure provided to the wound can be reduced compared to canister mode because the wound is exuding a smaller amount of fluid. As another example, detection of one or more operating conditions can be enabled, disabled, or adjusted. For instance, in canisterless mode, canister fill detection (or blockage detection) and alarming can be disabled and, instead, dressing full detection and alarming can be enabled.

In some embodiments, the pump assembly 150 includes a user interface, such as one or more displays, indicators, lights, buttons, switches, speakers, vibrating elements, etc. The user interface can be adjusted based on detection of a canister. For example, in canister mode, the user interface can include an indicator alerting a user when canister becomes full. In canisterless mode, this indicator can be replaced with an indicator alerting the user when the dressing become full. In some embodiments, the indicators are icons.

Figure 4A:
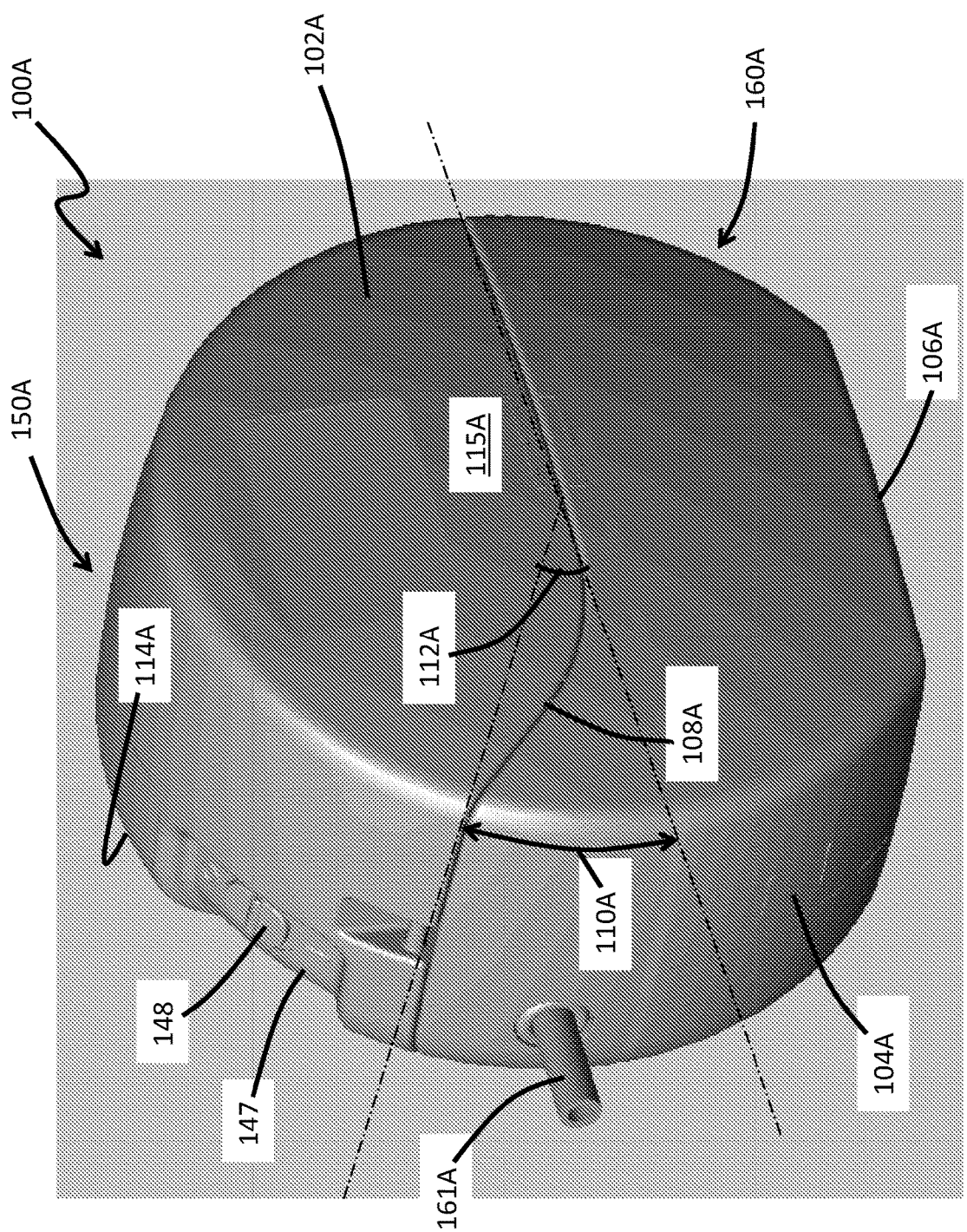
FIG. 4A is a front perspective view showing the front and right sides of an embodiment of the TNP system with a canister attached to the pump assembly.

FIG. 4A depicts in a perspective view an embodiment of the TNP system 100A with a canister 160A attached to the pump assembly 150A. The canister 160A can have an inlet 161A through which wound exudate can enter the canister 160A. As shown in FIG. 4A, the TNP system 100 can have a disc-shaped or at least partially circular form when the pump assembly 150A is attached to the canister 160A and the system is viewed from the left or right side. For ease of discussion, each opposing surface or side of the TNP system 100A that has an at least partially circular shape will be referred to as a face 102A. The surface of the TNP system 100A that connects the two opposing faces 102A will be referred to as an edge 104A. In FIG. 4A, the inlet 161A protrudes from the edge 104A of the canister 160A. For ease of discussion, the portion of the edge 104A from which the inlet 161A protrudes will be referred to as the front of the TNP system 100A. Accordingly, FIG. 4A shows a partial front and right view of the TNP system 100A. However, from the perspective of the TNP system 100A, the left face 115A of the TNP system is visible when the TNP system 100A is viewed from the right. The right face 114A of the TNP system 100A is not visible in FIG. 4A. As shown in FIG. 4A, the pump assembly 150A can include an on/off switch 148. In the illustrated embodiment, the on/off switch 148 is located in a recessed portion 147 of the edge 104A. Specifically, the on/off switch 148 is located on the front of the pump assembly 150A and toward the left face 114A of the pump assembly 150A.

With continued reference to FIG. 4A, the edge 104A of the canister 160A can have a flat bottom surface or base 106A that extends between the front and rear of the canister 160A. The base 106A may form a flat or linear surface. The base 106A can encourage orienting the TNP system 100 so that the on/off switch 148 is vertically above the inlet 161, as shown in FIG. 4A. As discussed in more detail below, the TNP system 100 can be adapted to minimize or prohibit liquid (e.g., wound exudate) within the canister 160A from wetting components of the pump assembly 150A when the TNP system is supported on the base 106A.

The TNP system 100A can have a seam 108A at the interface between the pump assembly 150A and the canister 160A. According to the reference system set forth above to describe the TNP system 100A, the seam 108A is at the interface between a top surface of the canister 160A and a bottom surface of the pump assembly 150A. As shown in FIG. 4A, a portion of the seam 108A can run substantially parallel to the base 106A. In the illustrated embodiment, the seam 108A rises toward the top of the TNP system 100A as the seam 108A approaches the inlet 161A in a direction from the rear of the TNP system 100A to the front of the TNP system 100A. The amount the seam 108A rises relative to the portion of the seam 108A that is parallel to the base 106A can be defined by an arc length 110A, as indicated in FIG. 4A. A canister angle 112A can be defined that corresponds to the arc length 110A such that the arc length 110A is equal to the radius of the face 102A multiplied by the canister angle 112A, as shown in FIG. 4A. In the illustrated embodiment, the canister angle 112A is about 30 degrees. In some embodiments, the canister angle 112A can be an angle of: 10 degrees, 20 degrees, 40 degrees, 60 degrees, or a value between any of these aforementioned values. As discussed in more detail below, the canister angle 112A can be selected to prevent or minimize liquid (e.g., wound exudate) within the canister 160A from wetting components of the pump assembly 150A.

Figure 4B:
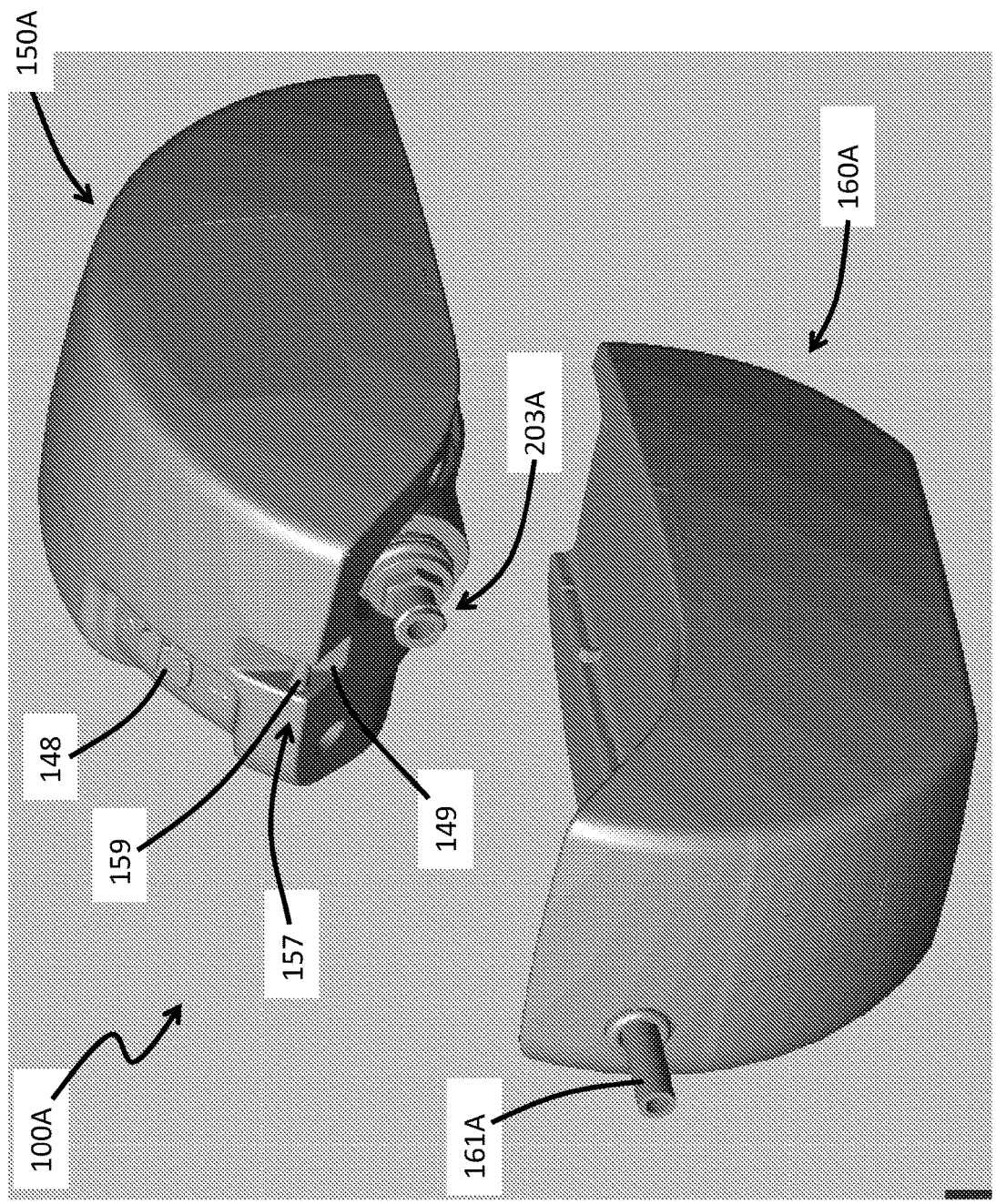
FIG. 4B is a front perspective view showing the front and right sides of the TNP system of FIG. 4A with the canister detached from the pump assembly.

FIG. 4B shows an exploded view of the TNP system 100A of FIG. 4A, with the pump assembly 150A slid back to disengage the pump assembly 150A from the canister 160A. As shown in FIG. 4B, the connector port 203A of the pump assembly 150A can be exposed when the canister 160A is disengaged from the pump assembly 150A. The connector port 203A is similar to the connector port 203 except as described differently below. The features of the connector port 203A can be combined or included with the connector port 203 or any other embodiment discussed herein. As shown in FIG. 4B, the pump assembly 150A can include an attachment member or strap anchor 157 that allows a strap (not shown) to be attached to the pump assembly 150A. In the illustrated embodiment, the attachment member 157 is a bar 159 that spans a groove 149 thereby allowing a strap to be passed around the bar 159 and secured back onto itself to attach the strap to the pump assembly 150A. In some embodiments, the strap can include a hook or clasp that is secured to the bar 159. As discussed in more detail below, the attachment member 157 can be adapted to prevent or minimize liquid (e.g., wound exudate) within the canister 160A from wetting components of the pump assembly 150A when the TNP system 100A is suspended from a strap connected to the attachment member 157. In some embodiments, the attachment member 157 is arranged so that the connector port 203A is positioned near the top of the internal volume of the canister 160A when the TNP system 100A is suspended from the attachment member 157. In the illustrated embodiment, the attachment member 157 is positioned near the interface between the top surface and the bottom surface of the pump assembly 150A.

As shown in FIG. 4B, the bottom surface of the pump assembly 150A and the top surface of the canister 160A can be configured to allow the pump assembly 150A and the canister 160A to slidably connect with one another. In the illustrated embodiment, the canister 160A and the pump assembly 150A are connected together by sliding the canister 160A relative to the pump assembly 150A in a direction from the front side of the pump assembly 150A to the rear side of the pump assembly 150A. The TNP system 100A can include a stop or locking member (not shown) that secures the canister 160A to the pump 150A. The canister 160A can be secured to the pump assembly 150A by sliding the canister 160A toward the rear side of the pump assembly 150A until the canister 160A reaches a stop. As shown in FIG. 4A, when the pump assembly 150A and the canister 160A are secured together, the front side of the pump assembly 150A can align with the front side of the canister 160A, and the rear side of the pump assembly 150A can align with the rear side of the canister 160A. The pump assembly 150A and the canister 160A can be disengaged from one another by sliding the canister 160A relative to the pump assembly 150A in a direction from the rear side of the pump assembly 150A to the front side of the pump assembly 150A.

With continued reference to FIG. 4B, the connector port 203A is located on the bottom surface of the pump assembly 150A. The TNP system 100A is arranged so that the connector port 203A is positioned near the top of the canister 160A. In some configurations, the connector port 203A connects to a volume of the canister 160A that is vertically above or superior to 80% of the rest of the internal volume of the canister 160A. In some embodiments, the canister volume to which the connector port 203A connects is superior to between 60% and 95% of the rest of the internal volume of the canister 160A. In some embodiments, the connector port 203A connects to a volume of the canister 160A that is superior to 80% of the rest of the internal volume of the canister 160A when the TNP system 100A is suspended from a strap connected to the attachment member 157, In some embodiments, the canister volume to which the connector port 203A connects is superior to between 60% and 95% of the rest of the internal volume of the canister 160A when the TNP system 100A is suspended from the attachment member 157. In some embodiments, the connector port 203A connects to a volume of the canister 160A that is superior to 80% of the rest of the internal volume of the canister 160A when the TNP system 100 is supported on the base 106A. In some embodiments, the canister volume to which the connector port 203A connects is superior to between 60% and 95% of the rest of the internal volume of the canister 160A when the TNP system 100A is supported on the base 106A.

FIG. 4B illustrates that the TNP system 100A can be arranged to enhance securement of the canister 160A to the pump assembly 150A. In the illustrated embodiment, the top surface of the canister 160A and the bottom surface of the pump assembly 150A are shaped so that gravity tends to keep the canister 160A on the pump assembly 150A when the pump assembly 150A is suspended from the attachment member 157. As shown in FIG. 4B, the top surface of the canister 160A can have a ramped portion that ramps upward toward the front of the canister 160A. The bottom surface of the pump assembly 150A can have an inclined portion ramps upward toward the front of the pump assembly 150A. The ramped portion of the canister 160A and the inclined portion of the pump assembly 150A can be sized so that the ramped portion is flush with the inclined portion when the canister 160A is attached to the pump assembly 150A. When the pump assembly 150A is suspended from the attachment member 157, the canister 160A is attached to the pump assembly 150A by sliding the canister 160A in the direction of gravity, i.e. from the front of the pump assembly 150A toward the rear of the pump assembly 150A. After the canister 160A and the pump assembly 150A are connected, the ramped portion of the top surface of the canister 160A forms an overhang that is supported on the inclined portion of the bottom surface of the pump assembly 150A, thereby enhancing retention of the canister 160A on the pump assembly 150A when the pump assembly 150A is suspended from the attachment member 157.

Figure 4C:
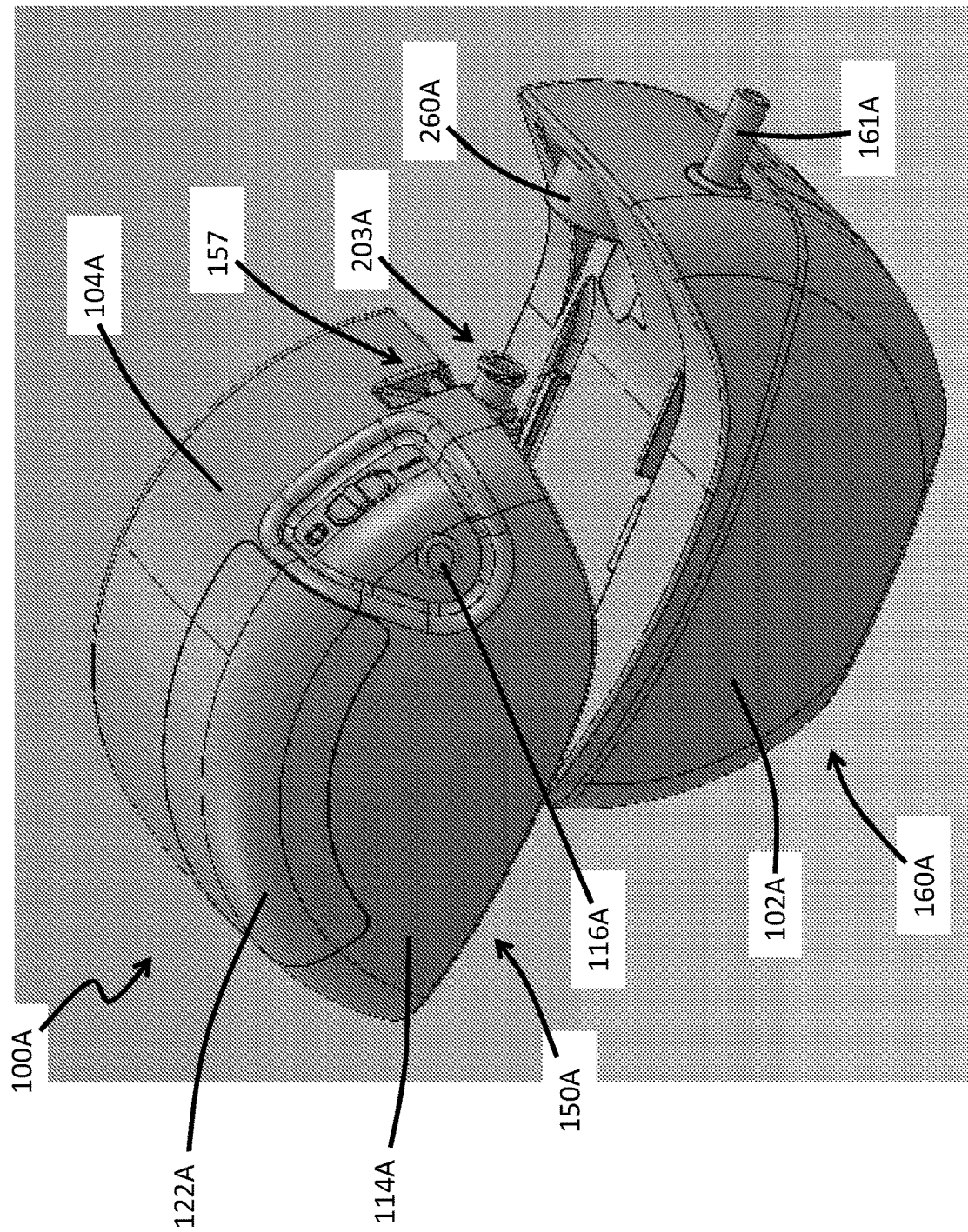
FIG. 4C is a front perspective view showing the front and left sides of the TNP system of FIG. 4A with the canister detached from the pump assembly.

FIG. 4C is a partial left and front perspective view the TNP system 100A shown in FIG. 4B, with the TNP system 100A oriented so that the right face 114A of the TNP system 100A is visible. As shown in FIG. 4C, the connector port 203A can align with and be received in a canister connector 260A when the pump assembly 150A is connected to the canister 160A. In the illustrated embodiment, the TNP system 100A has the attachment member 157 disposed on the pump assembly 150A. In certain arrangements, the attachment member 157 can be disposed on the canister 160A. For example, the attachment member 157 can be disposed on the canister 160A near the seam 108A and between the inlet 161A and the canister connector 260A.

The TNP system 100 can include one or more filters (not shown) interposed between the connector port 203A and the canister connector 260A. The filter can provide filtration of the gas prior to the gas passing from the canister 160A to the pump assembly 150A. The filter can be a bacterial filter, odor filter, or any combination thereof. In some embodiments, the filter can include a stop filter that prevents liquid from passing through the filter to reach the pump assembly 150A. For example, the stop filter can be a porous mesh of material that swells upon contact with liquid. When the stop filter is dry, the porous mesh is in an "un-swelled" state that allows gas (e.g., air) to pass through the pores of the stop filter to reach the pump assembly 150A, thereby enabling the pump assembly 150A to draw gas from the canister 160A and establish a negative pressure inside the canister 160A. When liquid contacts the stop filter, the stop filter material can swell to occlude the pores of the stop filter, thereby preventing the pump assembly 150A from drawing liquid through the stop filter. In this way, the stop filter can protect the pump assembly 150A from contacting a liquid (e.g., wound exudate). The position of the attachment member 157 orients the stop filter near the top of the canister 160A when the TNP system 100A is suspended from a strap attached to the attachment member 157. The canister 160A is configured to orient the stop filter near the top of the canister 160A when the TNP system 100A is supported on the base 106A.

The pump assembly 150A can include one or more indicators on the left side of the pump assembly 150A. For example, the pump assembly 150A can include an alarm indicator 116A. The alarm indicator 116A can be adapted to signal an operational mode of the pump assembly 150A. For example, the alarm indicator 116A can glow red or flash to indicate a malfunction in the operation of the pump assembly 150A. The alarm indicator 116A can glow green or shine continuously when the pump assembly 150A is functioning properly. In the illustrated embodiment, the alarm indicator 116 is disposed on a recessed portion of the right face 114A of the pump assembly 150A. The alarm indicator 116A can be disposed on the TNP system 100A at a location other than the right face 114A of the pump assembly 150A.

The pump assembly 150A can include one or more indicators that are covered by a fascia 122A. The fascia 122A can extend over a portion of the face 102A and the edge 104A of the pump assembly 150A. In the illustrated embodiment, the fascia 122A wraps over the interface between the top and the right side of the pump assembly 150A. The fascia 122A can be clear or partially opaque. In some variants, the fascia 122A is partially opaque so that icons marked on an inner surface of the fascia 122A can be seen through the fascia 122A when the indicator is lit. The appearance of the fascia 122A can be selected to substantially match the appearance of the surrounding portions of the pump assembly 150A so that icons marked on an inner surface of the window 122A are not visible when the indicators are not lit. The fascia 122A can be reversibly removable from the pump assembly 150A. In some configurations, the fascia 122A is fused to the pump assembly 150A and cannot be removed from the pump assembly 150A without destroying the fascia 122A. In at least one embodiment, the fascia 122A and the pump assembly 150A are fused together and arranged so that the transition between the fascia 122A and the pump assembly 150A is not apparent, giving the pump assembly 150A a clean and minimalist appearance.

Figure 4D:
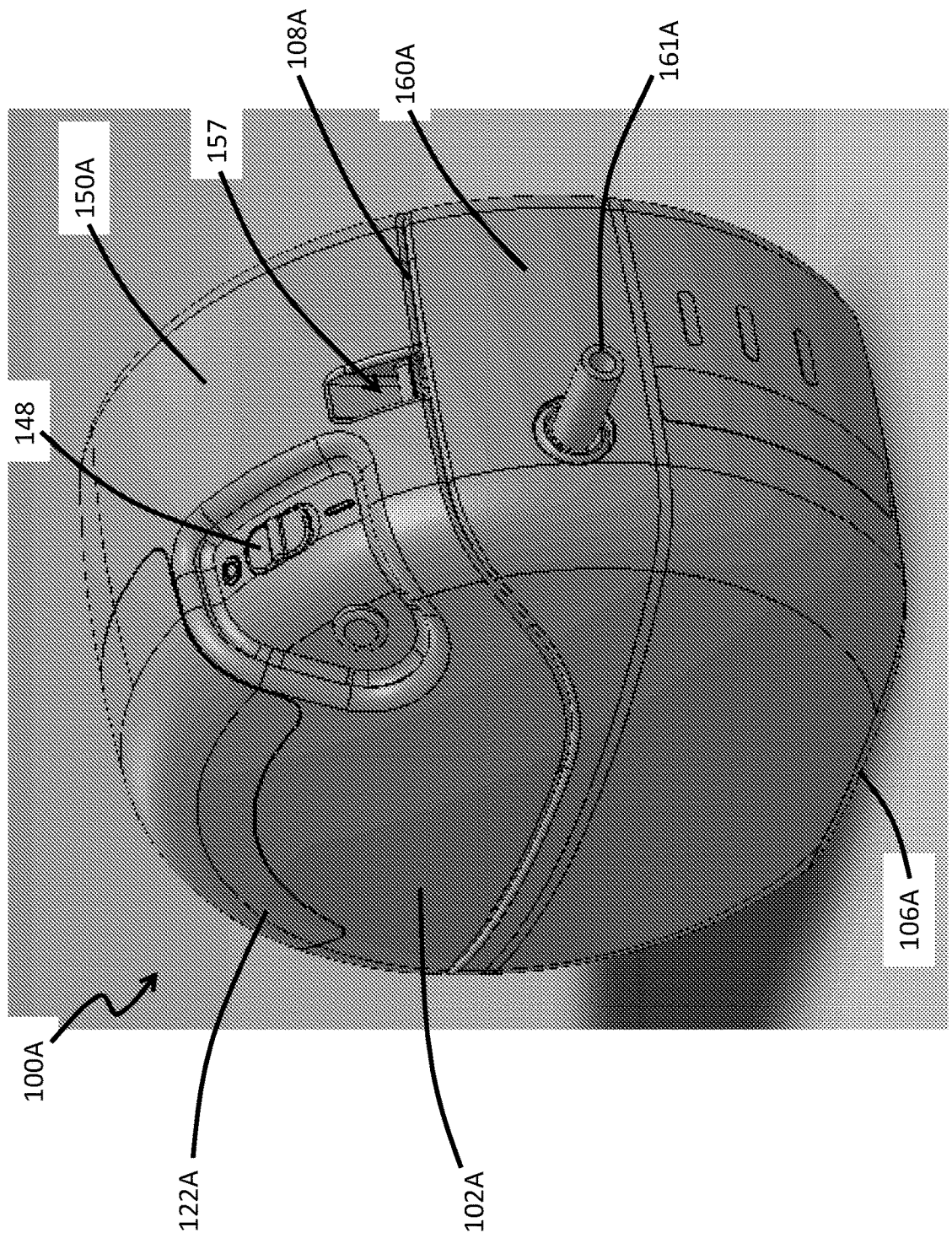
FIG. 4D is a front perspective view showing the front and left sides of the TNP system of FIG. 4C with the canister attached to the pump assembly.

FIG. 4D depicts in a perspective view the TNP system 100A shown in FIG. 4(C with the pump assembly 150A connected to the canister 160A. As shown in FIG. 4D, the attachment member 157 is disposed on the edge 104A of the TNP system 100A and is adjacent to the portion of the seam 108A that is between the inlet 161A and the pump assembly 150A. In the illustrated embodiment, the attachment member 157 is located along a medial plane of the pump assembly 150A that is substantially equidistant from the left and right sides of the TNP system 100A. The attachment member 157 can be adapted so that when the TNP system 10A is suspended from a strap connected to the attachment member 157, the inlet 161 and the connector port 203A are positioned near the top of the TNP system 100A, thereby minimizing or reducing the ability of liquid within the canister 160A from passing through the connector port 203A and wetting components of the pump assembly 150A.

As shown in FIG. 4D, when the TNP system 100A is supported on the base 106A of the canister 160A, the connector port 203A (shown in FIG. 4C) will be near the top of the canister 160A and within the portion of the canister 160A that rises toward the top of the TNP system 100A. In this way, the connector port 203A is protected from contacting liquid within the canister 160A. Positioning the connector port 203A to align with the portion of the canister 160A that rises toward the top of the TNP system 100A also maximizes the amount of volume the canister 160A can hold before the level of the liquid within the canister 160A reaches the level of the connector port 203A.

Figure 4E:
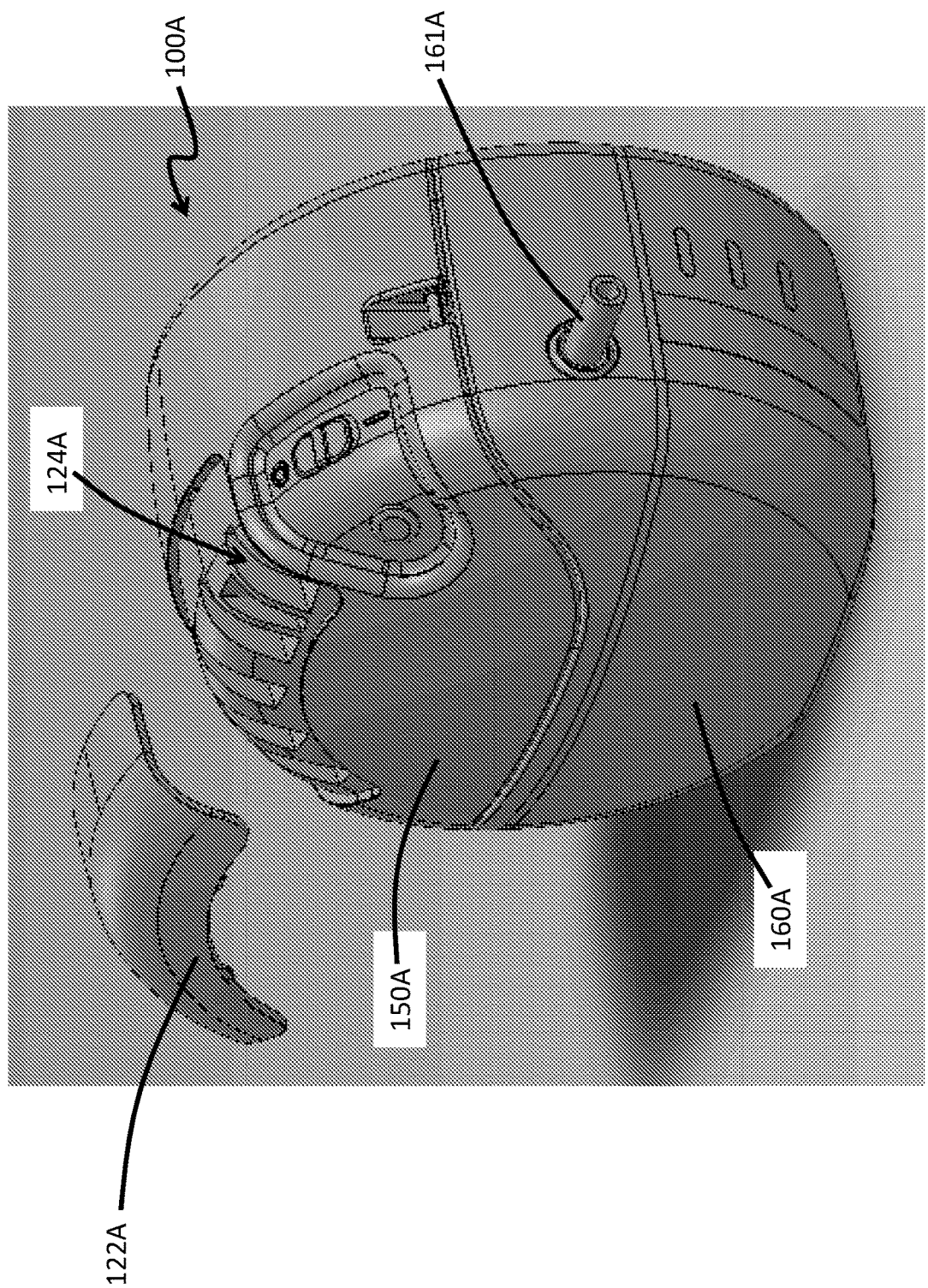
FIG. 4E is a perspective view showing the front and left sides of the TNP system of FIG. 4D with the window shown removed from the pump assembly.

FIG. 4E shows the TNP system 100A shown in FIG. 4C with the fascia 122A removed to illustrate that the pump assembly 150A can include a plurality of gates 124A to help direct light through the fascia 122A. The gates 124A can help to selectively illuminate each of a plurality of indicators of the pump assembly 150A. As discussed above, the fascia 122A can include one or more icons marked on the inner surface of the fascia 122A. The icons can be back lit by a light source (e.g., LED) that shines through the fascia 122A. The TNP system 100A can include a plurality of light sources (not shown) with each of the light sources being individually seated within a gate 124A. The icons on the fascia 122A can be clearly visible when the light source shines through the icon and not visible, or minimally visible, when the icons are not backlit by a light source that shines through the icon. The gates 124A can direct the light of an individual light source to minimize a first light source of the plurality of light sources from cross-illuminating an icon that overlies a second light source of the plurality.

Figure 4F:
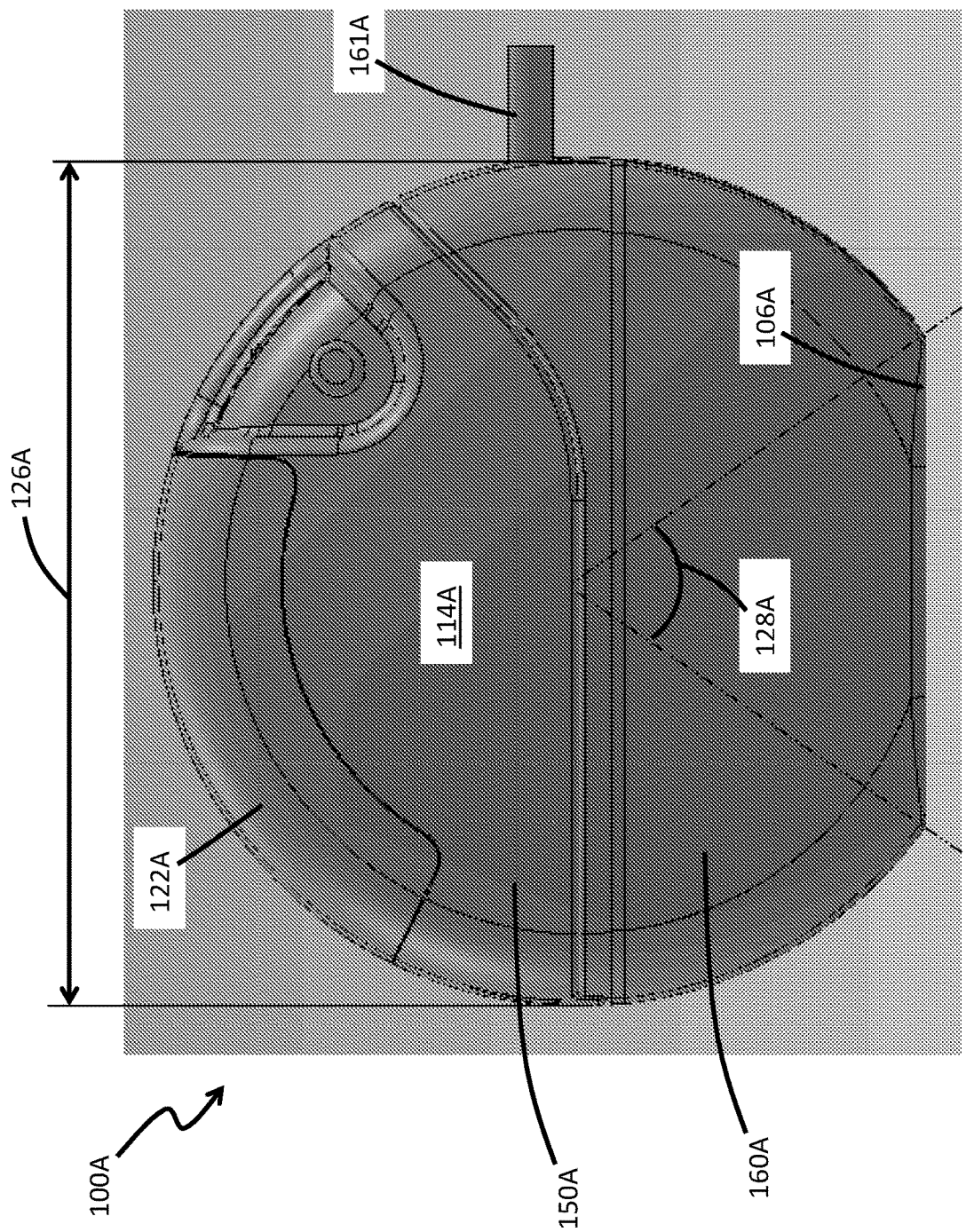
FIG. 4F is a left side view of the TNP system of FIG. 4A.

FIG. 4F depicts in a frontal view of the right face 114A of the TNP system 100A shown in FIG. 4C with the pump assembly 150A connected to the canister 160A. As shown in FIG. 4F, the TNP system 100A can have a substantially circular form when viewed from a front view of the right face 114A. The TNP system 100A can have an overall diameter 126A, as indicated in FIG. 4F. The substantially circular form can be truncated along the base 106A of the canister 160A, as discussed above. The span of the base 106A can be characterized by a base angle 128A, as indicated in FIG. 4F. The base angle 128A can be selected to provide good stability to the TNP system 100A while maintaining large capacity for the canister 160A. In the illustrated embodiment, the base angle 128A is about 70 degrees. In some embodiments, the base angle 128A can be an angle of: 45 degrees, 60 degrees, 90 degrees, 120 degrees, or a value between any of these aforementioned values.

Figure 4G:
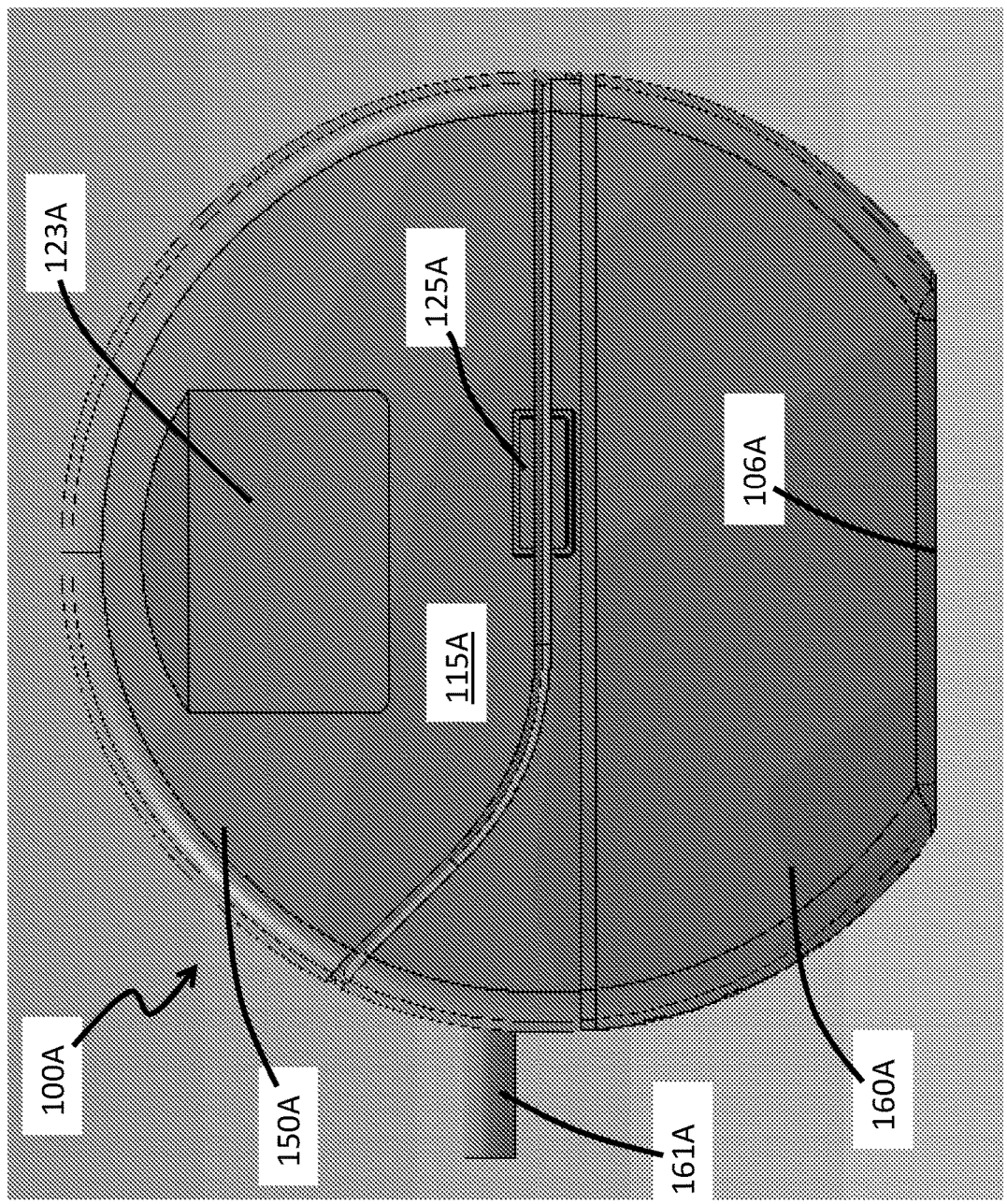
FIG. 4G is a right side view of the TNP system of FIG. 4A.

FIG. 4G depicts in a frontal view of a left face 115A of the TNP system 100A shown in FIG. 4F. As shown in FIG. 4G, the pump assembly 150A can include a grip 123A that facilitates a user's ability to slide the pump assembly 150A relative to the canister 160A. As discussed above, the pump assembly 150A and the canister 160A are slid relative to one another in order to engage or disengage the pump assembly 150A and the canister 160A from one another. In the illustrated embodiment, the grip 123A is a recessed portion of the pump assembly 150A. The grip 123A can be sized to accommodate at least a portion of a user's hand (e.g., palm or fingers) to allow the user to more securely hold the pump assembly 150A. The grip 123A can enhance a user's ability to hold the pump assembly 150A as the pump assembly 150A is connected or disconnected from the canister 160A. In the illustrated embodiment, the grip 123A is diametrically opposed from the base 106A of the canister 160A when the pump assembly 150A is connected to the canister 160A.

With continued reference to FIG. 4G, the TNP system 100A can also include one or more locking means 125A that prevent the pump assembly 150A from sliding relative to the canister 160A before the locking means 125A are disengaged. The locking means 125A can be a tab on the pump assembly 150A that slides along the seam 108A to interlock with or disengage from a corresponding slot disposed on the canister 160A. The orientation can be reversed. For example, the locking means 125A can be a sliding tab disposed on the canister 160A and the corresponding slot can be disposed on the pump assembly 150A. In some arrangements, the locking means can be a button that splays apart internal interlocks of the pump assembly 150A and the canister 160A when the button is pressed. In the illustrated embodiment, each of the pump assembly 150A and the canister 160A includes a locking means 125A. In some arrangements, only one of the pump assembly 150A and the canister 160A will include a locking means 125A. In some arrangements, the TNP system 100A does not include a locking means 125A.

Figure 4H:
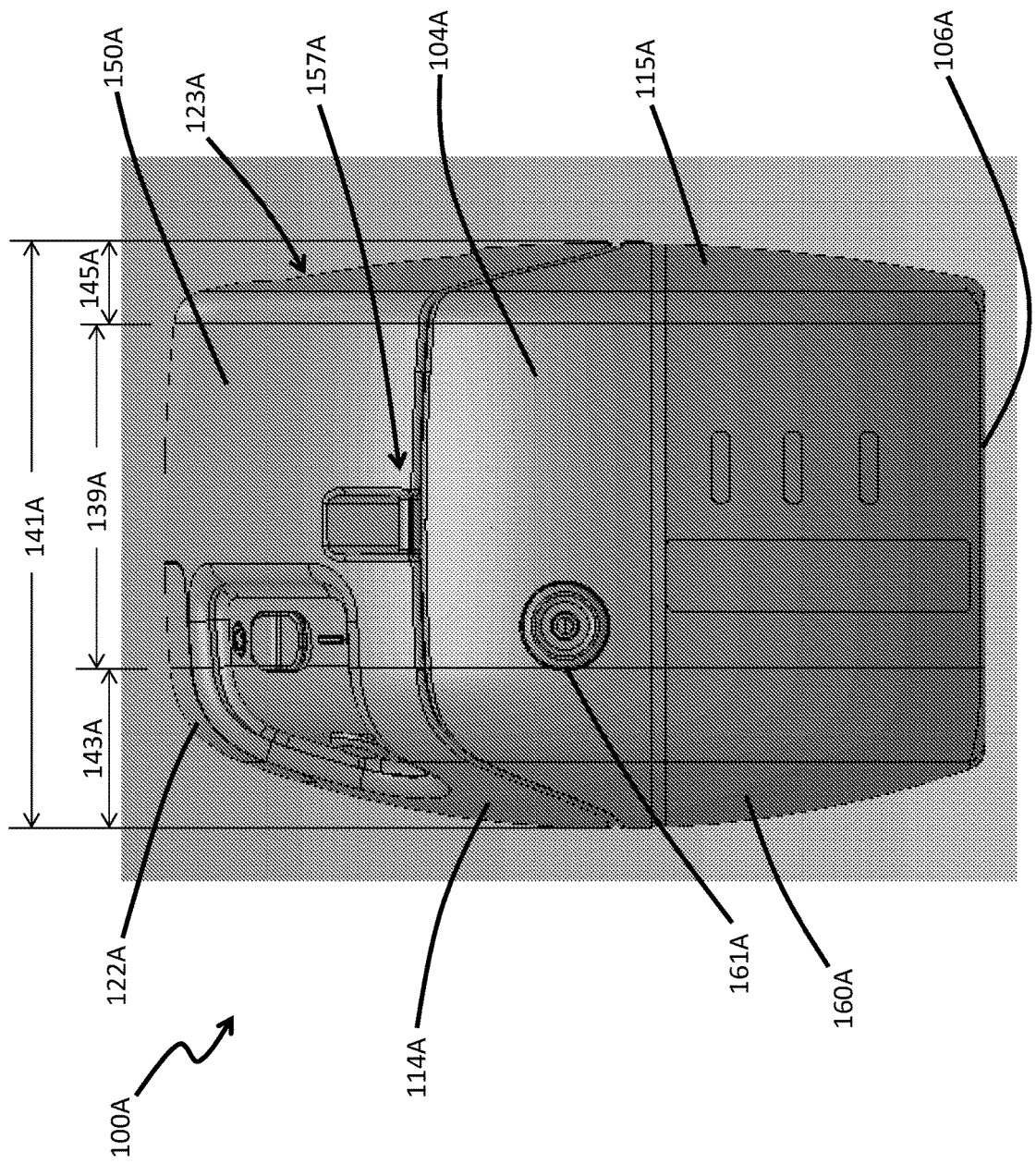
FIG. 4H is a front view of the TNP system of FIG. 4A.

FIG. 4H depicts in a frontal view of the edge 104A of the TNP system 100A shown in FIG. 4F. FIG. 4F shows the portion of the edge 104A from which the inlet 161A protrudes. As shown in FIG. 4F, the fascia 122A can wrap from the edge 104A to the right face 114A of the TNP system 100A. The TNP system 100A can have an overall width 141A that defines the maximum extent between the right face 114A and the left face 115A, as indicated in FIG. 4H. The right face 114A can bulge laterally away from the edge 104A by a right width 143A, as indicated in FIG. 4H. The left face 115A can bulge laterally away from the edge 104A by a left width 145A. The overall width 141A can be the sum of the right width 143A, the left width 145A, and an edge width 139A, as shown in FIG. 4H.

The TNP system 100A can be characterized by an overall aspect ratio that is defined as the ratio of the overall diameter 126A to the overall width 141A. In the illustrated embodiment, the TNP system has an overall aspect ratio of about 1.5. In some embodiments, the TNP system 100A can have an overall aspect ratio of about: 1.0, 1.2, 1.4, 1.6, 1.8, 2.0, 3.0, or a value between any of these aforementioned values. The TNP system 100A can be characterized by a right bulge ratio that is defined as the ratio of the right width 143A to the overall width 141A. In the illustrated embodiment, the TNP system has a right bulge ratio of about 0.27. In some embodiments, the TNP system 100A can have a right bulge ratio of about: 0.10, 0.15, 0.20, 0.25, 0.30, 0.35, 0.40, 0.60, or a value between any of these aforementioned values. The TNP system 100A can be characterized by a left bulge ratio that is defined as the ratio of the left width 145A to the overall width 141A. In the illustrated embodiment, the TNP system has a left bulge ratio of about 0.14. In some embodiments, the TNP system 100A can have a left bulge ratio of about: 0.05, 0.10, 0.15, 0.20, 0.30, 0.40, or a value between any of these aforementioned values.

Figure 4I:
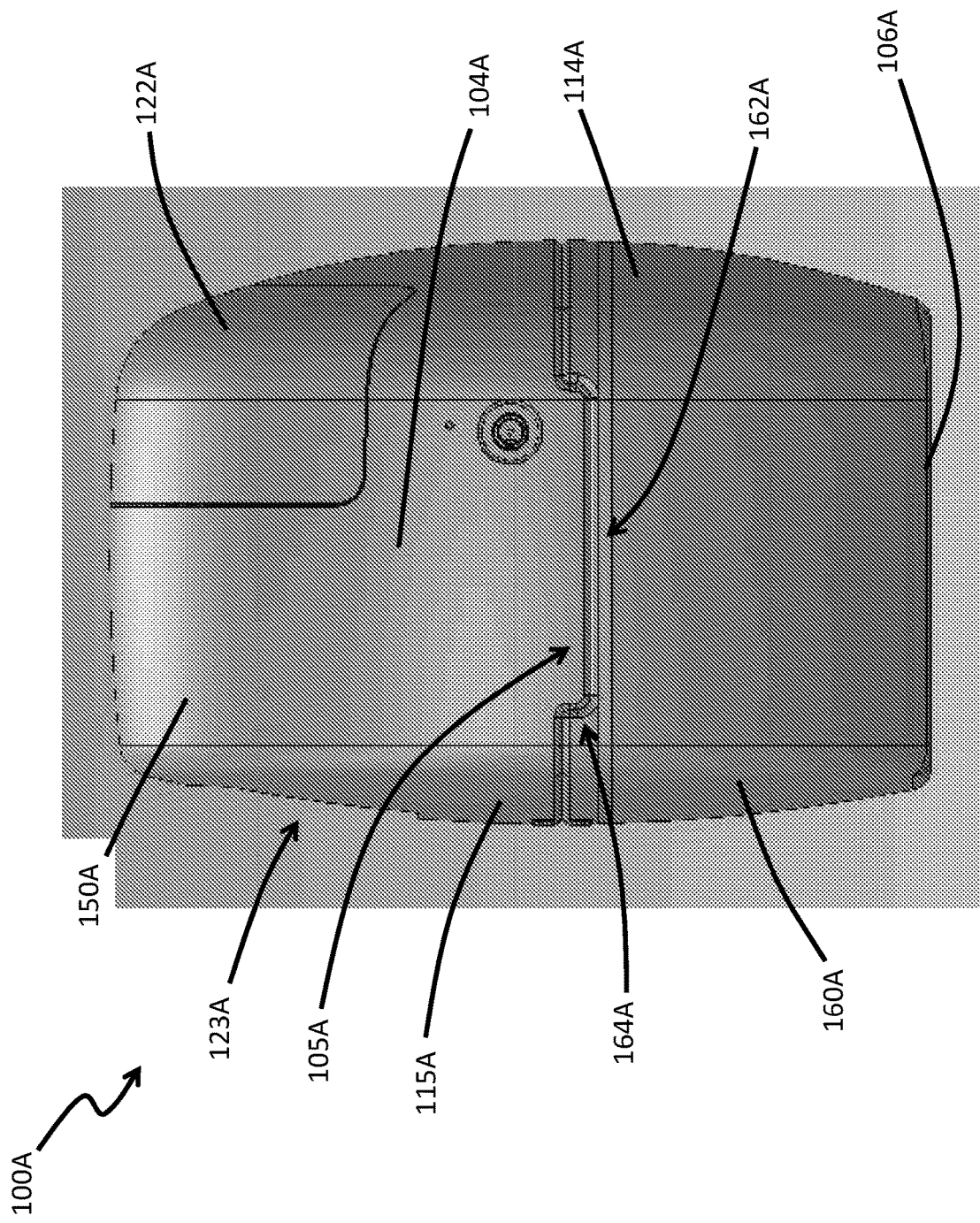
FIG. 4I is a rear view of the TNP system of FIG. 4A.

FIG. 4I depicts in a frontal view of the rear side of the TNP system 100A shown in FIG. 4H. FIG. 4I shows the portion of the edge 104A that faces away from the inlet 161A. FIG. 4I illustrates that the canister 160A can have a recessed bed 162A that is disposed between two opposing sidewalls 164A of the canister 160A. As described in more detail below, a medial portion 105A of the pump assembly 150A can seat on the recessed bed 162A when the pump assembly 150A is connected to the canister 160A. The TNP system 100A can be characterized by a rail ratio that is defined as the ratio of the width of the medial portion 105A to the overall width 141A. In the illustrated embodiment, the TNP system has a rail ratio of about 0.47. In some embodiments, the TNP system 100A can have a rail ratio of about: 0.20, 0.30, 0.40, 0.45, 0.50, 0.60, 0.80, or a value between any of these aforementioned values.

Figure 4J:
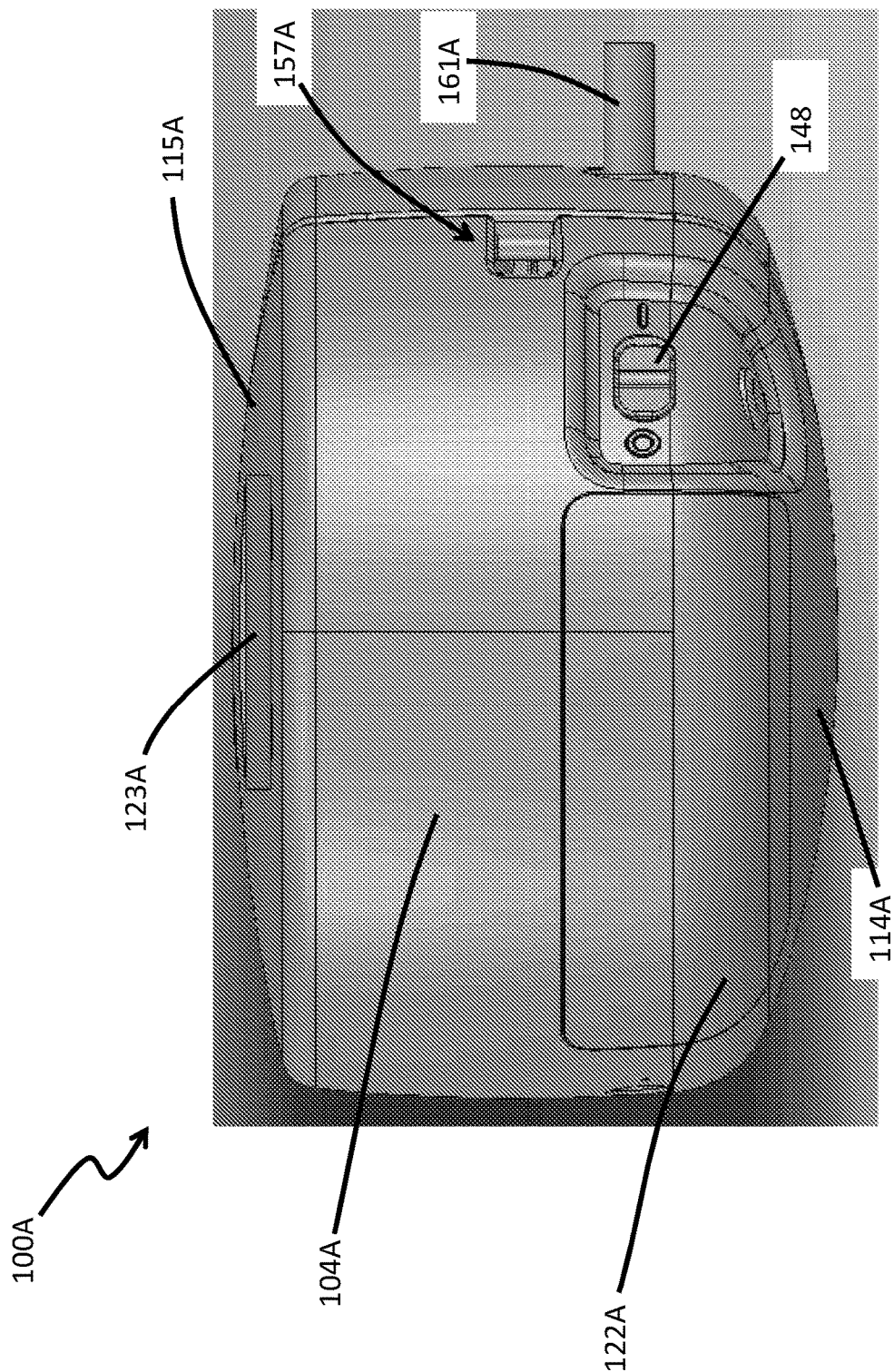
FIG. 4J is a top view of the TNP system of FIG. 4A.

FIG. 4J depicts in a top view of the TNP system 100A shown in FIG. 4H. The grip 123A is positioned near the top of the left face 115A. The fascia 122A extends from the edge 104A to the right face 114A, as described above. The strap anchor 157A is disposed near a medial plane of the TNP system 100 and in proximity of the inlet 161A.

Figure 4K:
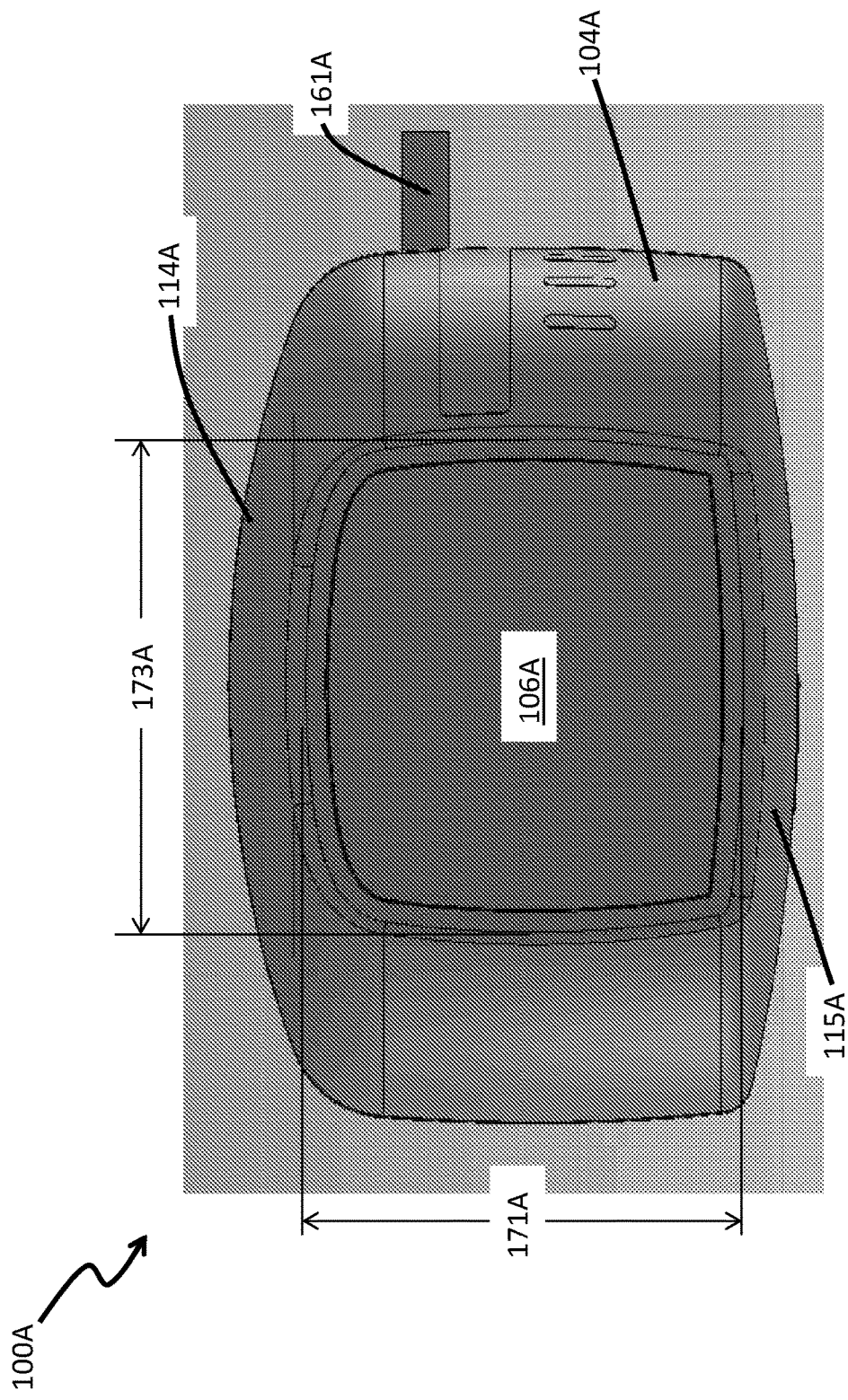
FIG. 4K is a bottom view of the TNP system of FIG. 4A.

FIG. 4K depicts in a bottom view of the TNP system 100A shown in FIG. 4J. The base 106A has a substantially rectangular form and bulges slightly toward the left face and toward the right face, as shown in FIG. 4K. The base 106A can have a base width 171A that defines the distance the base 106A extends between the right face 114A and the left face 115A of the TNP system 100A. The base 106A can have a base length 173A that defines the distance the base 106A extends perpendicular to the base width 171A. The TNP system 100A can be characterized by a base width ratio that is defined as the ratio of the base width 171A to the overall width 141A. In the illustrated embodiment, the TNP system has a base width ratio of about 0.76. In some embodiments, the TNP system 100A can have a base width ratio of about: 0.40, 0.60, 0.70, 0.80, 0.90, or a value between any of these aforementioned values. The TNP system 100A can be characterized by a base length ratio that is defined as the ratio of the base length 173 to the overall diameter 126A. In the illustrated embodiment, the TNP system has a base length ratio of about 0.56. In some embodiments, the TNP system 100A can have a base length ratio of about: 0.20, 0.40, 0.50, 0.60, 0.80, or a value between any of these aforementioned values.

Figure 5:
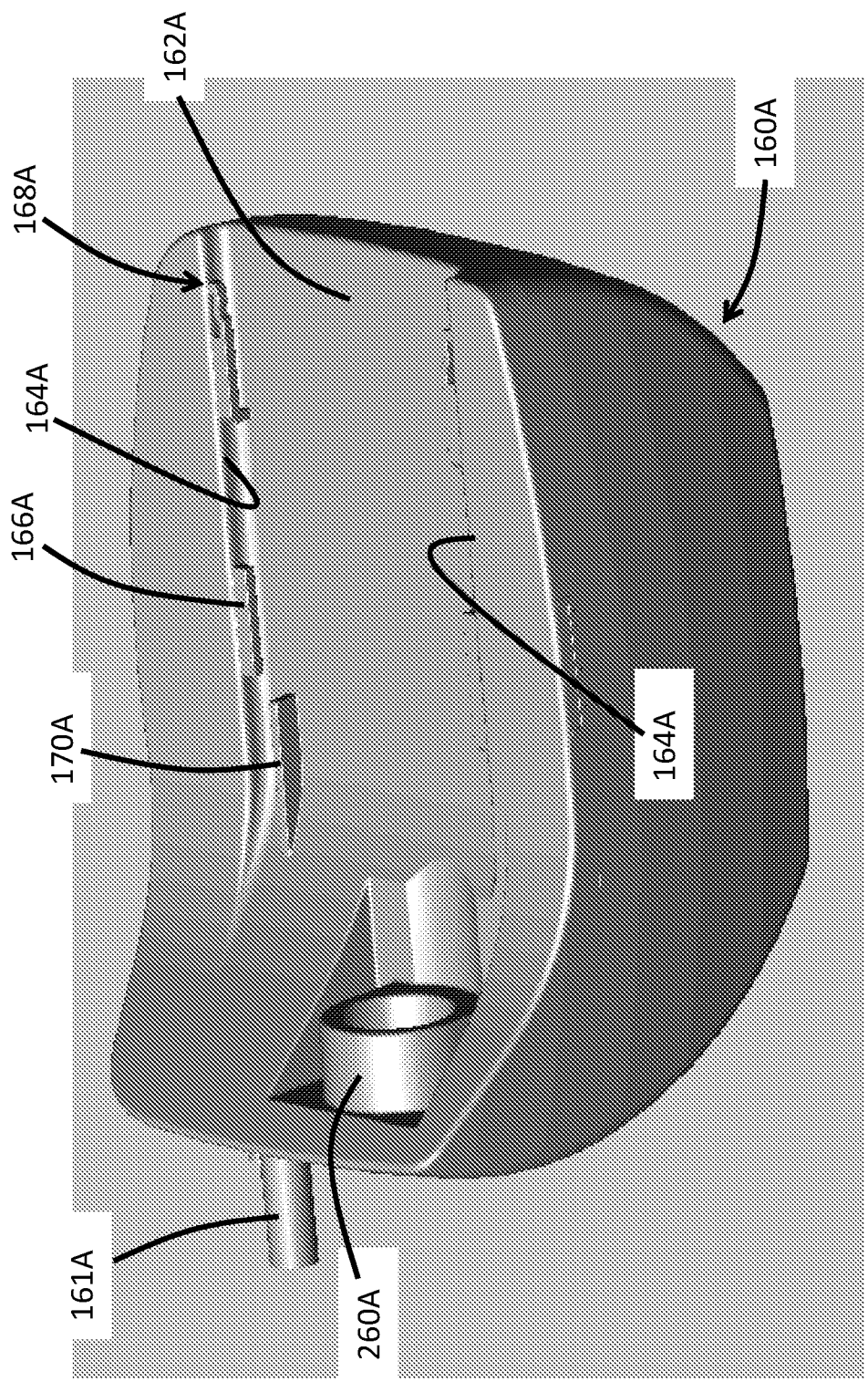
FIG. 5 is a top perspective view of the canister of FIG. 4A.
Figure 6:
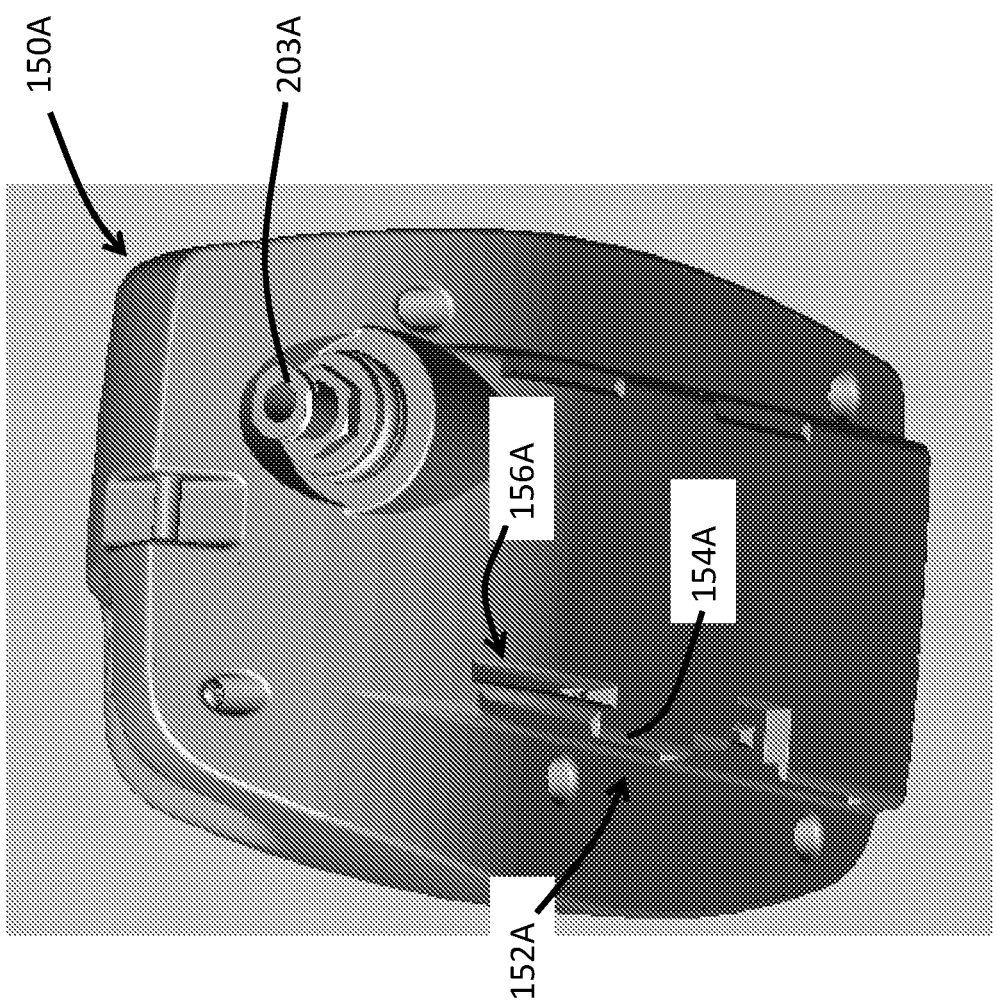
FIG. 6 is a bottom perspective view of the pump assembly of FIG. 4A.

FIG. 5 is a top perspective view of the canister 160A shown in FIG. 4A. FIG. 6 is a bottom perspective view of the pump assembly 150A shown in FIG. 4A. Referring to FIG. 5, the canister 160A can include a canister connector 260A that is adapted to connect with the connector port 203A of the pump assembly 150A. In the illustrated embodiment, the canister connector 260A is integral with a housing 163A of the canister 160A. In some arrangements, the canister connector 260A can be attached to the canister housing 163 by an intermediate structure, such as a length of tubing. The canister 160A can be arranged so that wound exudate is drawn into the canister 160A through the inlet 161A when a negative pressure is applied to the canister connector 260A.

The canister 160A can include one or more features that help secure the canister 160A to the pump assembly 150A. For example, the canister 160A can have a recessed bed 162A that is interposed between two opposing sidewalls 164A, as shown in FIG. 5. One or more securement tabs 166A can extend from one or both of the sidewalls 164A. The securement tabs 166A can be adapted to be received into corresponding slots 152A (shown in FIG. 6) on the pump assembly 150A. The slots 152A can be "L"-shaped to allow the tab 166A to be inserted into the slot 152A in a first direction and then slid in a second direction that is substantially perpendicular to the first direction to align the tab 166A with an overhang 154A (shown in FIG. 6). The overhang 154A can prevent the tab 166A from exiting the slot 152A in the first direction. The securement tab 166A can include a locking clip 168A. The locking clip 168A can be adapted to prevent the canister 160A from being disengaged from the pump assembly 150A without the locking clip 168A first being disengaged. The orientation of the tabs and slots can be reversed. For example, in certain arrangements the pump assembly 150A can have a securement tab that interlocks with a slot that is disposed on the canister 160A.

With continued reference to FIG. 5, the canister 160A can include a fin 170A that extends from the bed 162A of the canister 160A. The fin 170A can be arranged so that when the canister 160A is attached to the pump assembly 150A the fin 170A is received into a recess 156A (shown in FIG. 6) disposed on the pump assembly 150A. The recess 156A can include a switch 158A (shown in FIG. 7B) that is actuated when the fin 170A is received into the recess 156A. In this way, the switch 158A can be actuated by the fin 170A when the pump assembly 150A is connected to a canister 160A.

Figure 7A:
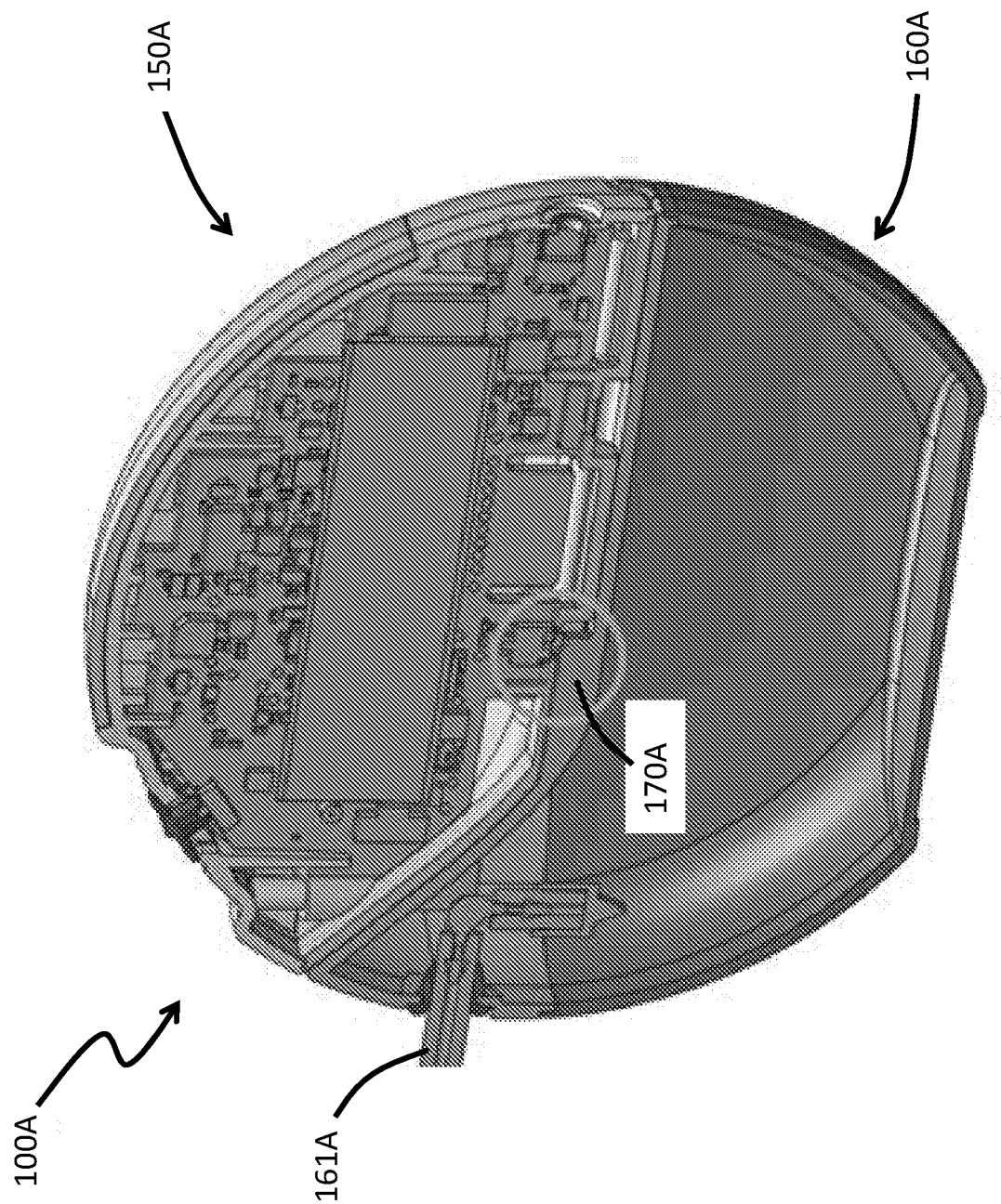
FIG. 7A is a cross-sectional side view of the TNP system of FIG. 4A.
Figure 7C:
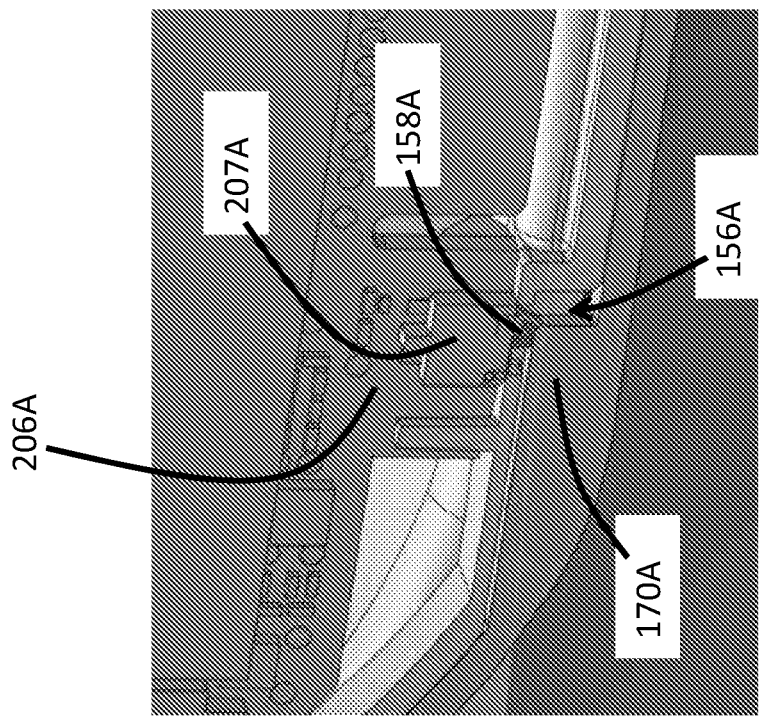
FIG. 7C is a close up view of the switch of FIG. 7A after the switch is pushed upward by the canister.
Figure 7B:
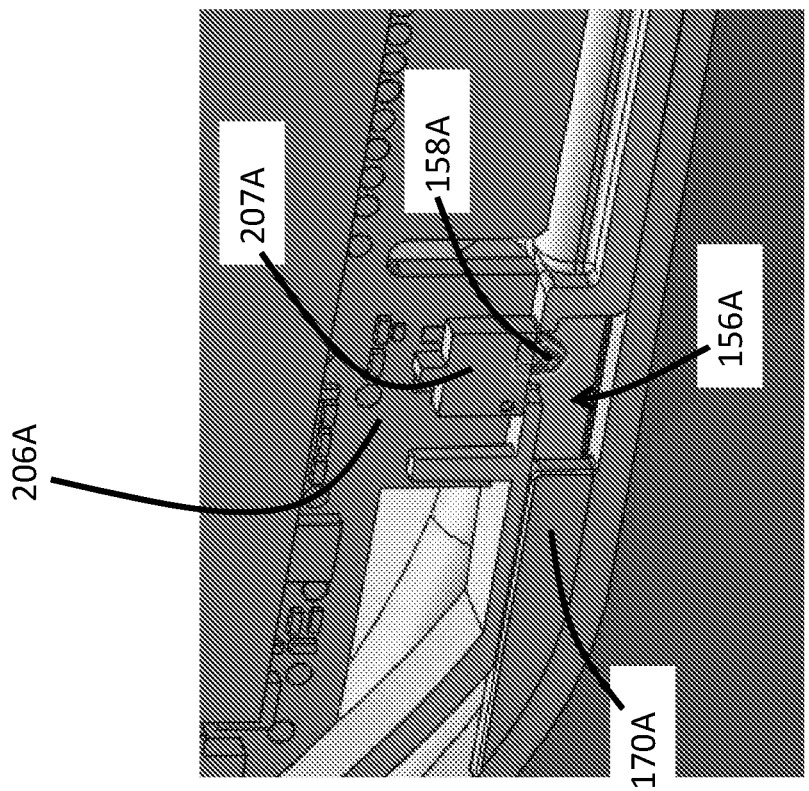
FIG. 7B is a close up view of the switch of FIG. 7A before the switch is contacted by the canister.

FIG. 7A is a cross-sectional side view of the TNP system 100A shown in FIG. 4A. FIGS. 7B and 7C show a close up view of the switch 158A that is disposed within the recess 156A of the pump assembly 150A. The switch 158A can have a first position corresponding to a first state of the switch (e.g., unactuated) and a second position corresponding to a second state of the switch (e.g., actuated). The pump assembly 150A (e.g., the control board 206) can detect the configuration of the switch 158A and adjust one or more operational parameters of the pump assembly 150A based on the detected configuration of the switch 158A. In some arrangements, the canister 160A deactivates the switch 158A when the canister 160A is connected to the pump assembly 150A. In some arrangements, the canister 160A activates the switch 158A when the canister 160A is connected to the pump assembly 150A. In certain arrangements, the switch 158A does not have an unactuated state but rather toggles from a canister position to a canisterless position based on whether the switch 158A is contacted by a portion of the canister 160A that is attached to the pump assembly 150A. FIG. 7B shows the switch 158A in an unactuated position in which the switch 158A extends into the recess 156A. FIG. 7C shows that as the fin 170A slides into the recess 156A, the fin 170A can move the switch 158A from the unactuated position to an actuated position. In the illustrated embodiment, the switch 158A moves toward the pump assembly 150A as the switch 158A moves from the unactuated position to the actuated position. The control board 206A can be configured to detect whether the switch 158A is in the actuated or unactuated position. For example, movement of the switch 158A from the unactuated position to the actuated position can close an electrical circuit within a subassembly 207A of the control board 206A.

The fin 170A and the canister connector 260A can be arranged so that when the canister 160A is attached to the pump assembly 150A, the fin 170A actuates the switch 158A before the canister connector 260A forms a fluidic seal with the connector port 203A of the pump assembly 150A. The fin 170A and the canister connector 260A can be arranged so that when the canister 160A is detached from the pump assembly 150A, the fluidic seal between the canister connector 260A and the connector port 203A is broken before the switch 158A moves from the actuated to the unactuated position. The pump assembly 150A can be further adapted to operate in a canister operational mode when the switch 158A is actuated and to operate in a canisterless operational mode when the switch 158A is unactuated. In this way, the system 10A can be arranged to avoid the pump assembly 150A running in canisterless mode when a canister 160A is sealingly attached to the pump assembly 150A. If the seal between the canister connector 206A and the connector port 203A were to be broken after the switch 158A moves from the actuated to the unactuated position, this would make it possible for the system 100A to run in a canisterless mode while the canister is still connected.

In other alternative arrangements, the fin 170A and the canister connector 260A can be arranged so that when the canister 160A is attached to the pump assembly 150A, the canister connector 260A forms a fluidic seal with the connector port 203A of the pump assembly 150A before the fin 170A actuates the switch 158A. In some arrangements, the fin 170A and the canister connector 260A can be arranged so that when the canister 160A is attached to the pump assembly 150A, the canister connector 260A forms a fluidic seal with the connector port 203A of the pump assembly 150A at the same time as the fin 170A actuates the switch 158A.

Figure 8A:
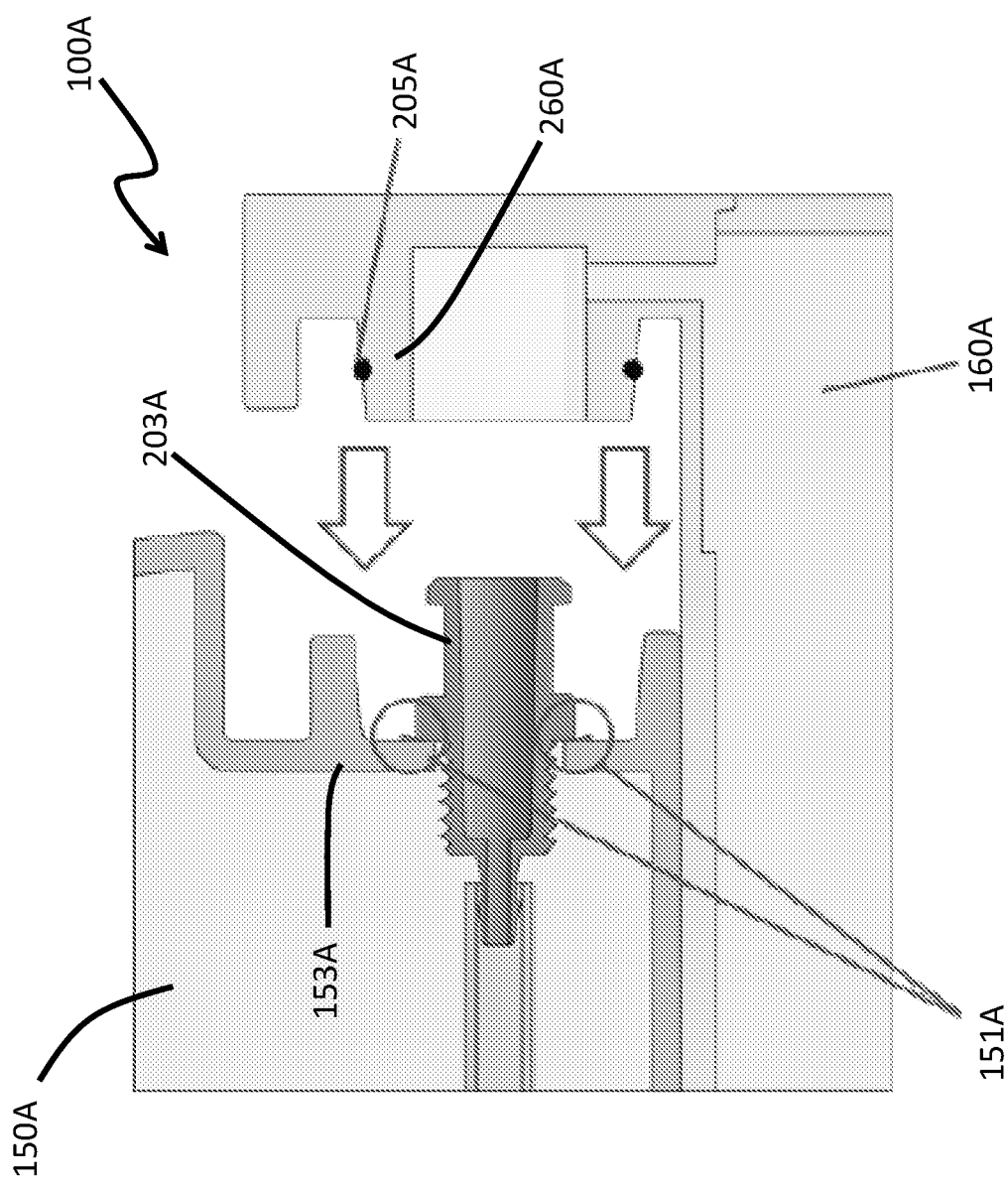
FIG. 8A is a cross-sectional side view of an embodiment of the TNP system illustrating a connection between the canister and the pump assembly.

FIG. 8A is a cross-sectional side view of an embodiment of the TNP system 100A illustrating a connection between the canister 160A and the pump assembly 150A. The canister 160A can be attached to the pump assembly 150A by pushing the canister connector 260A of the canister 160A onto the connector port 203A of the pump assembly 150A. The pump assembly 150A can include a connector seal 151A disposed between the connector port 203A and the housing 153A of the pump assembly 150A. The connector seal 151A can prevent liquid or dirt from passing between the connector port 203A and the housing 153A, thereby preventing liquid and/or waste from contacting internal components (e.g., the control board 206A) of the pump assembly 150A. The canister connector 260A can include a seal 205A. As described in more detail below, the seal 205A can form a sealed volume between the canister connector 260A and the housing 153A of the pump assembly 150A, thereby by allowing a negative pressure to be communicated from the connector port 205A to the interior space of the canister 160A. In the illustrated embodiment, the seal 205A is an O-ring seal that is seated in a groove that surrounds the canister connector 260A. The seal 205A can be adapted to form a liquid and/or gas tight seal with the portion of the pump assembly housing 153A that surrounds the connector port 203A.

Figure 8C:
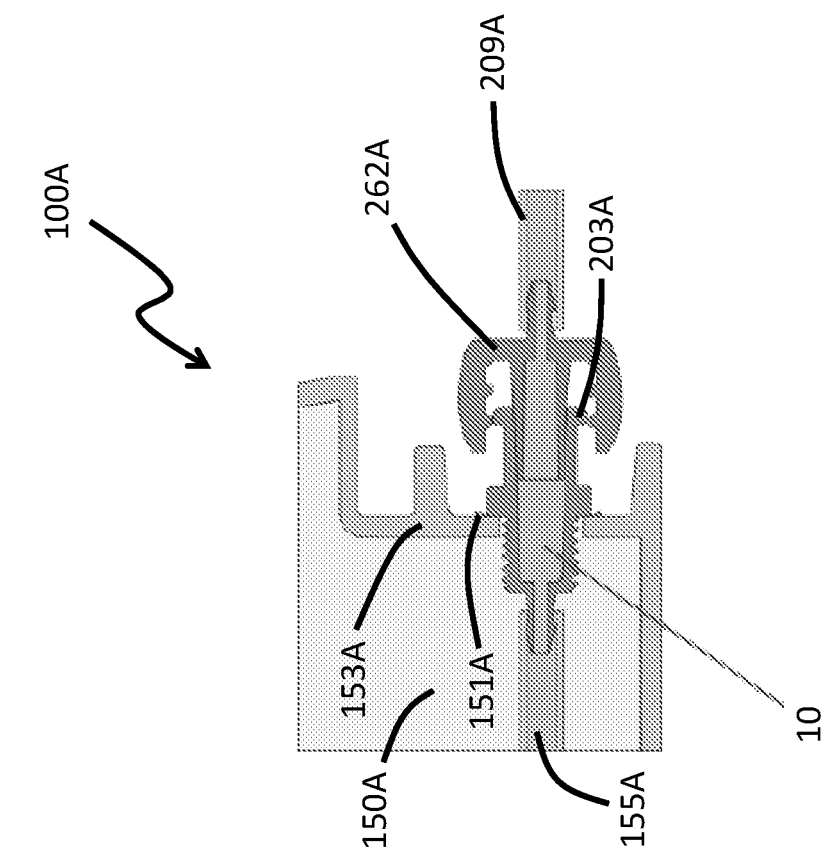
FIG. 8C is a cross-sectional side view of a canisterless connector attached to the pump assembly of FIG. 8A.
Figure 8B:
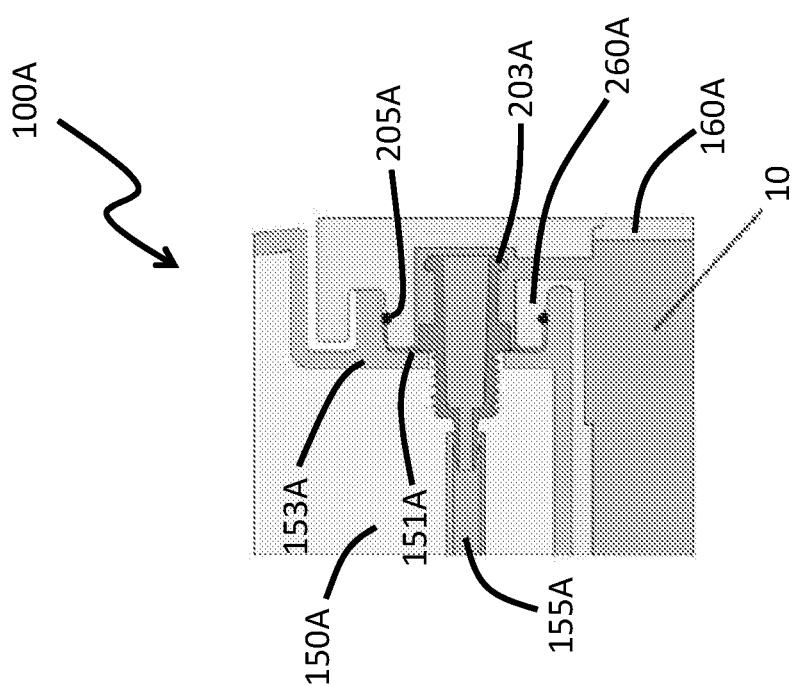
FIG. 8B is a cross-sectional side view of the embodiment of FIG. 8A with the canister attached to the pump assembly.

FIG. 8B is a cross-sectional side view of the canister 160A attached to the pump assembly 150A. The seal 205A of the canister connector 260A forms a gas tight seal with the portion of the housing 153A of the pump assembly 150A that surrounds the connector port 203A, thereby forming a sealed volume 10 that extends from an interior space of the canister 160 through the connector port 203A and into the internal tubing 155A of the pump assembly 150A The seal 205A allows a negative pressure generated by the pump assembly 150A to be communicated to the interior space of the canister 160A.

FIG. 8C is a cross-sectional side view of a canisterless connector 262A attached to the pump assembly 150A The canisterless connector 262A can be an integral part of a dressing or can be connected to the dressing by an intermediate structure, such as a piece of tubing. In the illustrated embodiment, the canisterless connector 262A is connected to a dressing (not shown) through a piece of tubing 209A. In the illustrated embodiment, a central portion of the canisterless connector 262A is inserted into the connector port 203A to form a sealed space 10 that extends from the internal tubing 155A of the pump assembly 150A through the piece of tubing 209A. The canisterless connector 262A allows a negative pressure generated by the pump assembly 150A to be communicated to the wound through the tubing 209A. As shown in FIGS. 8B and 8C, the pump assembly 150A can have a connector port 203A that uses different surfaces to form a seal with a canister 160A or a canisterless connector 262A. In the illustrated embodiment, the connector port 203A uses a first sealing surface to form a seal with a canister 160A (FIG. 8B) and a second sealing surface to form a seal with the canisterless connector 262A (FIG. 8C), with the first sealing surface being disposed radially outward of the second sealing surface.

As discussed in more detail below, the pump assembly 150A can include one or more switches (see, e.g., FIGS. 16A-24) in addition to the switch 158A that is disposed within the recess 156A of the pump assembly 150A. The one or more additional switches can be adapted to be actuated when the canister connector 260A is connected to the pump assembly 150A. In some arrangements, the pump assembly 150A can include one or more additional switches (see, e.g., FIGS. 16A-24) that are actuated when the canisterless connector 262A is connected to the pump assembly 150A. In certain arrangements, the pump assembly 150A can include at least one additional switch that is actuated when the connector port 203A is connected to one but not to the other of a canister connector 260A and a canisterless connector 262A. In some arrangements, the at least one additional switch can be disposed at the connector port 203A.

FIGS. 9A-C show an embodiment of the TNP system 100B that has a disc-shaped form when the canister 160B is attached to the pump assembly 150B. The connector port 203B can be disposed on an edge of the disc-shaped pump assembly 150B, as shown in FIG. 9A. The canister 160B can include a rail 172B disposed on a medial portion of the canister 160B. The pump assembly 150B can include a recess (not shown) that is adapted to slide onto the rail 172B to allow the canister 160B to be attached to the pump assembly 150B. The canister connector 260B of the canister 160B can align with the connector port 203B of the pump assembly 150B when the canister 160B is attached to the pump assembly 150B. The connector port 203B can be adapted to form a gas tight seal with a canisterless connector 262B to allow a negative pressure generated by the pump assembly 150B to be communicated to a wound dressing (not shown) through tubing 209B. FIG. 9B shows a partial rear view of the TNP system 100B with a canister 160B attached to the pump assembly 150B. FIG. 9C shows a partial front view of the TNP system 100B shown in FIG. 9B.

Figure 10:
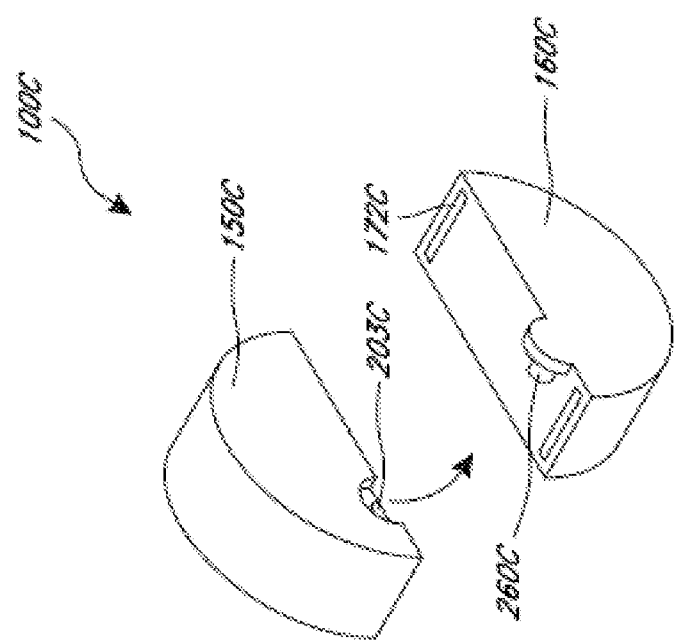
FIG. 10 shows a front perspective view of an embodiment of the TNP system that has a disc-shaped form when the canister is attached to the pump assembly.

FIG. 10 shows an embodiment of the TNP system 100C that has a disc-shaped form when the canister 160C is attached to the pump assembly 150C. The canister 160C can be assembled onto the pump assembly 150C by sliding the canister 160C relative to the pump assembly 150C in a direction that is substantially perpendicular to the faces of the disc-shaped form of the assembled TNP system 100C. The connector port 203C can be disposed on a face of the disc-shaped pump assembly 150C, as shown in FIG. 10. The canister 160C can include one or more rails 172C that are disposed substantially perpendicular to the face of the canister 160C. The pump assembly 150C can include one or more recesses (not shown) that are adapted to slide onto the rails 172C to allow the canister 160C to be attached to the pump assembly 150C. The canister connector 260C of the canister 160C can align with the connector port 203C of the pump assembly 150C when the canister 160C is attached to the pump assembly 150C. In the illustrated embodiment, the pump assembly 150C has a semi-circular profile with the connector port 203C disposed off-center.

Figure 11:
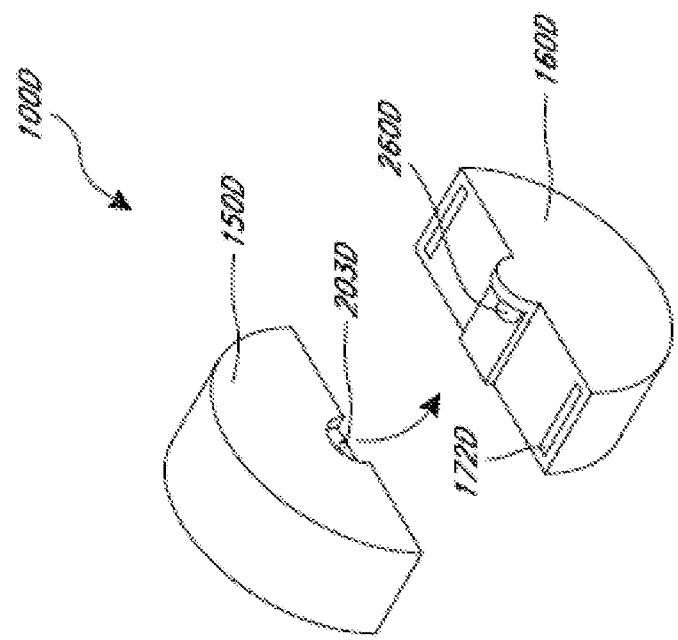
FIG. 11 shows a front perspective view of an embodiment of the TNP system that has a disc-shaped form when the canister is attached to the pump assembly.

FIG. 11 shows an embodiment of the TNP system 100D that is similar to the system 100 of FIG. 10 except that the connector port 203C is disposed substantially at the center point of the semi-circular pump assembly 150D.

Figure 12B:
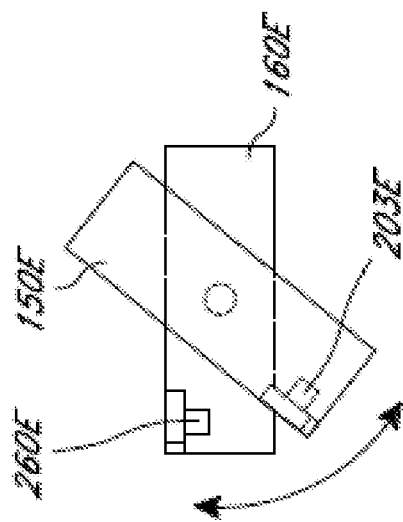
FIG. 12B is a top view of the TNP system of FIG. 12A illustrating the twisting action that connects and disconnects the canister and pump assembly.
Figure 12A:
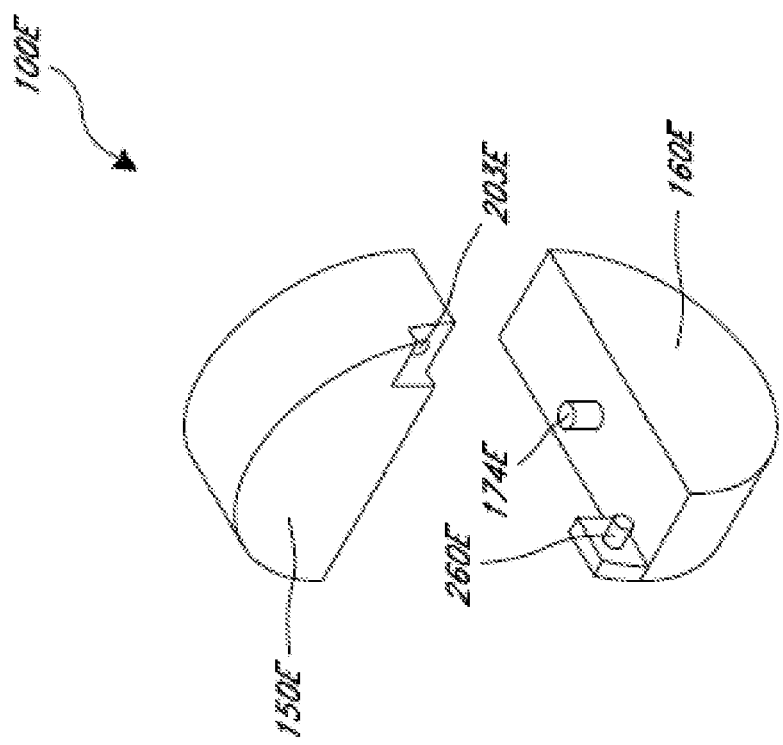
FIG. 12A shows an embodiment of a TNP system with a canister that is attached to the pump assembly by a twisting action.

FIGS. 12A and 12B show an embodiment of a TNP system 100E with a canister 160E that is attached to the pump assembly 150E by a twisting action. The canister 160E can have a post 174E that is received into a recess (not shown) on the pump assembly 150E. After the post 174E is seated in the recess of the pump assembly 150E, the pump assembly 150E can be rotated relative to the canister 160E to bring the connector port 203E into alignment with the canister connector 260E. FIG. 12B is a top view of the TNP system 100E after the pump assembly 150E and before the pump assembly 150E has been rotated to connect the connector port 203 with the canister connector 260E.

FIGS. 13A-E show an embodiment of a TNP system 100F with a pump assembly 150F that includes a rotatable connector port 203F, The connector port 203F can be adapted to rotate between a first and a second position. As described in more detail below, the connector port 203F can be adapted to connect with a canister connector 260F when the connector port 203F is in the first position. The connector port 203F can be adapted to connect with a canisterless connector 262F when the connector port 203F is in the second position.

FIG. 13A shows the pump assembly 150F with the connector port 203F in the first position. As shown in FIG. 13A, the connector port 203F can be substantially parallel with the face of the pump assembly 150F when the connector port 203F is in the first position. FIG. 13B shows the pump assembly 150F with the connector port 203F in a second position. As shown in FIG. 13B, the connector port 203F can be substantially perpendicular with the face of the pump assembly 150F when the connector port 203F is in the second position. FIG. 13C illustrates the connection of the pump assembly 150F with the canister 160F. The connector port 203F is in the first position and substantially parallel with the face of the pump assembly 150F. The canister 160F can include a post 174F that can seat into a recess 176F of the pump assembly 150F to help align the connector port 203F with the canister connector 260F. FIG. 13D illustrates the TNP system 100F with the pump assembly 150F attached to a canister 160F. FIG. 13E illustrates that the TNP system 100F can be attached to a canisterless connector 262F when the connector port 203F is rotated to the second position.

Figure 13F:
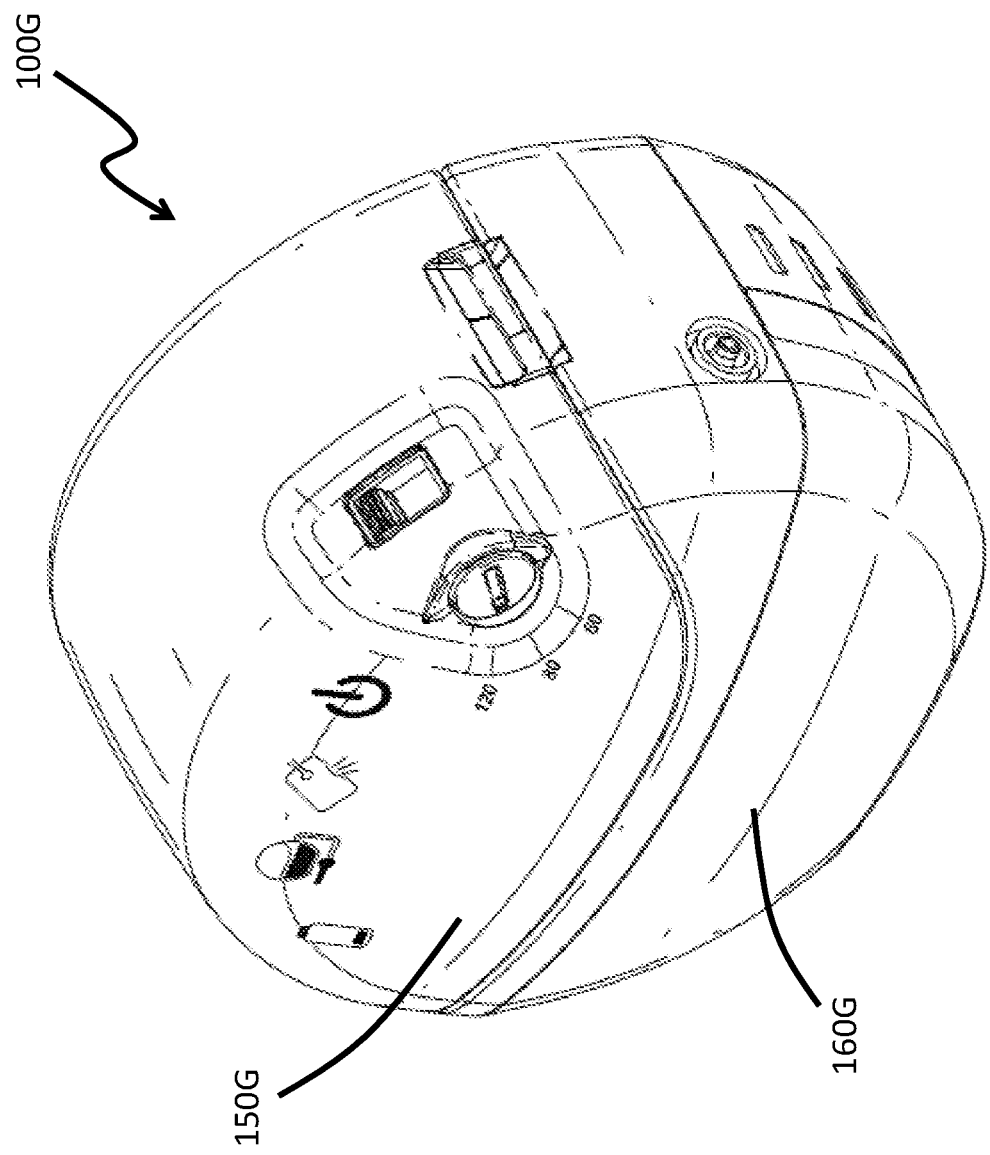
FIG. 13F shows an embodiment of a TNP system with a canister attached to the pump assembly.

FIG. 13F shows an embodiment of a TNP system 100G that is similar to the TNP system 100 described herein except as described differently below. The TNP system 100G includes a pump assembly 150G and a canister 160G that are similar to the pump assembly 150 and canister 160 described herein except as described differently below.

Figure 13G:
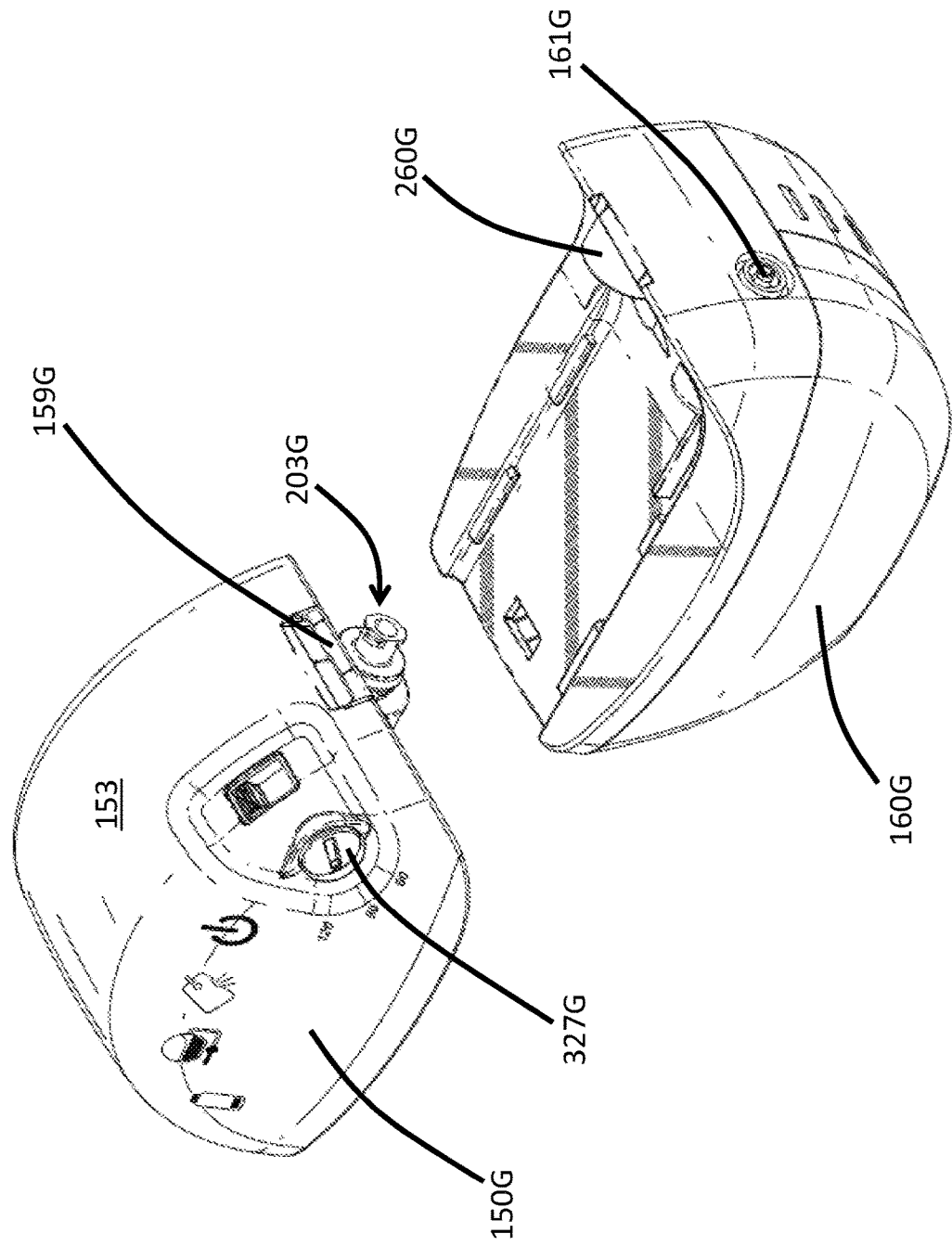
FIG. 13G shows the TNP system of FIG. 13F with the canister detached from the pump assembly.

FIG. 13G shows the TNP system 100G can have a pump assembly 150G that is adapted to be slidably coupled to a canister 160G. As described above, the pump assembly 150G can have a connector port 203G that is adapted to connect to a connector 201 (shown schematically in FIGS. 3A-B). The connector 201 can be a canister connector 260 or a canisterless connector 262, as discussed above. The connector port 203G can be fluidically connected to a negative pressure source (e.g., vacuum pump) housed within the pump assembly 150G. The connector port 203G can establish a flow path between the negative pressure source of the pump assembly 150G and the connector 201 that is connected to the connector port 203G. The pump assembly 150G can provide negative pressure to a canister connector 260G or a canisterless connector 262 that is attached to the connector port 203G. The canister 160G can have a canister connector 260G that fluidically connects to the connector port 203G when the pump assembly 150G is slidably mounted onto the canister 160G. The canister 160G can have an inlet 161G through which wound exudate enters the canister 160G when negative pressure is applied to the canister 160G through the canister connector 260G.

With continued reference to FIG. 13G, the pump assembly 150G can include a dial 327G that allows pressure selection on the pump assembly 150G. The magnitude of the negative pressure supplied by the pump assembly 150G can be adjusted by turning the dial 327G. The dial 327G can be adapted to turn to two or more discreet settings. For example, the dial 327G can have three discreet settings that allow the negative pressure provided by the pump assembly 150G to be set to one of three settings (e.g., −60 mmHg, −80 mmHg, and −120 mmHg). The pump assembly 150G can include a bar 159G that can be used as an anchoring site for a strap or clasp, thereby allowing the pump assembly 150G to be suspended from a strap that is attached to the bar 159G. When the canister 160G and the pump assembly 150G are connected together, a ramped portion of the top surface of the canister 160G can form an overhang that is supported on an inclined portion of the bottom surface of the pump assembly 150G, thereby enhancing retention of the canister 160G on the pump assembly 150G when the pump assembly 150G is suspended from the bar 159G. The pump assembly 150G can include one or more icons on the housing 153G of the pump assembly 150G. The icons can be backlit by a light source that is disposed within the housing 153G of the pump assembly 150G.

Figure 13H:
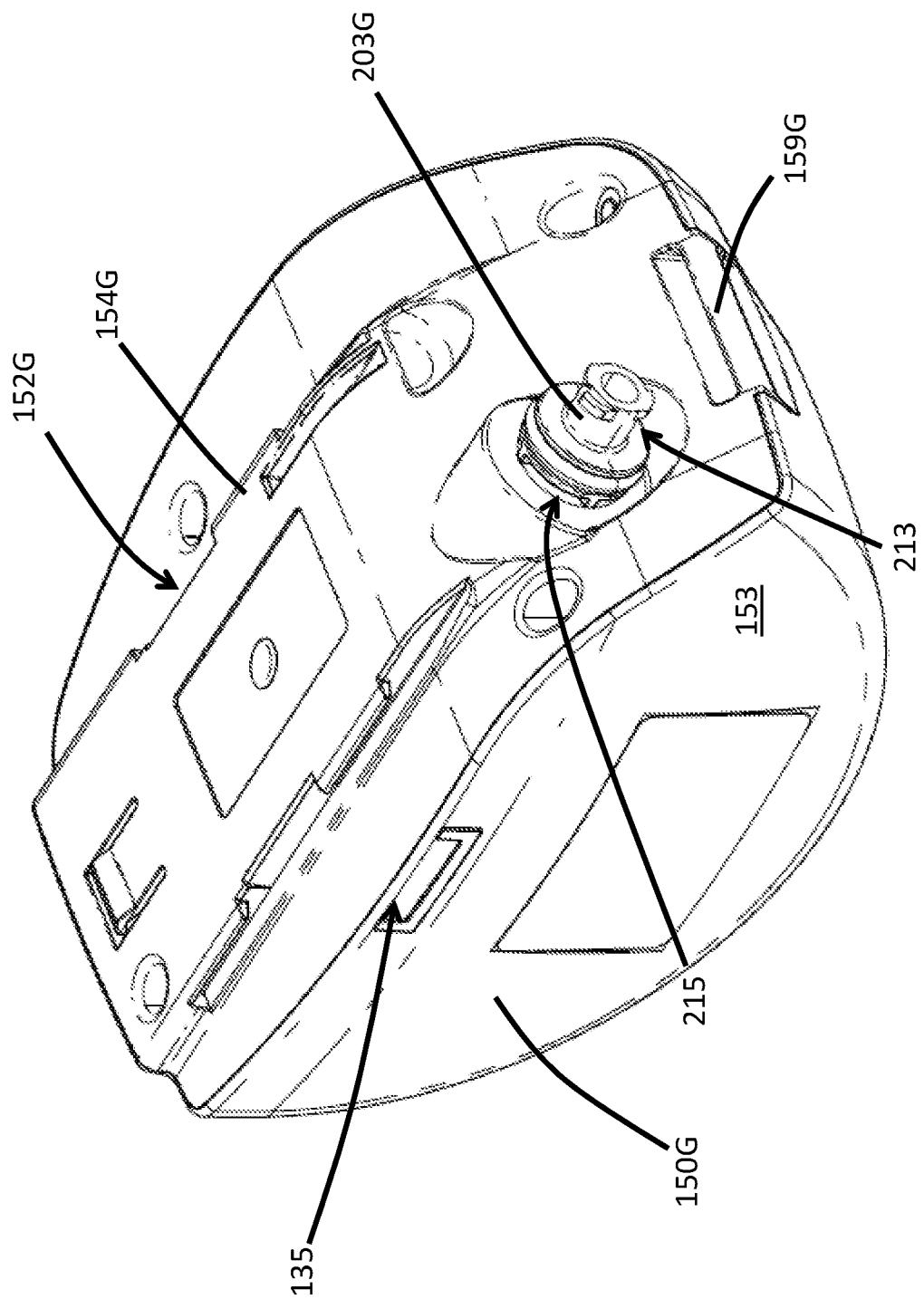
FIG. 13H shows the canister-facing surface of the pump assembly of FIG. 13G.

FIG. 13H illustrates the features on the canister-facing surface of the pump assembly 150G. The canister-facing surface of the pump assembly 150G can include slots 152G and overhangs 154G similar to the slots 152A and overhangs 154A described above with regard to FIG. 6. The slots 152G can receive corresponding securement tabs 166G (shown in FIG. 13J) disposed on the canister 160G, thereby allowing the pump assembly 150G to be slidably mounted onto the canister 160G, as described above with regard to FIGS. 5 and 6. As shown in FIG. 13H, the pump assembly 150G can include an indicator mark 135 disposed on the pump housing 153. The indicator mark 135 can be aligned with a corresponding indicator mark 137 disposed on the canister 160G. The indicator marks 135, 137 can be arranged to facilitate the coupling of the pump assembly 150G onto the canister 160G. The indicator marks 135, 137 can be arranged to assist properly aligning of the securement tabs 166G to allow the securement tabs 166G to enter the slots 152G of the pump assembly 150G. In the illustrated embodiment the indicator marks 135, 137 are "U"-shaped. The indicator marks 135, 137 can be arranged such that the securement tabs 166G are aligned to enter the slots 152G when the front vertical portion of the indicator mark 135 of the pump assembly 150G is aligned with the rear vertical portion of the indicator mark 137 of the canister 160G. The pump assembly 150G can be slid forward relative to the canister 160G to align the front vertical portions of the indicator marks 135, 137 with one another, thereby coupling the connector port 203G into the canister connector 260G and vertically aligning the securement tabs 166G with the overhangs 154G such that the pump assembly 150G and the canister 160G held together.

As discussed above with regard to the connector port 203A shown in FIGS. 8B and 8C, the connector port 203G can be adapted to form a fluidic seal with either a canister connector 260 or a canisterless connector 262. The connector port 203A can have a first sealing surface that forms a fluidic seal with the canisterless connector 262. The connector port 203A can have a second sealing surface that forms a fluidic seal with the canister connector 260. The first and second sealing surfaces can be spaced apart from one another on the connector port 203A. In the embodiment shown in FIG. 13H, the connector port 203G has a tip portion 213 and a base portion 215, with the base portion 215 disposed between the tip portion 213 and the pump housing 153. The tip portion 213 can form a fluidic seal with a canisterless connector 262. In the illustrated embodiment, the tip portion 213 includes a luer lock feature on the end that faces away from the base portion 215. The tip portion 213 can include a tapered shaft that is interposed between the luer lock feature and the base portion 213. The tapered shaft can taper in the direction of the tip portion 213 such that the outer diameter of the tapered shaft decreases along the tapered shaft in the direction from the base portion 215 to the tip portion 213. The tapered shaft can form an interference fit with a female luer fitting that is twisted onto the luer lock feature. The taper of the tapered shaft can be a Morse taper. In some embodiments, the tapered shaft has a taper angle between about 10 and about 10°. In certain variants the tapered shaft has a taper angle of about 5°.

The base portion 215 can include an O-ring that forms a seal with a canister connector 260 into which the connector port 203 is inserted. In some embodiments, the orientation of the connection between the connector port 203G and the canister connector 260 can be flipped. In some variants, the base portion 215 does not have an O-ring and the canister connector 260 can have an O-ring disposed on in inner surface that receives the base portion 215 of the connector port 203G.

Figure 13I:
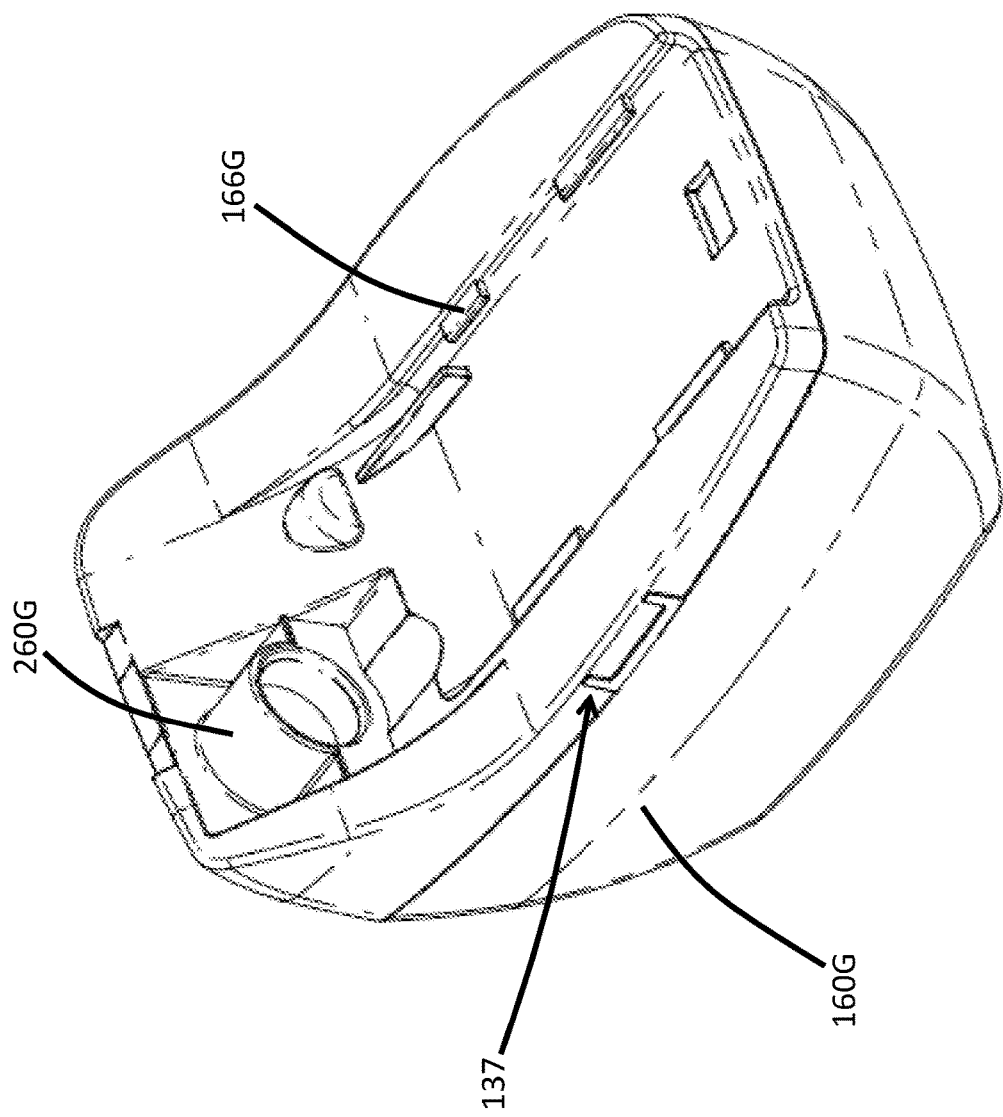
FIG. 13I shows the pump-facing surface of the canister of FIG. 13G.

FIG. 13I illustrates a view of the pump-facing surface of the canister 160G. The canister 160G can include an indicator mark 137 that helps align the securement tabs 166G to allow the pump assembly 150G to be mounted onto the canister 160G, as described above.

Figure 13J:
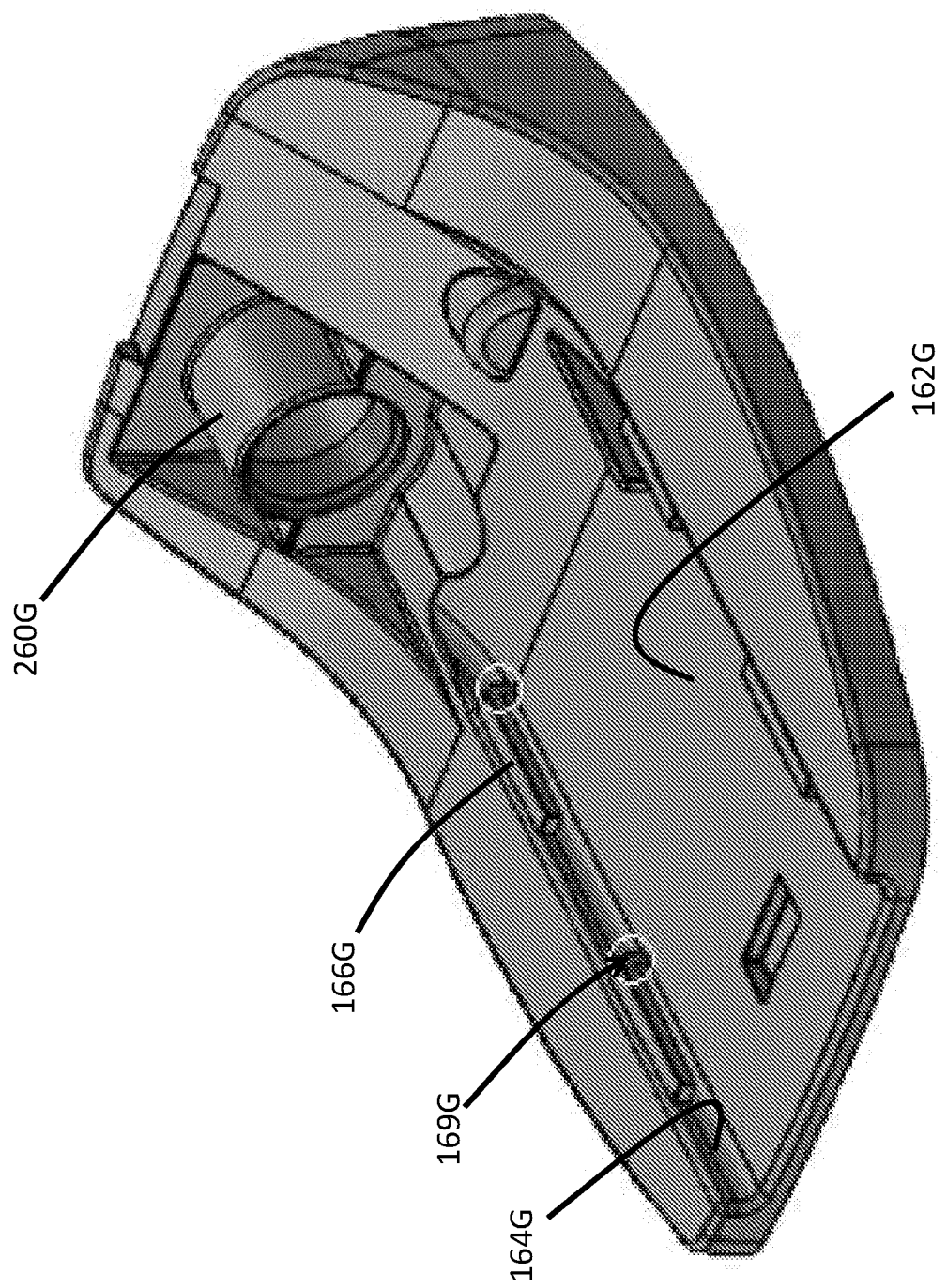
FIG. 13J shows the pump-facing surface of another embodiment of a canister.

FIG. 13J illustrates an embodiment of the pump-facing surface of the canister 160G that has an abutment 169G that extends vertically from the pump-facing surface to connect with the securement tab 166G that extends horizontally from the sidewall 164G. The abutment 169G can act as a hard stop that prevents the pump assembly 150G from being slid off the open end of the bed 162G of the canister 160G, thereby preventing a user from sliding the canister 160G and the pump 150G too far or too quickly relative to one another when decoupling them, which could cause the user to drop the canister 160G or the pump 150G.

Figure 13K:
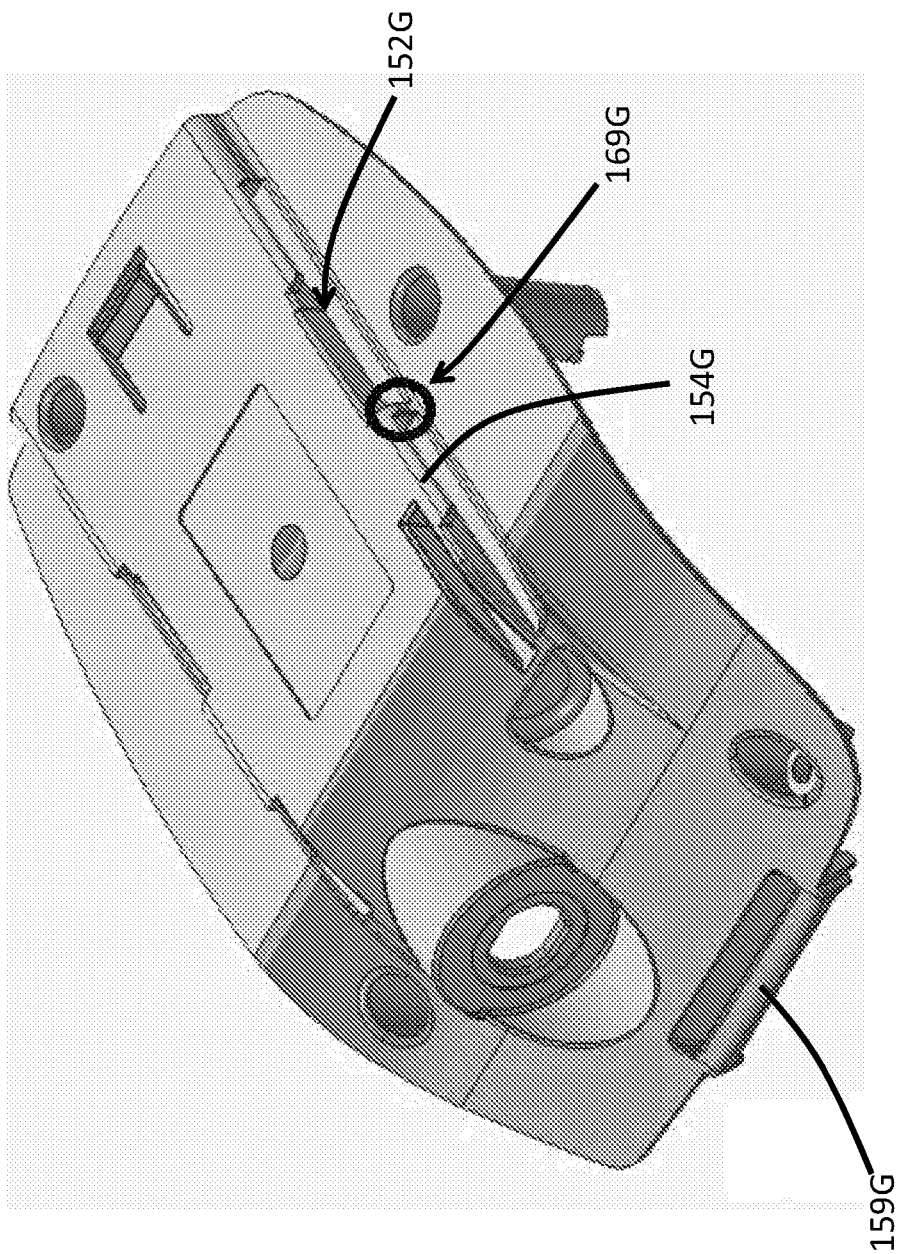
FIG. 13K shows the canister-facing surface of another embodiment of a pump assembly.

FIG. 13K illustrates an embodiment of the canister-facing surface of the pump assembly 150G that has a corresponding abutment 169G that lessens the likelihood of a user over sliding and dropping the pump assembly 150G or the canister 160G when decoupling them from one another.

Figure 13L:
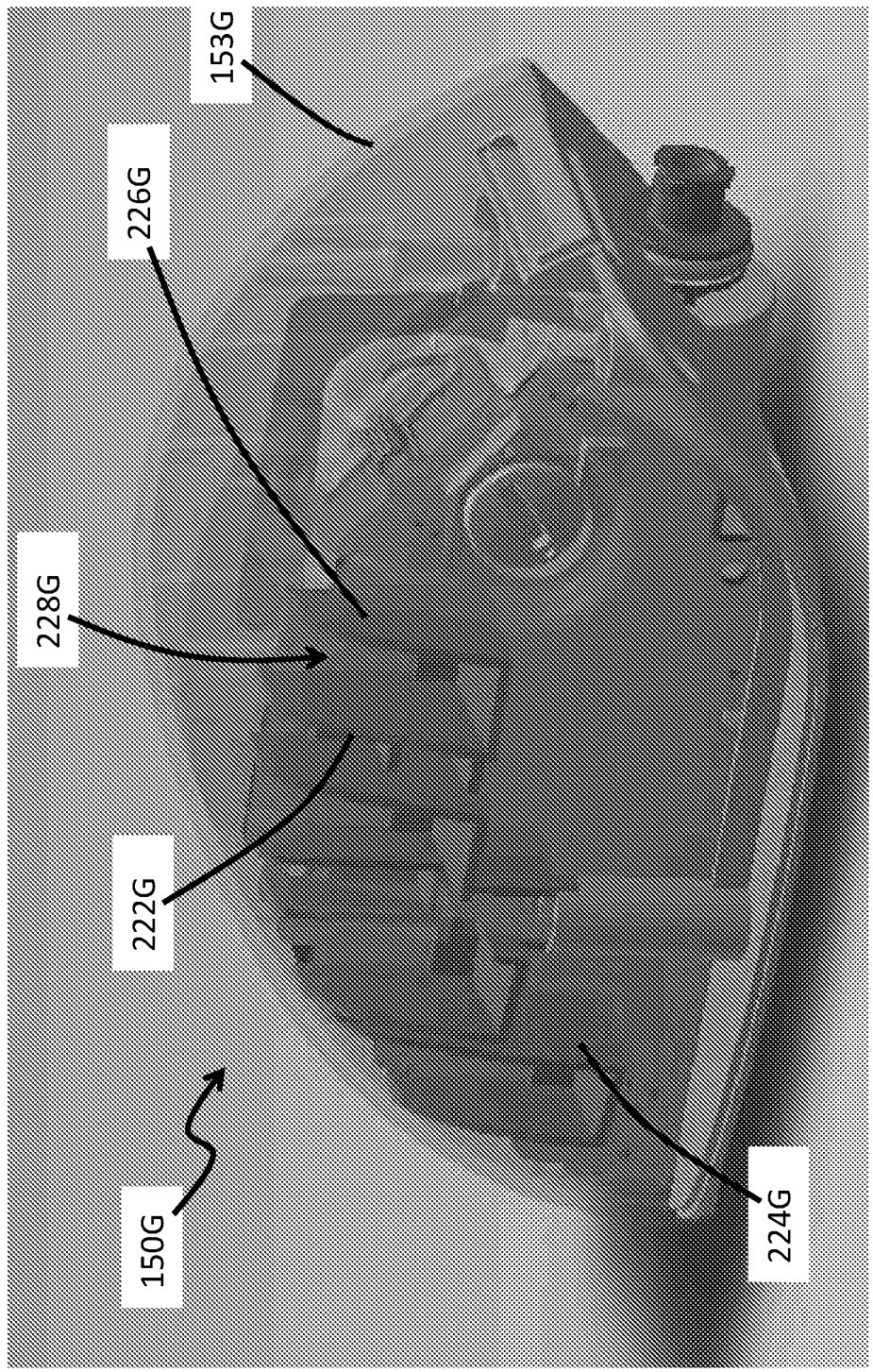
FIG. 13L shows the pump assembly of FIG. 13F with the pump housing rendered transparent to show internal components of the pump assembly.

FIG. 13L illustrates the pump assembly 150G with the pump housing 153G being rendered transparent in order to show some of the internal components of the pump assembly 150G. As shown in FIG. 13L, the pump assembly 150G can include a light guide 224G that is similar to the gates 124 (shown in FIG. 4E) except as differently described below. The light guide 224G can include a plurality of blades 226G that define a plurality of slots 228G between pairs of adjacent blades 226G. The light guide 224G can be fixed to the pump housing 153G so that the slots 228G align with the icons (shown in FIG. 13G) disposed on the pump housing 153G. The blades 226G can be opaque to prevent light from passing through the blade 226, thereby preventing a light source disposed in one slot 228G from illuminating a portion of the housing 153G that covers an adjacent slot 228G. The blades 226G can have a front face 222G that is shaped to match the contour of the inner surface of the pump housing 153G The front face 222G can be shaped so that the light guide 224G is flush against the inner surface of the pump housing 153G. The front face 222G can be shaped to avoid forming gaps between the front face 222G and the inner surface of the pump housing 153G, thereby preventing or reducing light leaking between adjacent slots 228G of the light guide 224G.

In some embodiments, as illustrated in FIG. 13L, a medical device such as a pump assembly 150G as described herein can comprise a housing 153G with an exterior surface having one or more icons, and within the housing 153G is provided a light guide 222G that comprises a plurality of blades 226G and slots 228G between the blades 226G. The light guide 222G and the icons can be arranged such each icon aligns with an individual slot 228G, thereby allowing a light source disposed within a slot 228G to illuminate a single icon.

Figure 13M:
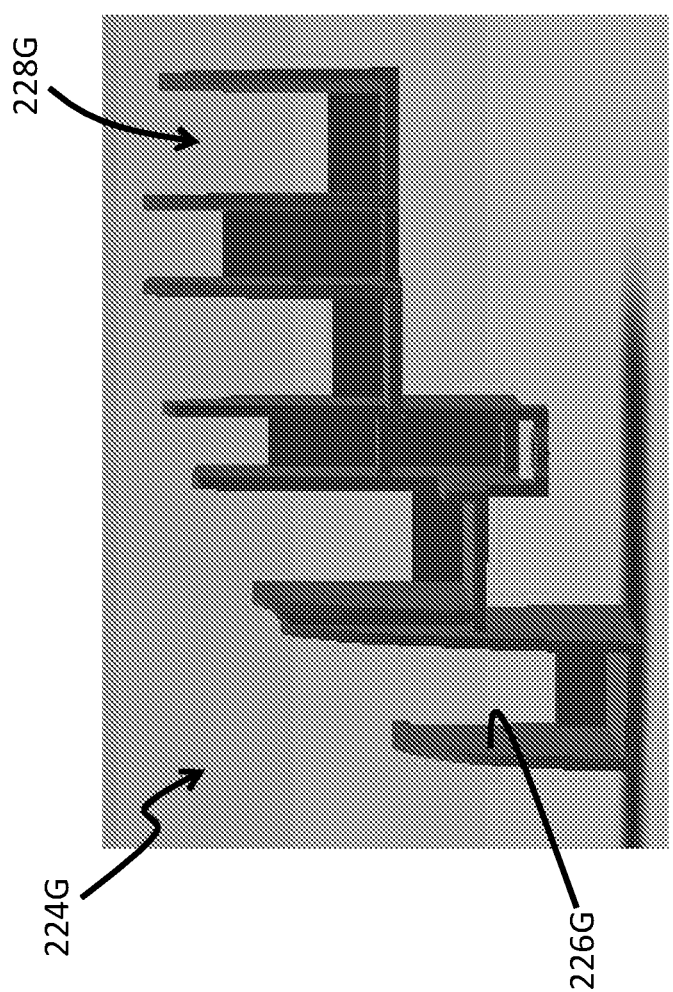
FIG. 13M shows a front view of an embodiment of a light guide for a pump assembly of a TNP system.
Figure 13O:
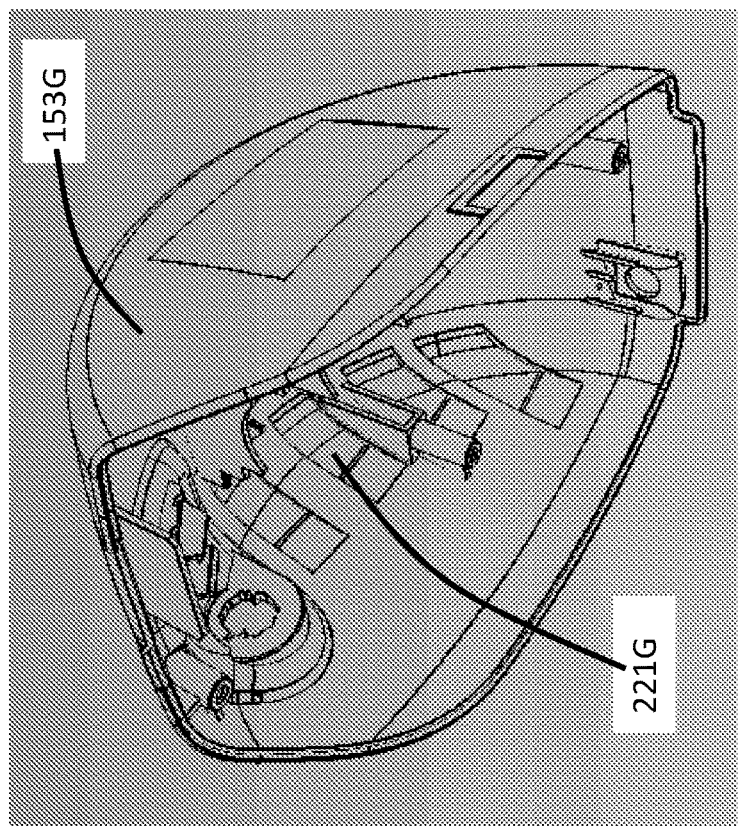
FIG. 13O shows the pump housing of FIG. 13N with the light guide removed.
Figure 13N:
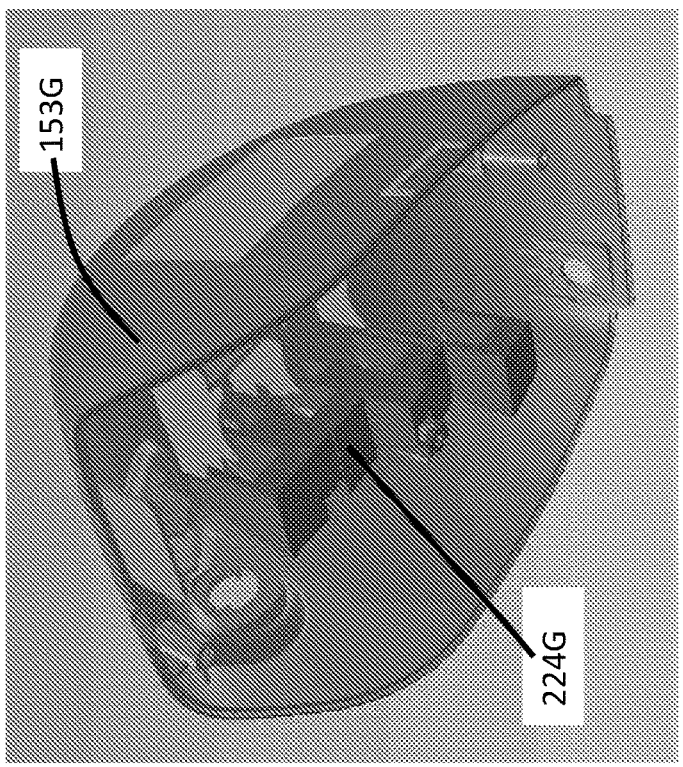
FIG. 13N shows the light guide attached to the pump housing of the pump assembly of FIG. 13L.

FIG. 13M shows a front view of the light guide 224G. FIG. 13N shows the light guide 224G mounted onto the inner surface of the pump housing 153G. FIG. 13O illustrates the interior of the pump housing 153G with the light guide 224G removed in order to show that the inner surface of the pump housing 153G can include thinned portions 221G that enhance the transmission of light through the pump housing 153G. As shown in FIG. 13O, the thinned portions 221G of the pump housing 153G can be recessed relative to surrounding portions of the inner surface of the pump housing 153G. The outer surface of thinned portions 221G can be flush with the outer surface of the pump housing 153G such that the outer surface of the pump housing 153G has a smooth finish, as shown in FIG. 13G.

Figure 13P:
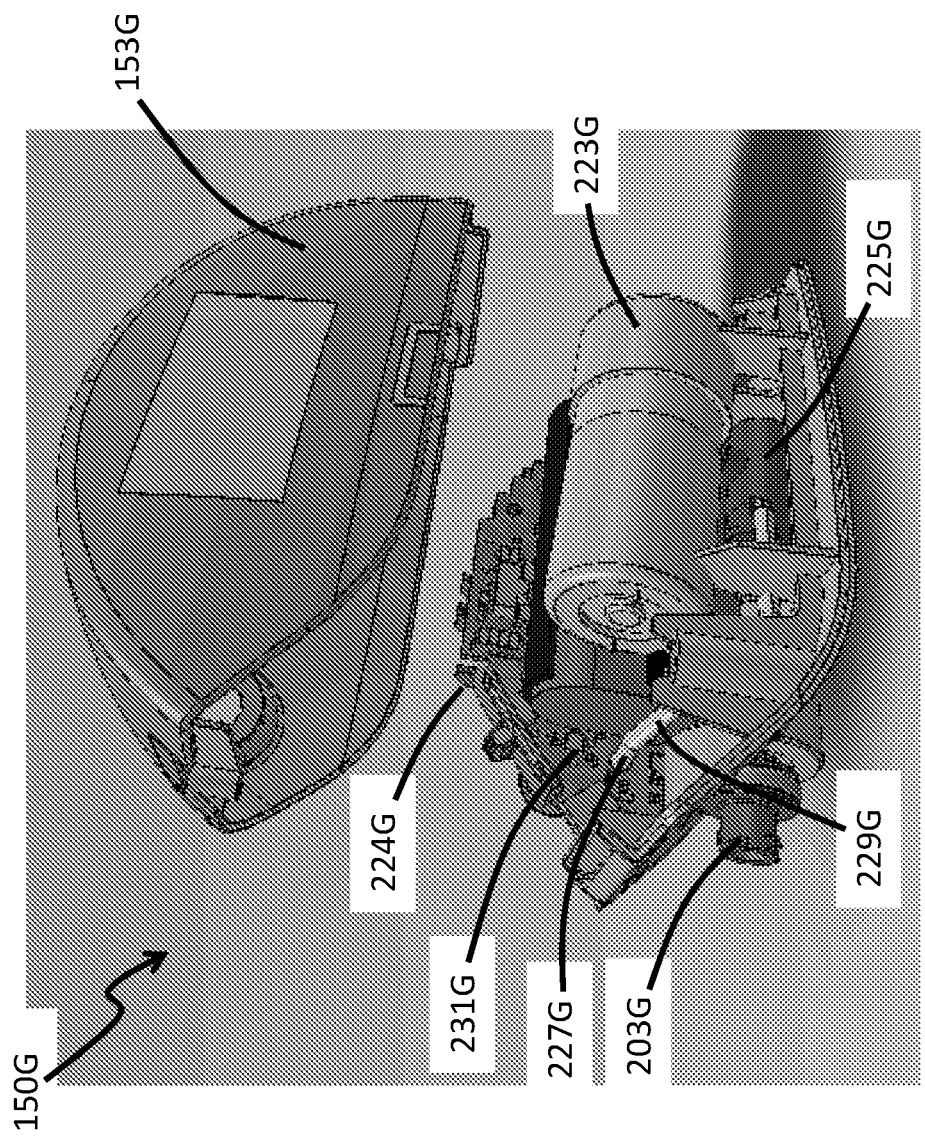
FIG. 13P shows the pump assembly of FIG. 13L with the pump housing removed to show internal components of the pump assembly.

FIG. 13P illustrates a side view of the pump assembly 150G with the pump housing 153G lifted away in order to show the internal components of the pump assembly 150G. The pump assembly 150G can include a negative pressure source such as a pump 223G. The pump 223G can be fluidically connected to the connector port 203G via a manifold 225G. The manifold 225G can be connected to a pressure sensor 227G by a pressure sensing line 229G. The pressure sensor 227G can communicate with a printed circuit board (PCB) 231G. The PCB 231G can be adapted to receive a signal from the pressure sensor 227G such that the PCB 231G can detect the magnitude of the negative pressure within the manifold 225G.

Figure 13Q:
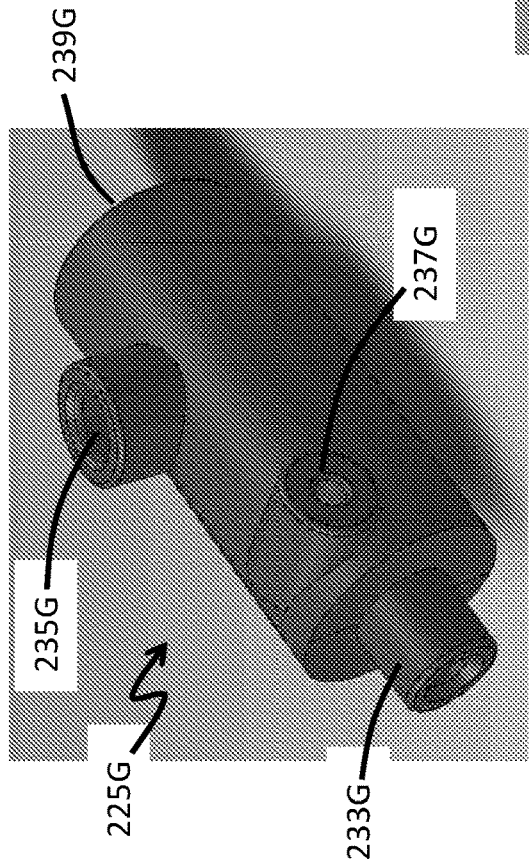
FIG. 13Q shows the manifold of the pump assembly of FIG. 13P.

FIG. 13Q shows a perspective view illustrating that the manifold 225G can include four ports. The manifold 225G can have a dressing port 233G that is in fluid communication with the connector port 203G. The manifold 225G can have a pump inlet port 235G that is in fluid communication with the pump 223G. The manifold 225G can have a pressure sensor port 237G that is in fluid communication with the pressure sensor 227G. The manifold 225G can have an overpressure port 239G that is adapted to allow fluid flow into the manifold 225G if the pressure within the manifold 225G exceeds a cracking pressure of the overpressure port 239G.

Figure 13R:
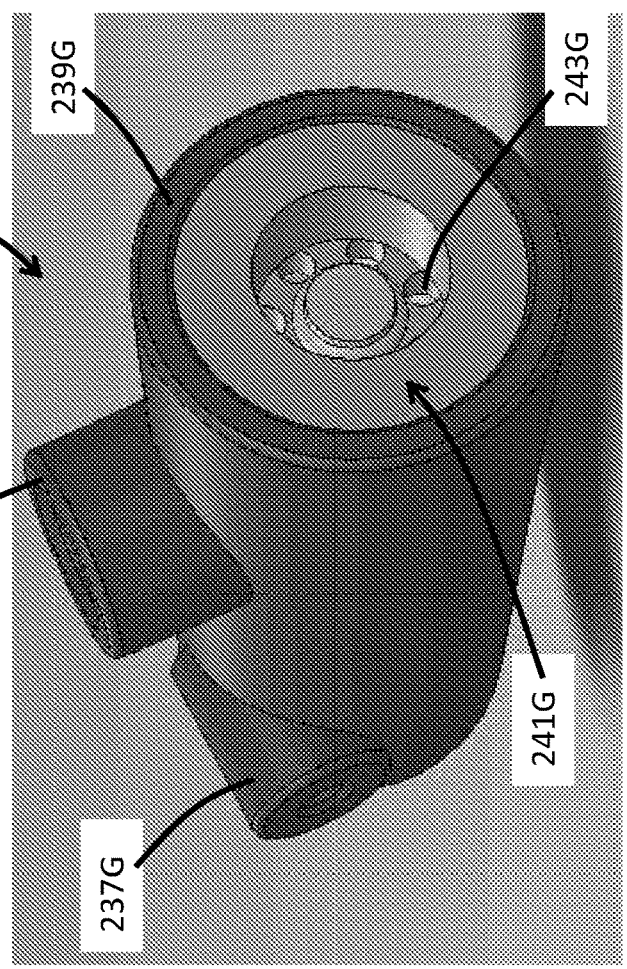
FIG. 13R shows a partial end view of the manifold of FIG. 13Q.

FIG. 13R shows a partial perspective view of the overpressure port 239G illustrating a regulator 241G that can be seated in the overpressure port 239G. The regulator 241G can be adapted to open a flow path through a vent 243G when a negative pressure inside the manifold 225G exceeds the cracking pressure of the regulator 241G. The regulator 241G can limit the magnitude of a negative pressure that is applied to a dressing attached to the connector 203.

Figure 13S:
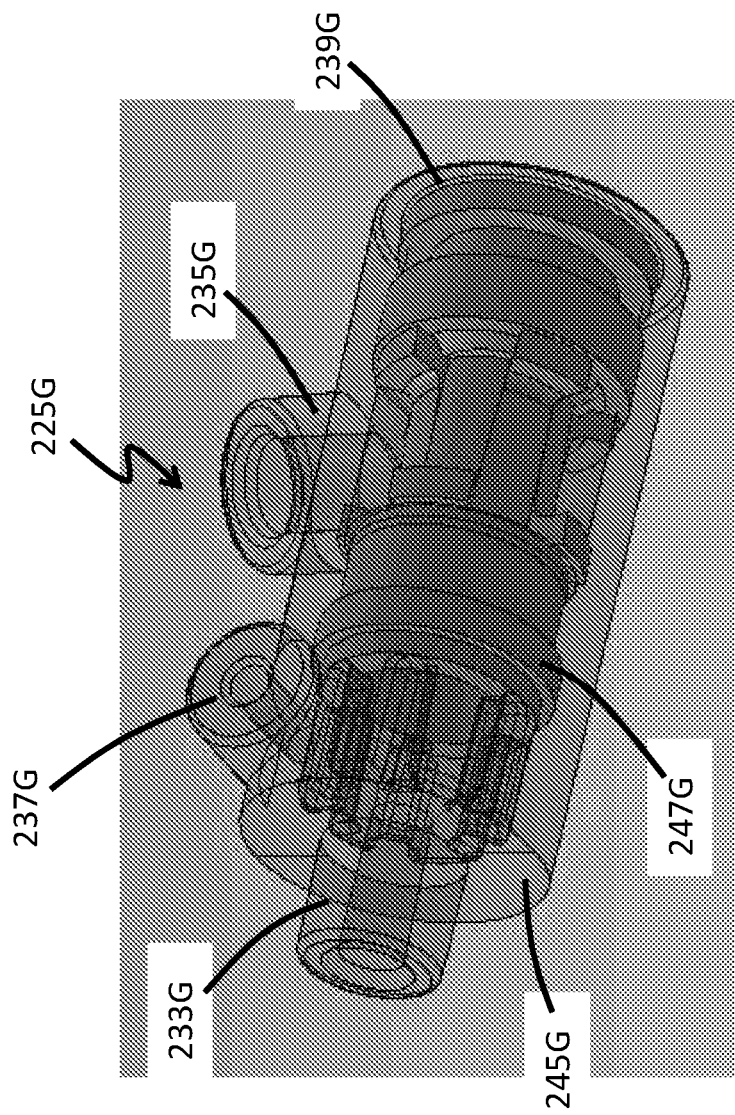
FIG. 13S shows the manifold of FIG. 13R with the manifold housing rendered transparent in order to show internal components of the manifold.

FIG. 13S shows a perspective view of the manifold 225G with the manifold housing 245G rendered transparent in order to show internal components of the manifold 225G. As shown in FIG. 13S, the manifold 225G can include a non-return valve (NRV) 247G. The NRV 247G can be adapted to allow flow through the valve 247G in one direction and prohibit flow through the NRV 247G in an opposite direction. In the illustrated embodiment, the NRV 247G allows air flow in the direction from the dressing port 233G toward the pump inlet port 235G. The NRV 247G blocks air flow in the direction from the pump inlet port 235G toward the dressing port 233G. The NRV 247G can prevent or reduce the negative pressure applied to the dressing port 233G from increasing toward atmospheric pressure when the pump 223G is turned off. In some embodiments, the manifold 225G is made of a pliable material (e.g., silicone). In some embodiments, the manifold 225G is made of a material having a durometer value between about 20 durometer and about 70 durometer. In some embodiments, the manifold is made of a flexible material that is adapted to reduce or attenuate vibrations and noise generated by the pump 223G.

In some embodiments, as illustrated in FIG. 13S, a medical device such as a pump assembly 150G as described herein can comprise a manifold 225G having a housing that defines a central flow channel that is in fluid communication with one or more ports. The manifold 225G can include a non-return valve (NRV) 247G disposed within the central flow channel. The NRV 247G can be disposed between an upstream portion and a downstream portion of the central flow channel. The NRV 247G can be adapted to allow flow through the NRV 247G in the direction from the downstream portion to the upstream portion of the central flow channel. The NRV 247G can block or impede flow through the NRV 247G in the direction from the upstream portion to the downstream portion. The one or more ports can include one or more of the following: a dressing port 233G in fluid communication with the downstream portion of the central flow channel; a pump inlet port 235G in fluid communication with the upstream portion of the central flow channel; an overpressure port 239G in fluid communication with the upstream portion of the central flow channel; and a pressure sensor port 237G in fluid communication with the downstream portion of the central flow channel. In some embodiments, the manifold is made of a flexible material that is adapted to reduce or attenuate vibrations and noise generated by a pump 223G that is arranged in fluid communication with the pump inlet port 235G.

Figure 14:
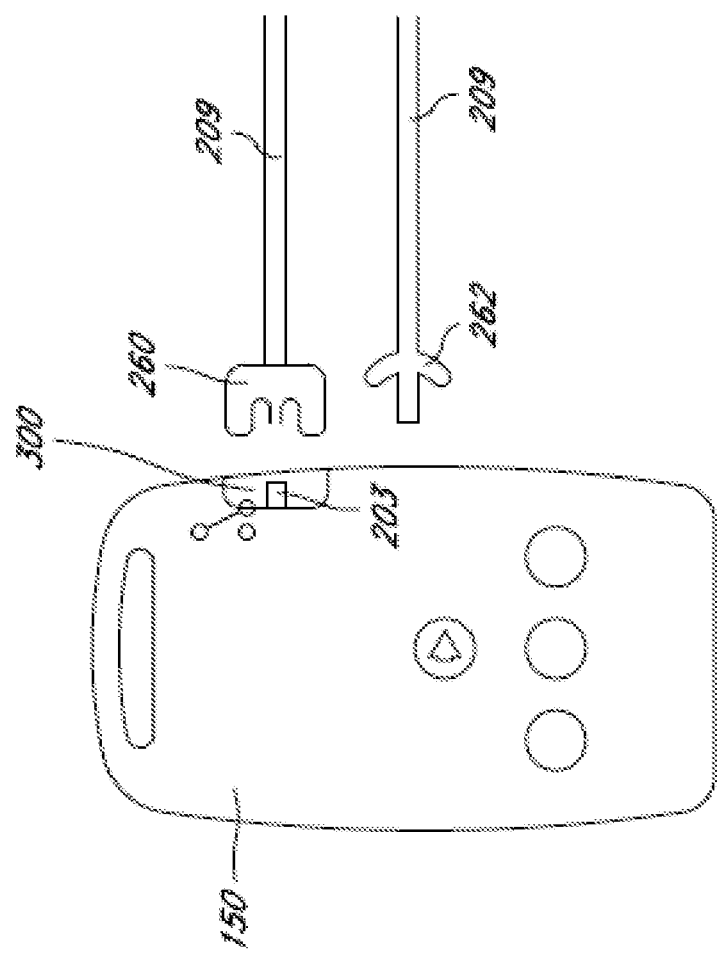
FIG. 14 illustrates an embodiment of a pump assembly that can receive a canister connector or a canisterless connector.

FIG. 14 illustrates that the TNP system 100 can include a connector switch 300. The connector switch 300 can be disposed on the pump assembly 150. The connector switch 300 can disposed near the connector port 203. As discussed in more detail below, the connector switch 300 be adapted to detect whether the connector port 203 is attached to a canister connector 260 or a canisterless connector 262. The connector port 203 can be adapted to connect to a canister connector 260 that is attached to a portion of tubing 209. The connector port 203 can be adapted to connect to a canisterless connector 262 that is attached to a portion of tubing 209.

Figure 15:
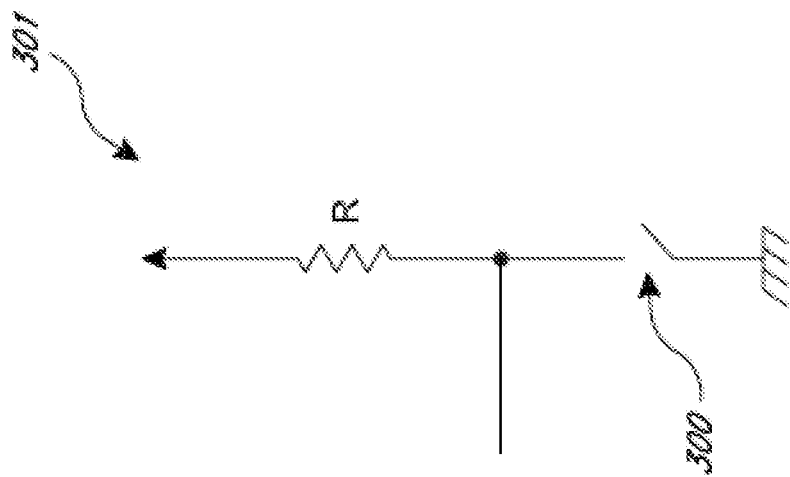
FIG. 15 illustrates an electrical circuit that can detect actuation of a connector switch.

FIG. 15 illustrates that the connector switch 300 can be adapted to close an electrical circuit 301 when the connector switch 300 is actuated. The connector switch 300 can be adapted so that the electrical circuit 301 is open when the connector switch 300 is not actuated. The connector switch 300 can be adapted so that the connector switch 300 is closed when a canister connector 260 is connected to the connector port 203 and is open when a canisterless connector 262 is connected to the connector port 203. The orientation can be switched so that the connector switch 300 is closed when a canisterless connector 262 is connected to the connector port 203 and is open when a canister connector 260 is connected to the connector port 203. The control board 206 (shown in FIG. 3A) can be adapted to detect whether the electrical circuit 301 is in the open or closed configuration. The control board 206 can be adapted to detect whether a canister connector 260 or a canisterless connector 262 is connected to the connector port 203.

FIGS. 16A-E illustrate various implementations of a connector switch 300 configured to engage one or more different connectors (e.g., the connectors 260, 262 in FIG. 14). In some embodiments, the one or more connector switches 300 described herein are substantially hidden from a user of the reduced pressure wound therapy system 100. For example, the connector switch 300 can be recessed within the housing of the pump assembly 150 or can be disposed under a gasket material. As described above, these various implementations advantageously allow the pump assembly 150 to differentiate between different types of connectors, such as, for example, between canister connectors 260 and canisterless connectors 262, The pump assembly 150 can, for example, thereby automatically determine whether to function in one or more different modes of operation, such as a canister-connected mode or canisterless mode. The one or more different modes of operation can differ, for instance, at least in the associated pump operating pressure settings like pressure thresholds, rates of change, or timings of pressure changes.

Figure 16A:
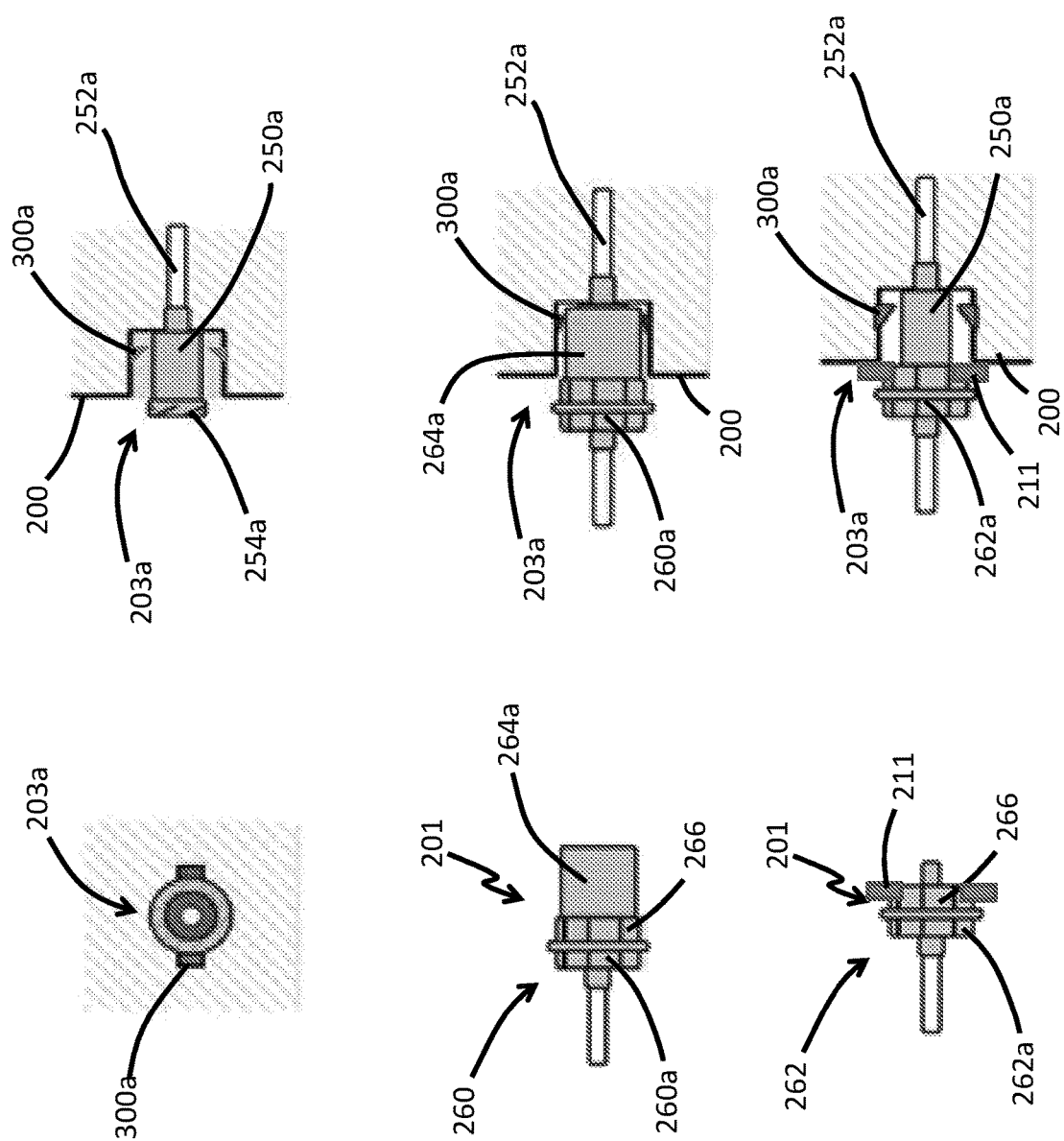
FIGS. 16A-E illustrate various implementations of a connector switch adapted to detect whether the connector port is connected to a canister connector or a canisterless connector.

In some embodiments, the connector port 203 can be disposed within a recessed portion of the housing 200 and can include one or more connector switches 300. For example, FIG. 16A illustrates a recessed connector port 203a having a pair of connector switches 300a disposed across from one another on a recessed portion of the housing 200. However, the connector port 203a need not have two connector switches 300a that are spaced apart circumferentially by 180 degrees. For example, the connector port 203a can have one, three, or more than three connector switches 300a. In embodiments that have multiple connector switches 300a, the connector switches 300a can be spaced apart circumferentially from an adjacent connector switch 300a by more or less than 180 degrees. As shown in FIG. 16A, in some embodiments the one or more connector switches 300a can be disposed on a side of the connector port 203a. In other words, the connector switch 300a can extend away from the housing 200 toward a longitudinal axis of the connector port 203a. In some embodiments, the connector switch 300a has more than one switch in order to provide redundant switches that allow for more tolerance in case of a mistaken connection arising from dirt or liquid.

The connector port 203a can have a central portion 250a that is fluidically connected to a pump lumen 252a. The central portion 250a can have an inlet end 254a that is adapted for coupling to a connector 201 to the connector port 203. The inlet end 254a can include any of a variety of means for attaching a connector 201 to the inlet end 254a. For example, in the illustrated embodiment the inlet end 254a includes a flange having an external thread that mates with an internal thread on the connector 201. However, the inlet end 254a need not have a thread and can include other well-known attachment means (e.g., barbed fitting).

With continued reference to FIG. 16A, the connector port 203a can be adapted to mate with a connector 201 to establish a flow path between the pump assembly 150 and the wound dressing, as discussed above. The connector 201 can be a canister connector 260 or a canisterless connector 262. The canister connector 260 can be integral with the canister 160 or can be disposed at the end of tubing 209, as discussed above. A canister connector 260 can be used when a canister 160 (shown in FIG. 2B) is disposed along the flow path from the wound dressing 180 to the pump assembly 150. A canisterless connector 262 can be used when there is no intervening canister along the flow path from the wound dressing 180 to the pump assembly 150, as illustrated in FIG. 2A. The connector 201 and connector port 203 can be adapted so that the pump assembly 150 can distinguish whether the connector port 203 is coupled to a canister connector 260 or to a canisterless connector 262. For example, the canister connector 260a can have an extended lip 264a that activates (e.g., presses) the connector switch 300a when the canister connector 260a is seated onto the connector port 203a, as shown in FIG. 16A. The canisterless connector 262a can lack the extend lip 264a so that the connector switch 300a is not activated when the canisterless connector 262a is coupled to the connector port 203a. The canisterless connector 262a can include a flange 211 that extends beyond the opening of the connector port 203 and prevents the canisterless connector 262a from being forced into the connector port 203. The flange 211 can help avoid the connector switch 300a being activated by a forced insertion of the canisterless connector 262a into the connector port 203a. In some embodiments, the canisterless connector 262a has the extended lip 264a while the canister connector 260a lacks the extended lip 264a so that the connector switch 300a is activated when the canisterless connector 262a is coupled to the connector port 203a but not when the canister connector 260a is coupled to the connector port 203a.

In the embodiment shown in FIG. 16A, the extended lip 264a extends from a collar portion 266 of the canister connector 260, In the illustrated embodiment, a face of the collar portion 266 substantially aligns with a face of the housing 200 when the canister connector 260a is seated onto the connector port 203a, and the extended lip 264a substantially fills the recess of the housing 200. However, in some embodiments, the collar portion 266 can be sized to extend partially into the recess. In some configurations, the connector 201 can include a protective feature that helps seal the recess to avoid dirt or moisture from reaching the connector switch 300. For example, the connector 201 can include a silicone flange that extends radially beyond the recess and seats against the housing 200 when the connector 201 is coupled to the connector port 203. In some embodiments, the protective feature is an o-ring that seals against the recessed wall of the housing. The protective feature can be disposed on both the canister connector 260 and the canisterless connector 262 and can be adapted so that the protective feature does not activate the control switch 300 when the connector 201 is coupled to the connector port 203.

Figure 16B:
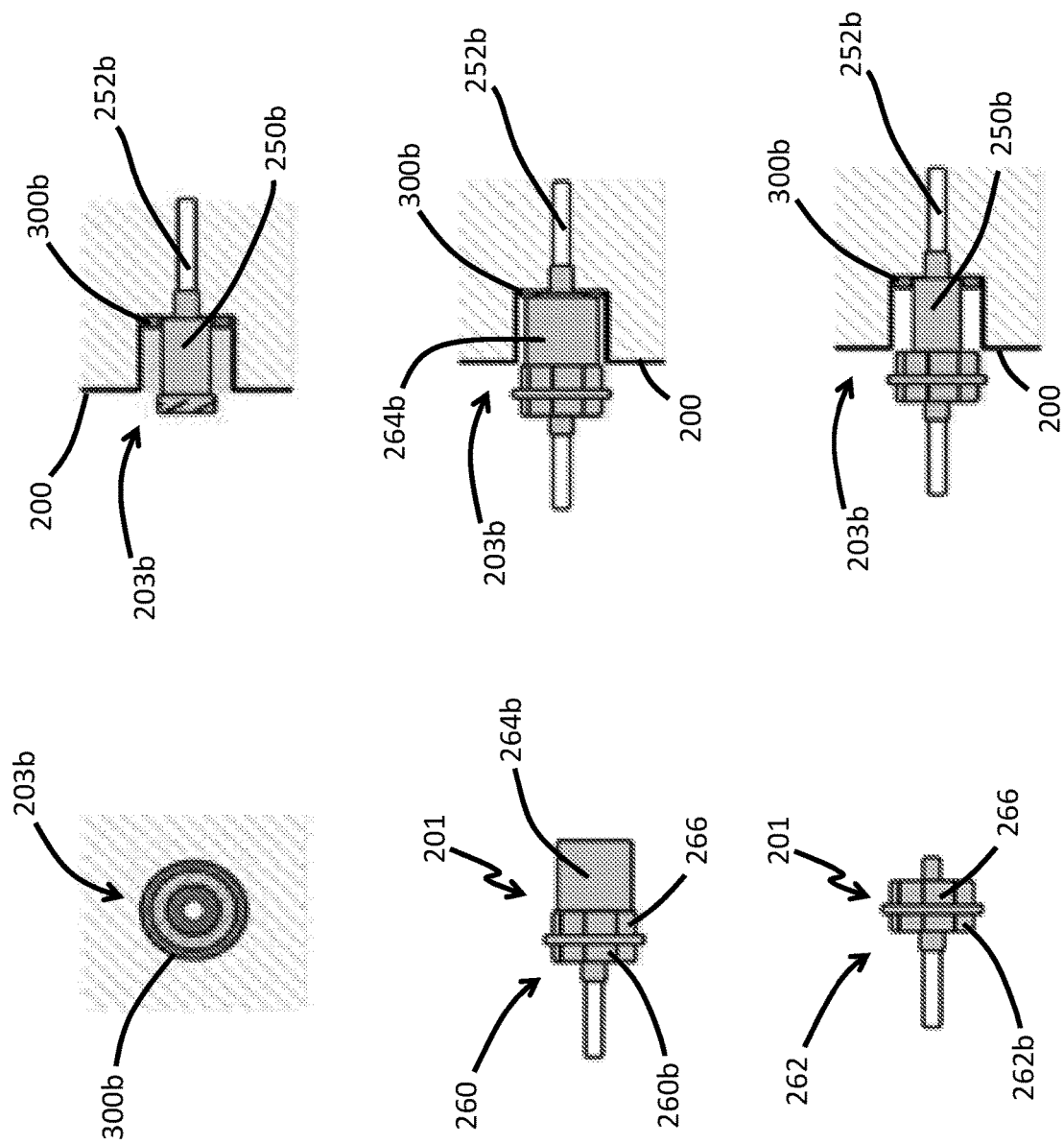

FIG. 16B illustrates an embodiment of a connector port 203b that is similar to the connector port 203a except as described differently below. The features of the connector port 203b can be combined or included with the connector port 203a or any other embodiment discussed herein. The connector port 203b can have a connector switch 300b that is disposed circumferentially around the central portion 250b of the connector port 203b at the base of the recessed portion of the housing 200, as shown in FIG. 16B, In this way, the connector switch 300b is shaped like a doughnut or ring. The connector switch 300b can be activated (e.g., pressed) by a lip 264b that extends from a collar portion 266 of the canister connector 260. In some embodiments, the canisterless connector 262b has the extended lip 264b while the canister connector 260b lacks the extended lip 264b so that the connector switch 300b is activated when the canisterless connector 262b is coupled to the connector port 203b but not when the canister connector 260a is coupled to the connector port 203a. In some configurations, the connector 201 can include a protective feature that helps seal the recess to avoid dirt or moisture from reaching the connector switch 300, as discussed above.

Figure 16C:
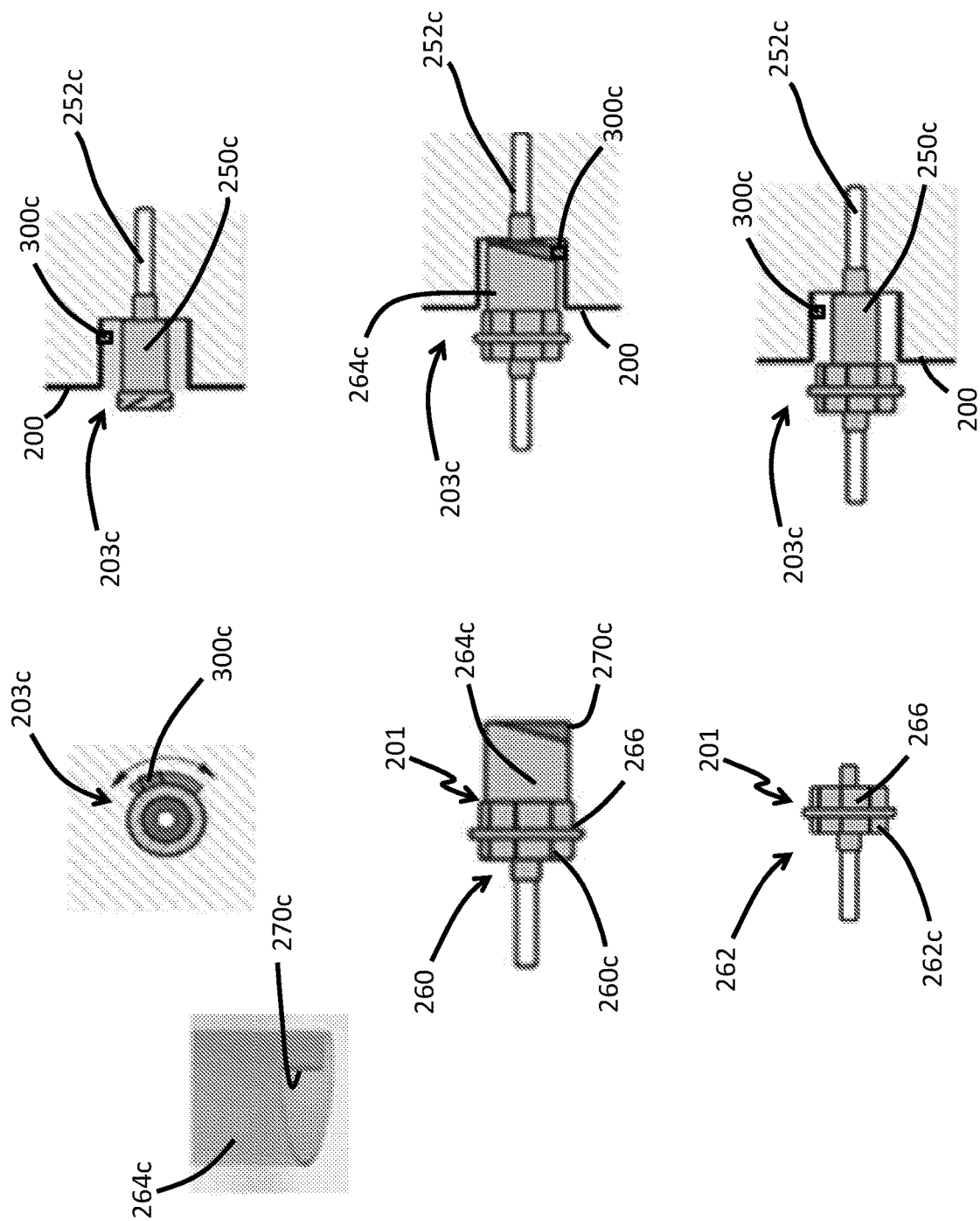

FIG. 16C illustrates an embodiment of a connector port 203c that is similar to the connector port 203b except as described differently below. The features of the connector port 203c can be combined or included with the connector port 203b or any other embodiment discussed herein. The connector port 203c can include a connector switch 300c that is a rotational switch. The connector switch 300c can engage various connectors 201 when engaged at various rotational positions with respect to the connector port 203c. For example, in some embodiments, a canister connector 260c can be configured to engage the connector switch 300c when the canister connector 260*c* is rotated after it is attached to the connector port 203*c* (e.g., a twist lock arrangement). As shown in the top right insert of FIG. 16C, the connector switch 300*c* can protrude into the recess from the housing 200. The connector switch 300*c* can be adapted to move within a groove or slot in the housing 200 so that the connector switch 300*c* can move from a first position to a second position. The connector switch 300*c* can be activated in the first position and de-activated in the second position or vice versa. The connector switch 300*c* can be biased to return to a rest position. The rest position of the connector switch 300*c* can be the activated position or the unactivated position of the connector switch 300*c*.

In some embodiments the canister connector 260*c* can have an extended lip 264*c* that activates (e.g., rotates) the connector switch 300*c* when the canister connector 260*c* is coupled to the connector port 203*c*. The extended lip 264*c* can have a helical cut that forms an abutment surface 270*c*, as shown in the top left insert of FIG. 16C. The abutment surface 270*c* can be sized to move the connector switch 300*c* from the de-activated position to the activated position when the canister connector 260*c* is coupled to the connector port 203*c*. The canisterless connector 262*c* can lack the extend lip 264*c* so that the connector switch 300*c* is not activated when the canisterless connector 262*c* is coupled to the connector port 203*c*. In some embodiments, the canisterless connector 262*c* has the extended lip 264*c* and the abutment surface 270*c* while the canister connector 260*c* lacks the extended lip 264*c* so that the connector switch 300*c* is activated when the canisterless connector 262*c* is coupled to the connector port 203*c* but not when the canister connector 260*c* is coupled to the connector port 203*c*. In some embodiments, the abutment surface 270*c* moves the connector switch 300*c* from an activated position to a de-activated position when the connector 201 is coupled to the connector port 203*c*. In some configurations, the connector 201 can include a protective feature that helps seal the recess to avoid dirt or moisture from reaching the connector switch 300, as discussed above. In some configurations, the rotational connector switch 300*c* and the abutment surface 270*c* can each include conductive material configured to engage and complete an electrical circuit when the connector 201 is rotated a threshold amount (e.g., to indicate a canister connector 260 as a opposed to a canisterless connector 262 is attached).

Figure 16D:
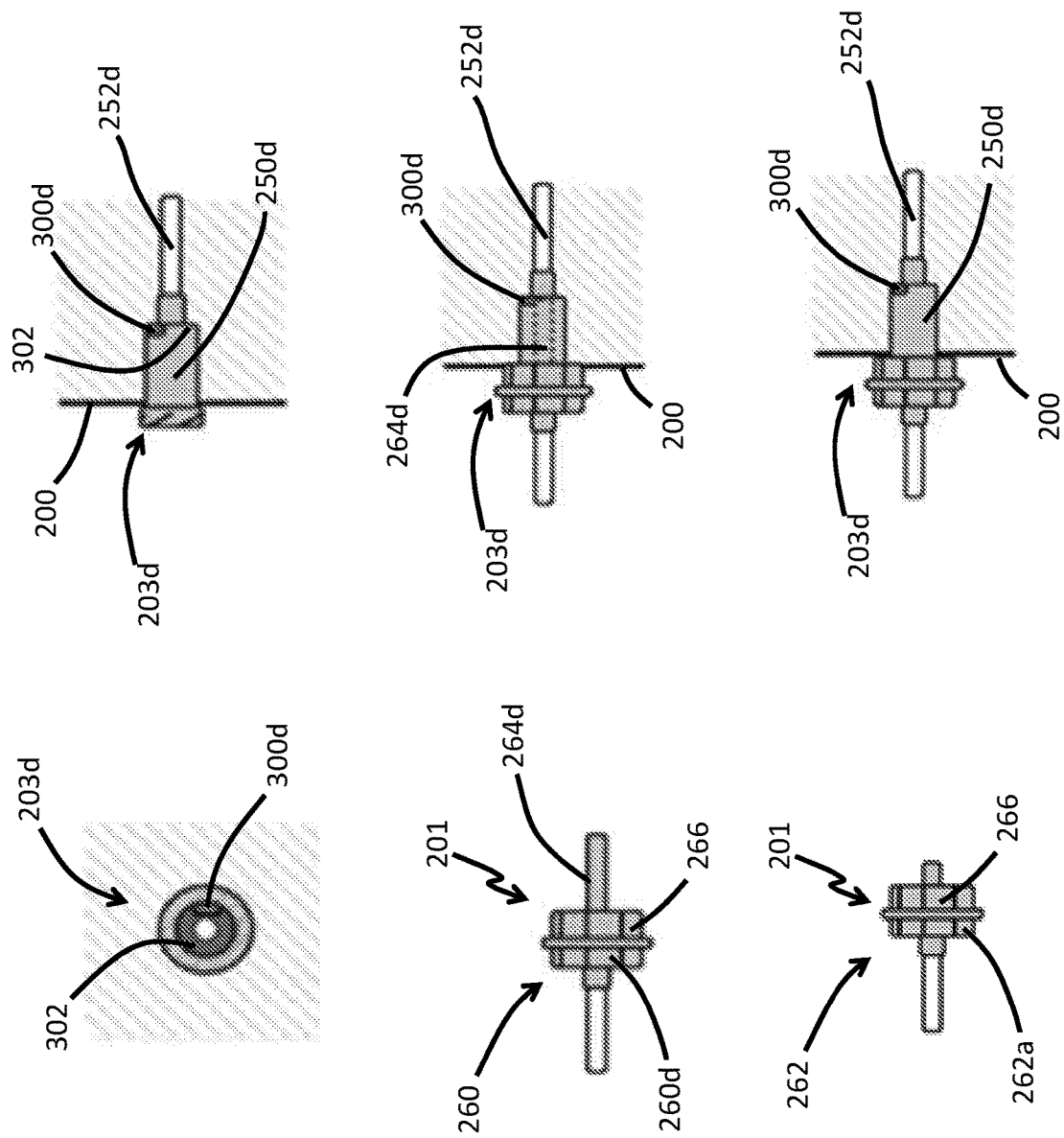

FIG. 16D illustrates an embodiment of a connector port 203*d* that is similar to the connector port 203*c* except as described differently below. The features of the connector port 203*d* can be combined or included with the connector port 203*c* or any other embodiment discussed herein. The connector port 203*d* can include a connector switch 300*d* that is located inside the connector port 203*d*, as shown in FIG. 16D. In some configurations, the connector switch 203*d* can be located directly in the air flow passing through the connector port 203*d*. Positioning the connector switch 300*d* within the connector port 203*d* has the advantage of completely protecting the connector switch 300*d* during use. As shown in the illustrated embodiment, the connector switch 300*d* can be located on a shoulder 302 that is inside the connector switch 300*d*.

The canister connector 260*d* can have an extended lip 264*d* that activates (e.g., presses) the connector switch 300*d* when the canister connector 260*d* is connected to the connector port 203*a*, as shown in FIG. 16D. The canisterless connector 262*d* can lack the extend lip 264*d* so that the connector switch 300*d* is not activated when the canisterless connector 262*d* is coupled to the connector port 203*d*. In some embodiments, the canisterless connector 262*d* has the extended lip 264*d* while the canister connector 260*d* lacks the extended lip 264*d* so that the connector switch 300*d* is activated when the canisterless connector 262*d* is coupled to the connector port 203*d* but not when the canister connector 260*d* is coupled to the connector port 203*d*.

Figure 16E:
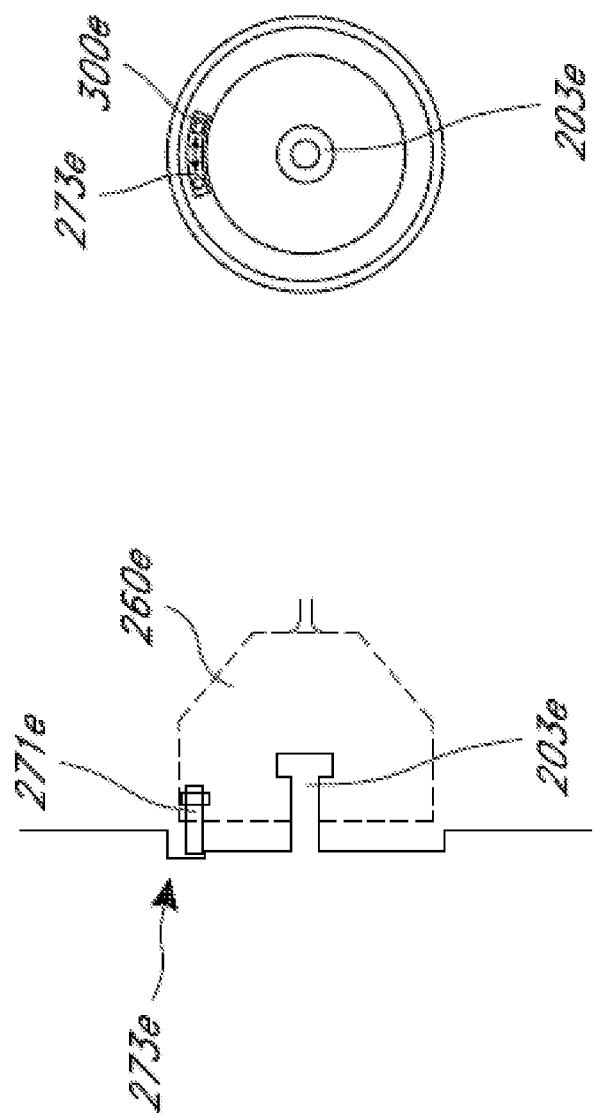

FIG. 16E illustrates an embodiment of a connector port 203*e* that can include a connector switch 300*e* that is actuated by rotation of the canister connector 260*e*. The canister connector 260*e* can include a spigot 271*e* that extends into a recess 273*e* that surrounds the connector port 203*e*. When the canister connector 260*e* is rotated to attach the canister connector 260*e* to the connector port 203*e*, the spigot 271 slides within the groove 273*e* and actuates the connector switch 300*e* disposed within the groove 273*e*. A gasket 275*e* can seal the bottom of the groove 273*e*.

Figure 17:
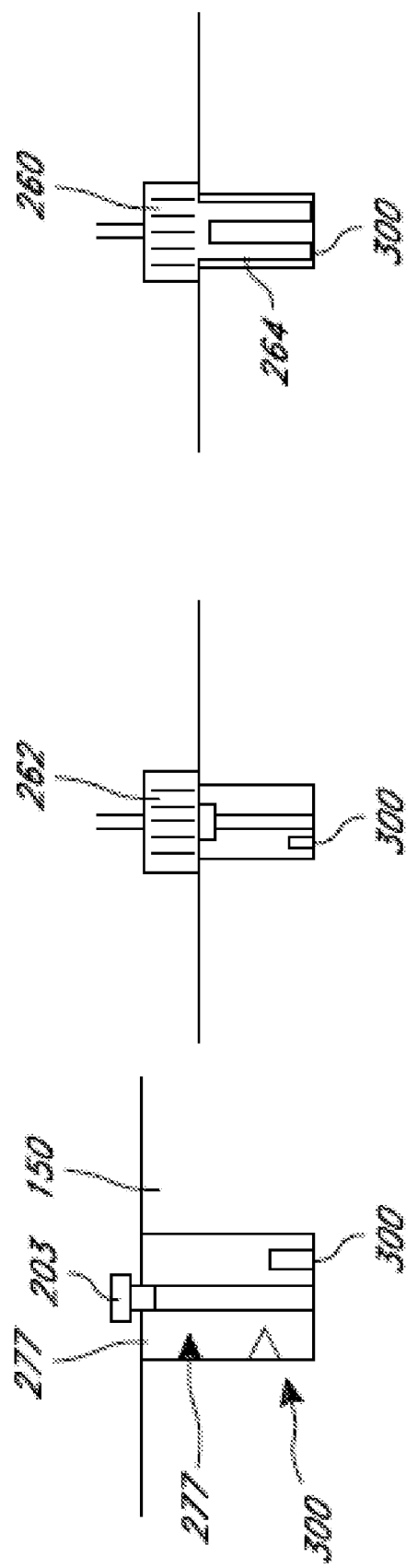
FIG. 17 illustrates a membrane seal that can protect the connector switch from dirt and liquid.

FIG. 17 illustrates that a membrane seal 277 can extend from the connector port 203 to the housing of the pump assembly 150 to form a sealed compartment 279 that contains the connector switch 300. The membrane seal 277 can protect the connector switch 300 from being contaminated with dirt or liquid. The membrane seal 277 can be flexible enough to allow the extended lip 264 of the canister connector 260 to stretch the membrane 277 so that the extended lip 264 can activate the connector switch 300 when the canister connector 260 is connected to the connector port. In some variants, the membrane seal 277 has a slit that allows the extended lip 264 to pass through the slit but the membrane 277 forms a snug fit against the outer surface of the extended lip 264 to keep dirt out of the compartment 279.

Figure 18:
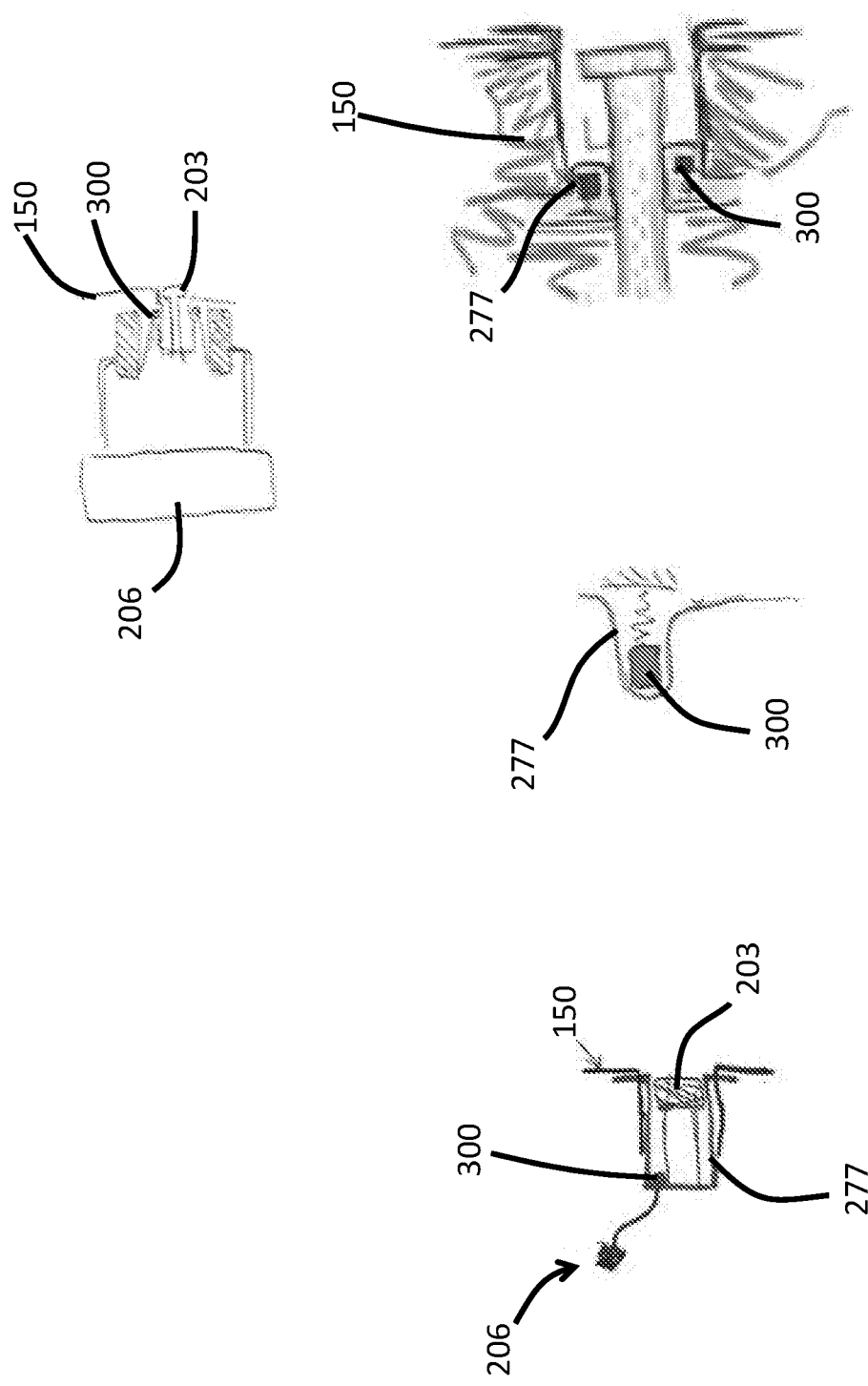
FIG. 18 illustrates other configurations of a membrane seal that can protect the connector switch from being contaminated by dirt or liquid.

FIG. 18 illustrates other configurations of a membrane seal 277 that can protect the connector switch 300 from being contaminated by dirt or liquid. The seal 277 can line the recessed portion of the pump assembly 150 housing that surrounds the connector port 203, The membrane seal 277 can cover the connector switch and allow the connector switch 300 to move between an actuated and unactuated state similar to a flexible cover that overlays the keys of a keyboard or calculator. In certain arrangements, the membrane seal 277 can extend over the connector switch 300 from within the housing of the pump assembly 150. In some arrangements, the connector switch 300 can be sealed in the housing of the pump assembly 150 and be deflected when a connector 201 is attached to the connector port 203, The control board 206 can be configured to detect when the connector switch 300 has been deflected.

Figure 19:
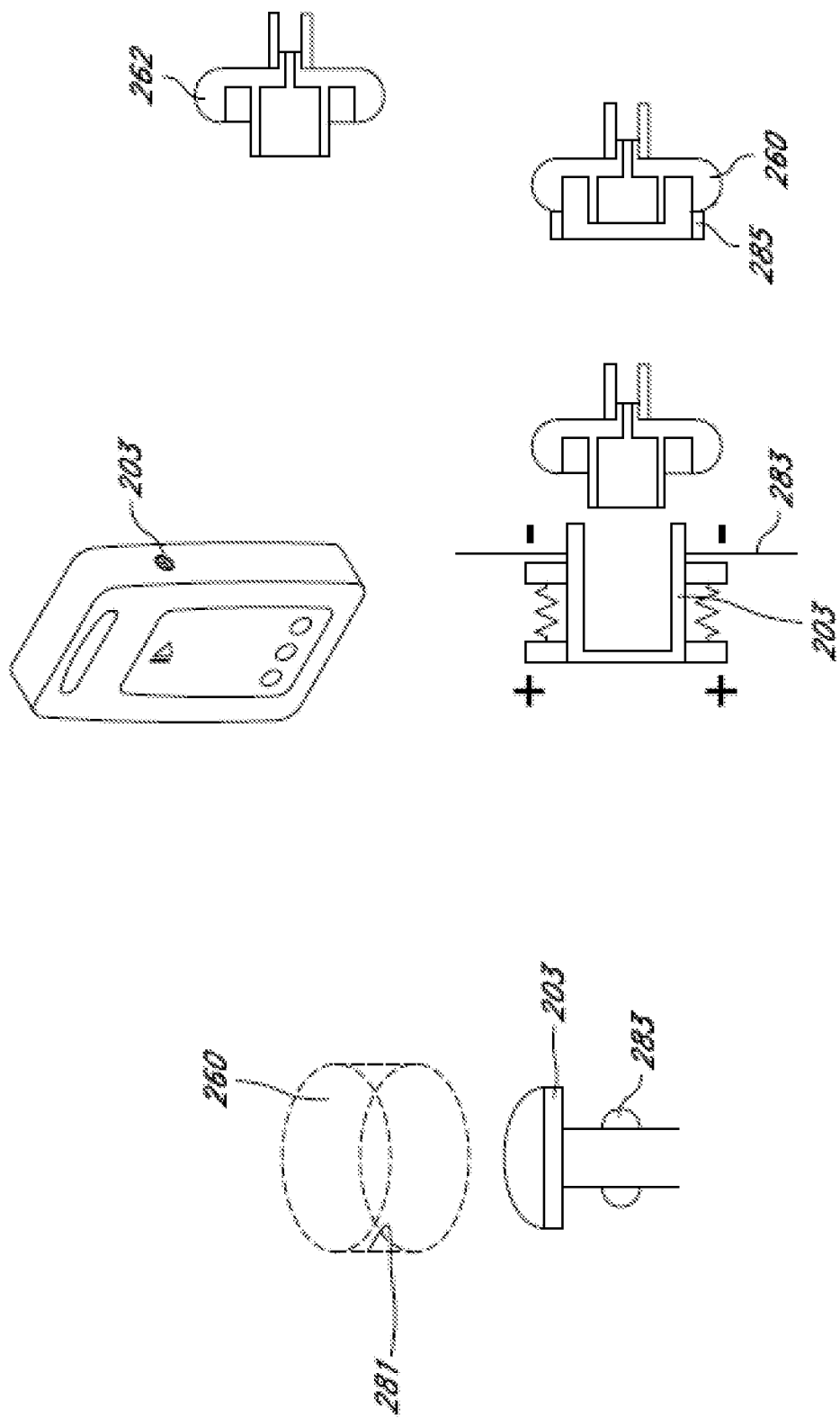
FIG. 19 illustrates connector switch embodiments that include electrical switches.

FIG. 19 illustrates connectors 201 that are configured to complete an electrical circuit when the connector 201 is attached to the connector port 203. For example, the canister connector 260 can have a conductive material disposed on an inner surface 281 of the canister connector 260. The connector port 203 can have metal connections 283 on both sides of the connector port 203. When the canister connector 260 is attached to the connector port 203, the conductive ring of material disposed on the inner surface 281 of the canister connector 260 can establish an electrical connection between the metal connections 283. The control board 206 of the pump assembly 150 can be configured to detect when an electrical connection is made between the metal connections 283 of the connector port 203, thereby signaling to the pump assembly 150 that a canister connector 260 is attached to the connector port 203. In certain arrangements, the metal connections 283 can be circumferentially disposed around the connector port 203. The canister connector 260 can include a conductive ring 285 that is disposed on a distal face of the canister connector 260. The conductive ring 285 can establish an electrical contact between the metal connections 283 when the canister connector 260 is attached to the connector port 203. The distal face of the canisterless connector 262 can be non-conductive so that an electrical contact is not formed between the metal connections 283 when the canisterless connector 262 is attached to the connector port 203.

FIG. 20 illustrates connector switches 300 that are actuated by a connector 201 that has a first outer diameter and are not actuated by a connector 201 that has a second outer diameter. The connector switch 300 can be disposed on the housing of the pump assembly 150 a first radial distance away from the connector port 203. A canisterless connector 262 can have an outer radius that is less than the first radial distance so that the connector switch 300 is not contacted by the canisterless connector 262 when the canisterless connector 262 is attached to the connector port 203. The canister connector 260 can have a radial distance that is equal to or greater than the first radial distance so that the connector switch 300 is contacted (e.g., depressed) by the canister connector 260 when the canister connector 260 is attached to the connector port 203. The connectors 201 can have a fitting 291 (e.g., barb fitting) that allows the connector 201 to be attached to tubing 209. The fitting 291 of the canister connector 260 can be differently sized compared to the fitting 291 of the canisterless connector 262, thereby avoiding the misuse of a connector 201 being attached to the incorrect tubing 209. In some arrangements, the connector port 203 can include an external thread that mates with an internal thread of the connector 201.

Figure 21:
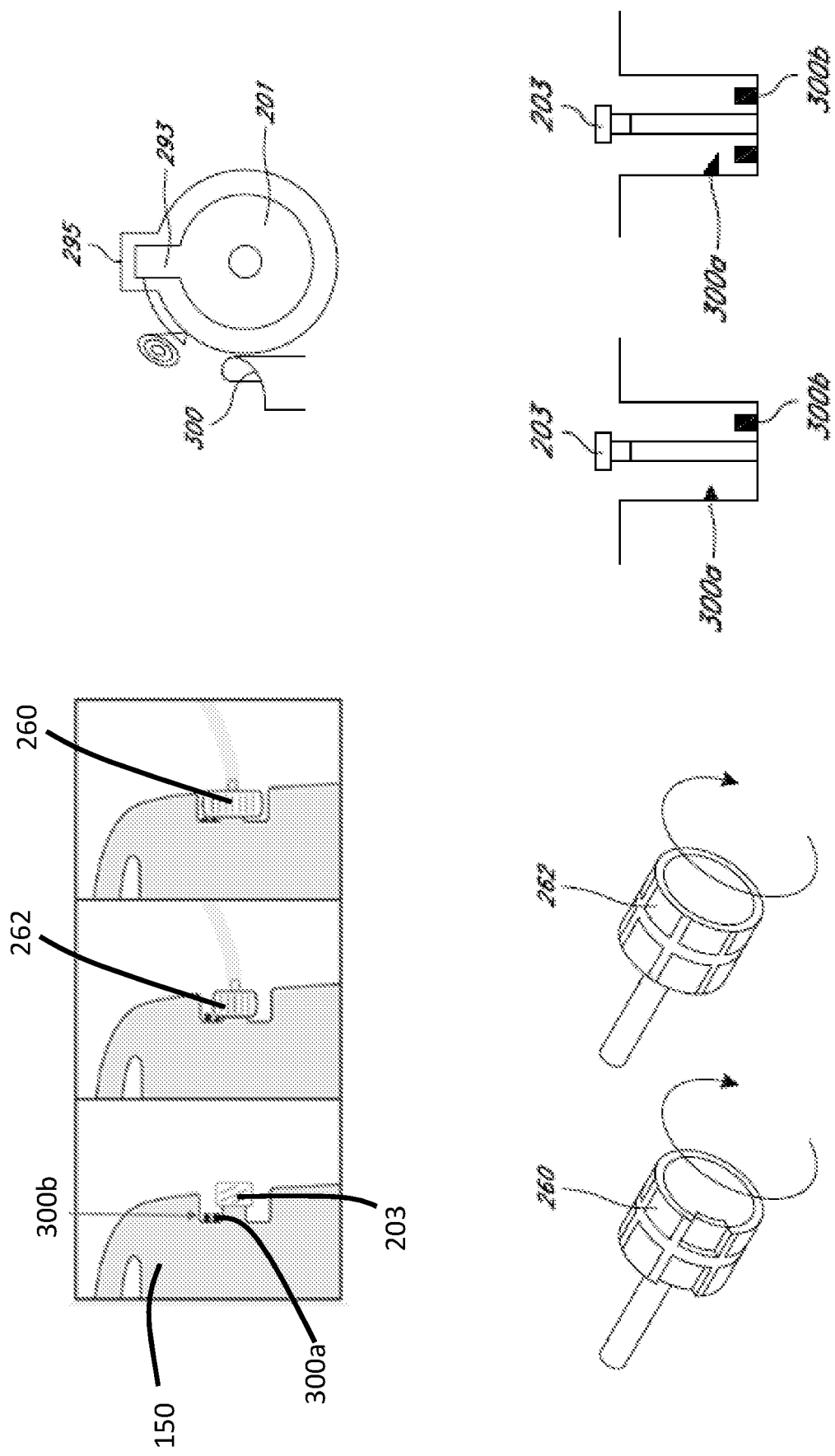
FIG. 21 illustrates connector switch embodiments that include more than one connector switches.

FIG. 21 illustrates that more than one connector switches 300 can be used so that the pump assembly 150 can detect whether a sealing connection has been made between the connector port 203 and the connector 201 whether a canister connector 260 or a canisterless connector 262 is connected to the connector port 203. For example, the pump assembly 150 can have a first connector switch 300a disposed a first radial distance from the connector port 203 and a second connector switch 300b disposed a second radial distance from the connector port 203. The canisterless connector 262 can be sized so that it actuates the first connector switch 300a but not the second connector switch 300b when the canisterless connector 262 is connected to the connector port 203. The canister connector 260 can be sized so that it actuates both the first connector switch 300a and the second connector switch 300b when the canister connector 260 is connected to the connector port 203. In certain arrangements, the connector switches 300 can be arranged like tumblers in a keyed lock. For example, the connector 201 can include one or more protrusions 293 that are longitudinally spaced apart along a housing of the connector 201. The protrusions 293 can be sized to actuate one or more corresponding connector switches 300 that are spaced longitudinally apart inside the housing of the pump assembly 150. The protrusions 293 are received into a recess 295 when the connector 201 is attached to the connector port 203. The connector 201 can be rotated a 4 turn to lock the connector 201 onto the connector port 203, thereby actuating the connector switches 300 with the corresponding protrusions 293.

Figure 23:
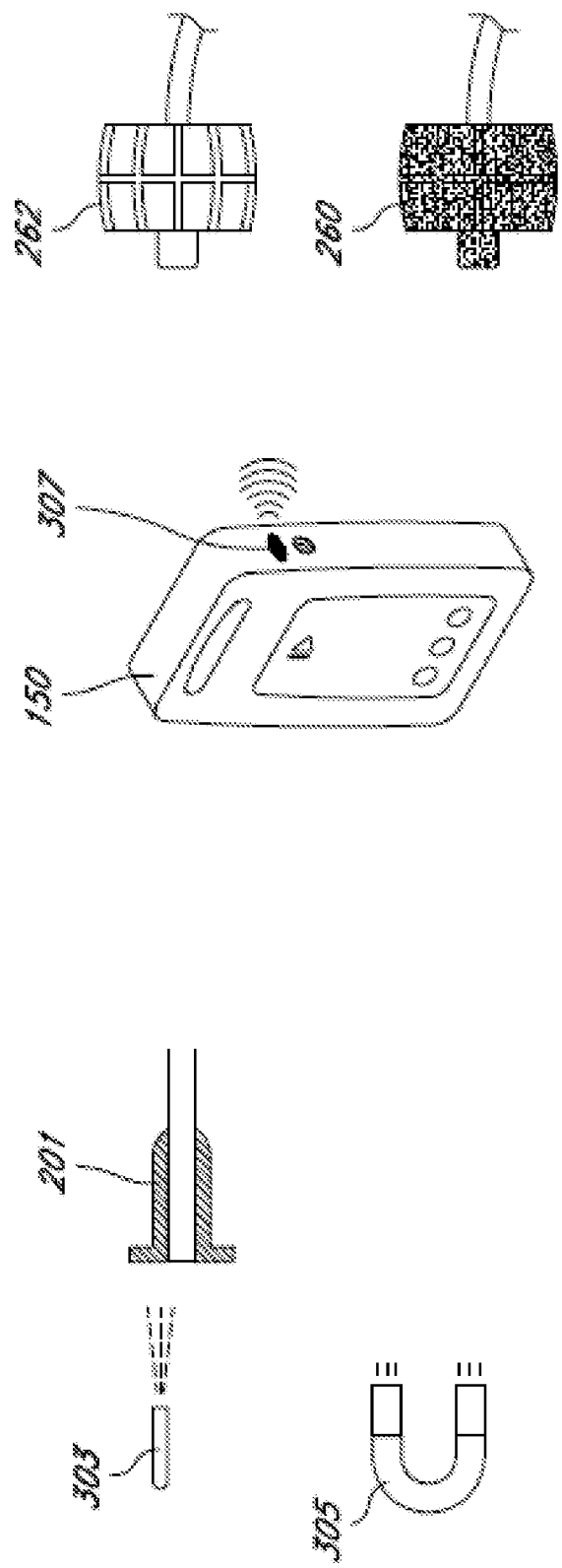
FIG. 23 illustrates connector switch embodiments that include a sensor.

FIG. 22 illustrates that the connector port 203 and/or the connector 201 can include an LED ring 297 to indicate when the connector 201 is sealingly attached to the connector port 203. The LED ring 297 can light different colors depending on whether a canister connector 260 or a canisterless connector 262 is attached to the connector port 203. The connector 201 can include a protector 299 adapted to seal dirt seeping into the switch 300, FIG. 23 illustrates that the connector switch 300 can include one or more of a proximity sensor 303, a light sensor (not shown), or a magnet 305 to detect whether a canister connector 260 or canisterless connector 262 is attached to the connector port 203. The sensor can include a RFID-, mechanical-, photodiode-, magnetic-, or capacitive-based system. The pump assembly 150 can include an infrared sensor 307. The canister connector 260 can be made of a darker material compared to the canisterless connector 262. The infrared sensor 307 can be adapted to distinguish whether the connector 201 is made of a dark material (e.g., corresponding to a canister connector 260) or made of a light material (e.g., corresponding to a canisterless connector 262).

FIG. 24 illustrates that the connector switch 300 can include a magnetic proximity sensor 500 (e.g., Hall effect sensor) to detect when a canister 230 is attached to the pump assembly 150. The canister 230 can have a magnet 502 embedded into the canister 230. When the canister connector port 260 is coupled to connector port 203 of the pump assembly 150, the magnet 502 embedded in the canister 230 will be brought close to the magnetic proximity sensor 500 of the pump assembly 150. The magnetic proximity sensor 500 can detect the presence of the magnetic field of the magnet 502. Accordingly, the magnetic proximity sensor 500 can activate a detector circuit on the pump assembly 150 to indicate that a canister 230 is attached to the pump assembly 150. In some configurations, a spherical magnet 502 is embedded into the canister so that the magnet 502 radiates a substantially uniform magnetic field. In some arrangements a magnet 305 is embedded in the canister connector 260 and not in the canisterless connector 262, allowing a magnetic proximity sensor 500 of the pump assembly 150 to detect whether a canister connector 260 or canisterless connector 262 is connected to the connector port 203.

FIG. 25 illustrates that the pump assembly 150 can include an RFID tag reader adapted to read an RFID label 309 that is affixed to the canister 160. The pump assembly 150 can include two interchangeable interfaces 311: one for canister mode, and one for canisterless mode. The interchangeable interfaces 311 can include an ID tag to enable the pump assembly 150 to determine which operating mode to use.

Figure 26:
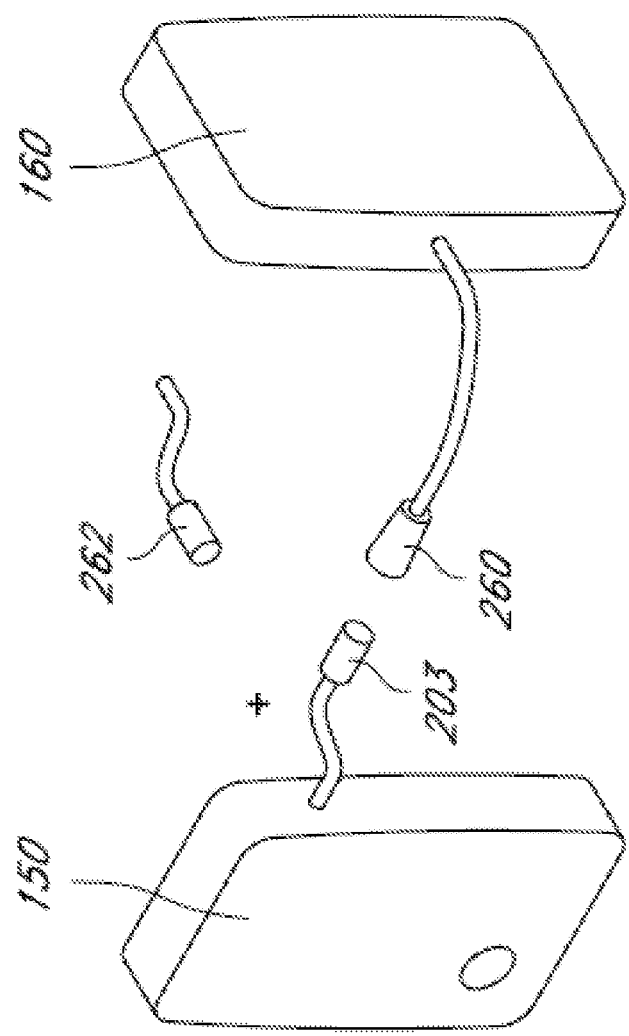
FIG. 26 illustrates connector switch embodiments that detect resistive properties of the attached connector.

FIG. 26 illustrates that the pump assembly 150 can include a connector port 203 that is configured to detect resistive properties of the connector that is attached to the connector port 203. For example, the connector port 203 can be configured to have a small current pass through the connector port 203. The material properties of the canister connector 260 can be different from those of the canisterless connector 262. For example, the canister connector 260 can include iron filings that decrease the resistive properties of the canister connector 260 compared to the resistive properties of the canisterless connector 262.

Figure 27:
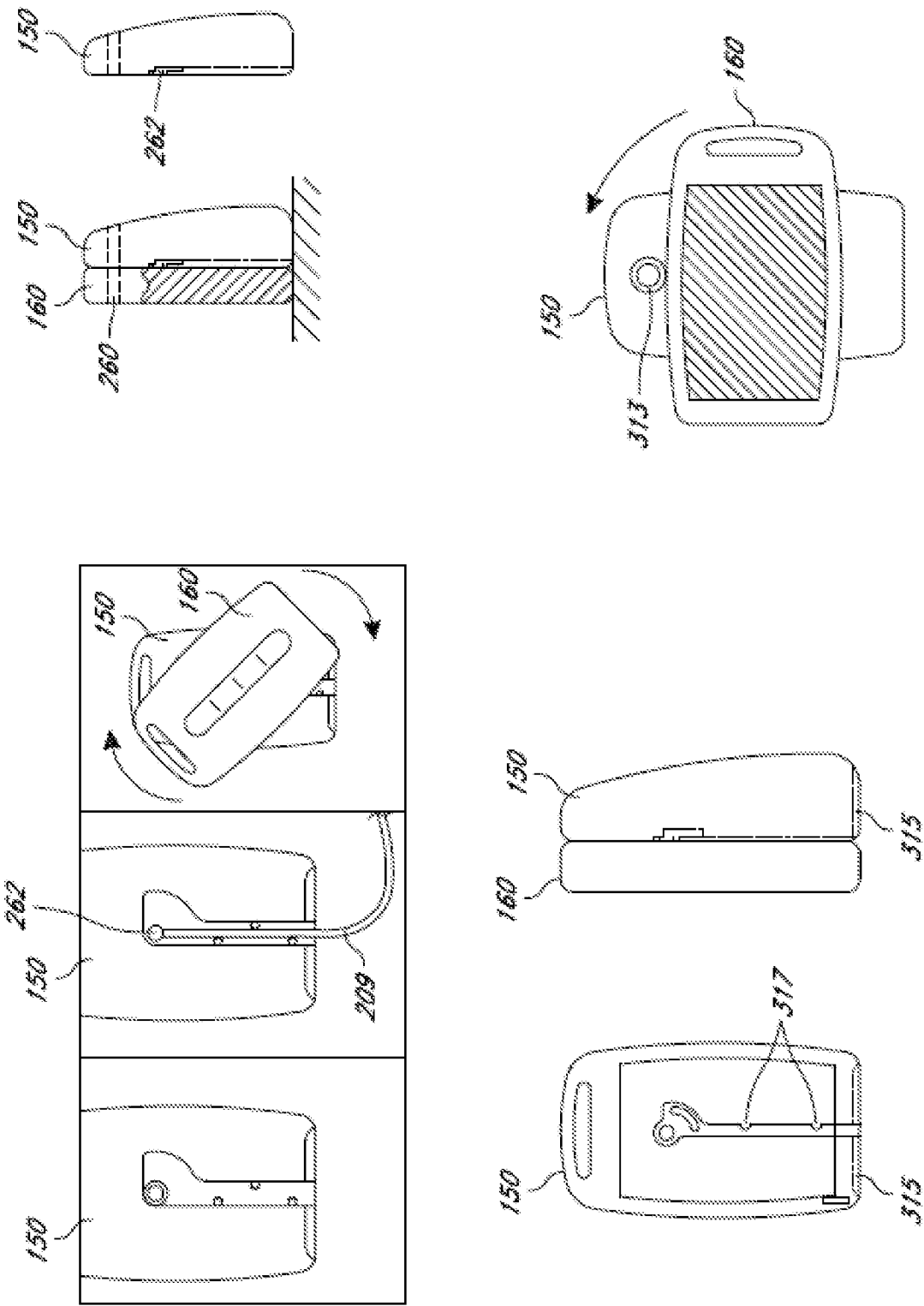
FIG. 27 illustrates a TNP system having two connector ports.

FIG. 27 illustrates that the pump assembly 150 can be arranged so that a canister connector 260 and a canisterless connector 262 cannot be attached to the pump assembly 150 at the same time. For example, the canister 160 can fit on a pump port and rotate to lock the canister into place. The canister connector 260 and the canisterless connector 262 can use separate ports to connect to the pump assembly 150. The canisterless connector port 262 can be blocked by the canister 160 when the canister 160 is attached to the pump assembly 150. The pump assembly 150 can include a pneumatic connection 313 adapted to connect the canister 160 to the pump assembly 150. The pump assembly 150 can include a sensor that detects the canister 160 is attached to the pump assembly 150. The pump assembly 150 can have a battery compartment 315 that is adapted to allow the batteries to be changed without removing the canister 160 from the pump assembly 150. The pump assembly can include tabs 317 that help keep tubing 209 of a canisterless connector seated against the back of the pump assembly 150.

Figure 28:
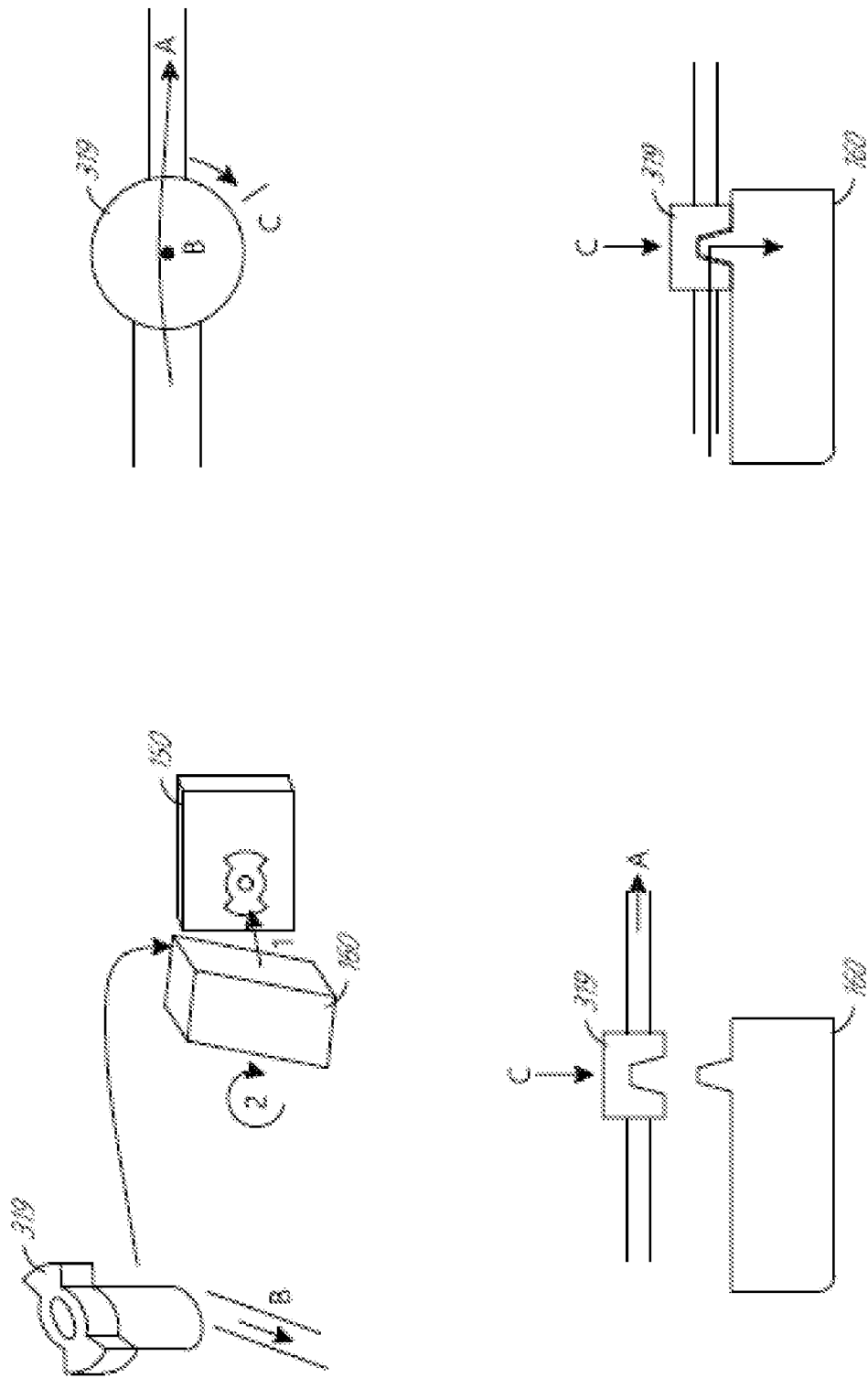
FIG. 28 illustrates a TNP system having a connector that can change the flow path through the connector.

FIG. 28 illustrates that the pump assembly 150 can be adapted so that rotating the canister 160 to attach the canister 160 to the pump assembly 150 moves a connector that changes the flow path through the connector 319.

Figure 29:
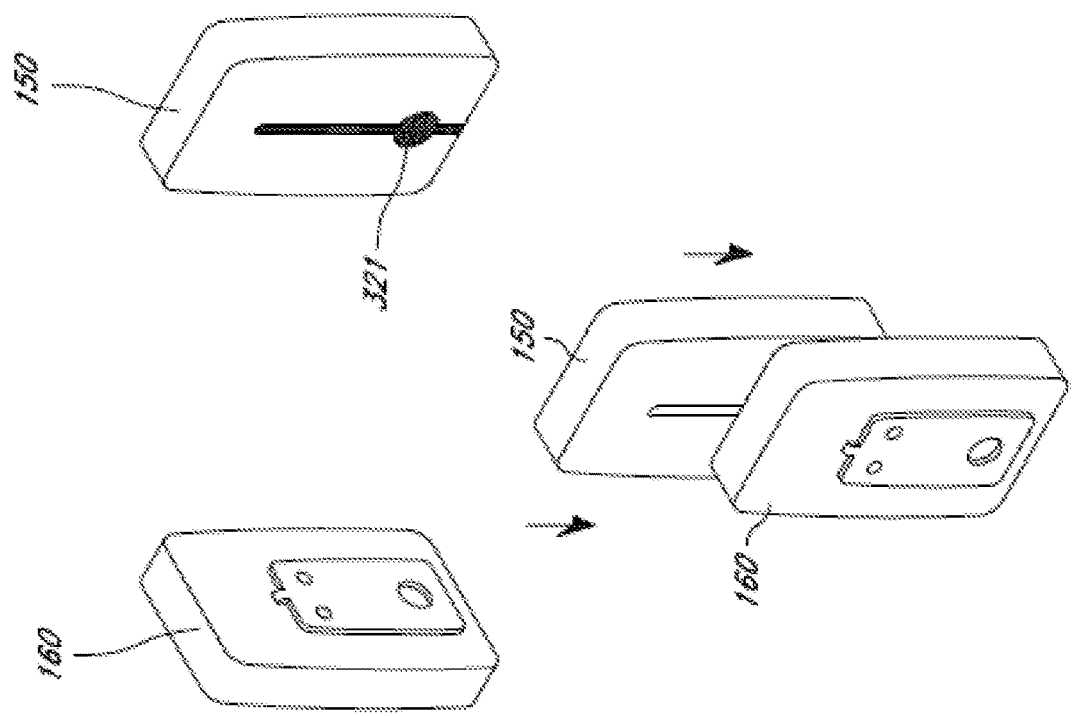
FIG. 29 illustrates a TNP system having a canister mounted onto the back of the pump assembly.

FIG. 29 illustrates that the canister 160 can slide onto a groove 321 on the back of the pump assembly 150. The canister 160 and the pump assembly 150 can include connectors that are adapted to align with one another when the canister 160 is slid onto the groove 321, thereby establishing an air path between the canister 160 and pump assembly 150.

Figure 30:
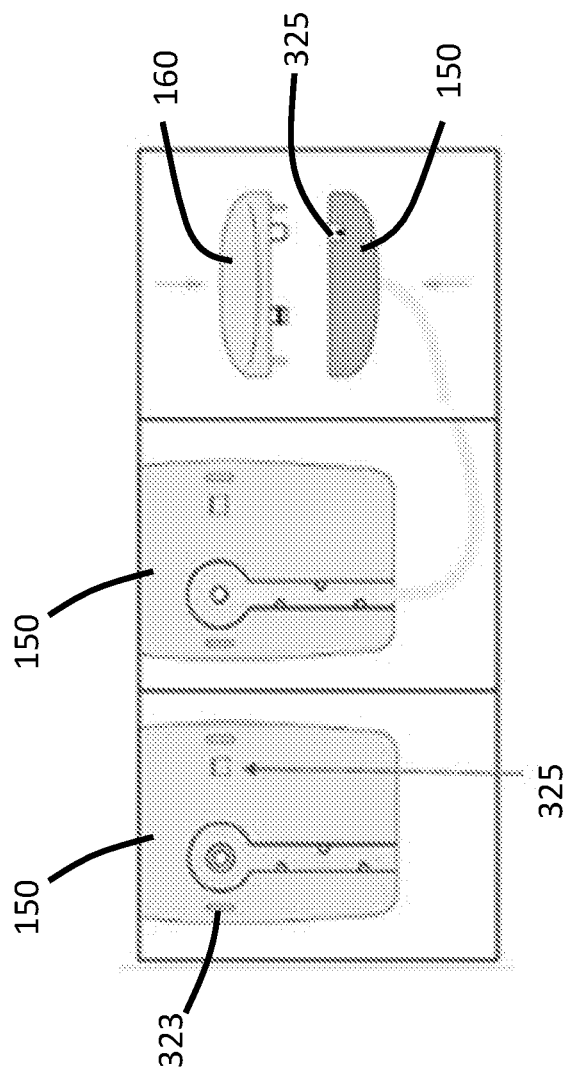
FIG. 30 illustrates a TNP system that prevents the canister being attached unless a mechanically sound connection is made between the pump assembly and the canister.
Figure 31:
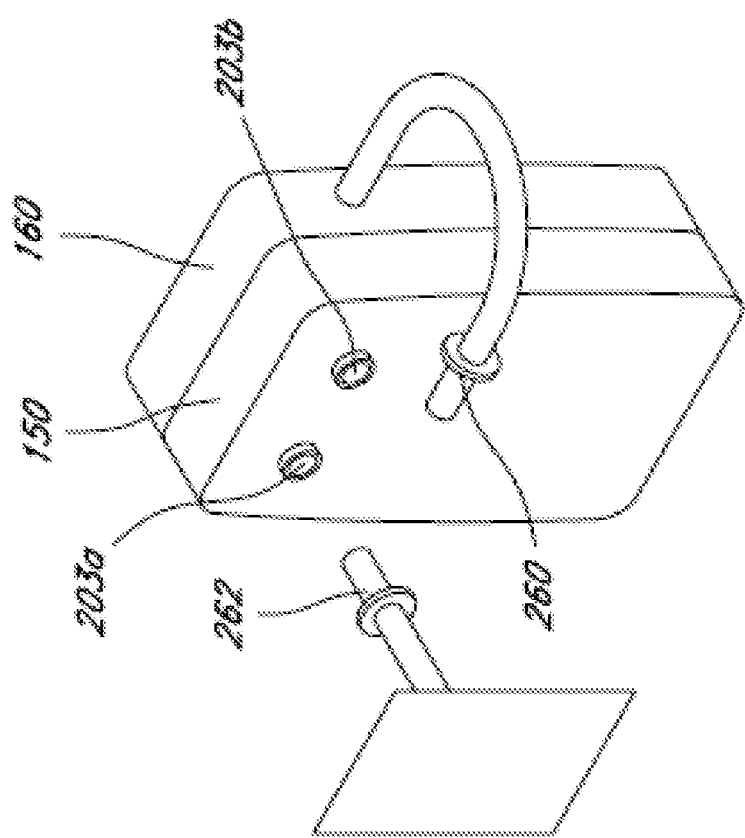
FIG. 31 illustrates a TNP system having two connector ports.

FIG. 30 illustrates that the pump assembly 150 can incorporate a latch 323 so that the canister 160 cannot be attached and/or locked into place unless a mechanically sound connection is made between the pump assembly 150 and the canister 160. The canister port can be normally blocked off but pushing the canister into the pump assembly opens a "cat-flap" latch 325 to the canister port and closes the canisterless port, FIG. 31 illustrates that the pump assembly 150 can incorporate a first port connector 203a for connecting the pump assembly 150 to a canisterless connector 262 and a second port connector port 203b for connecting the pump assembly 150 to a canister connector 260.

Figure 32:
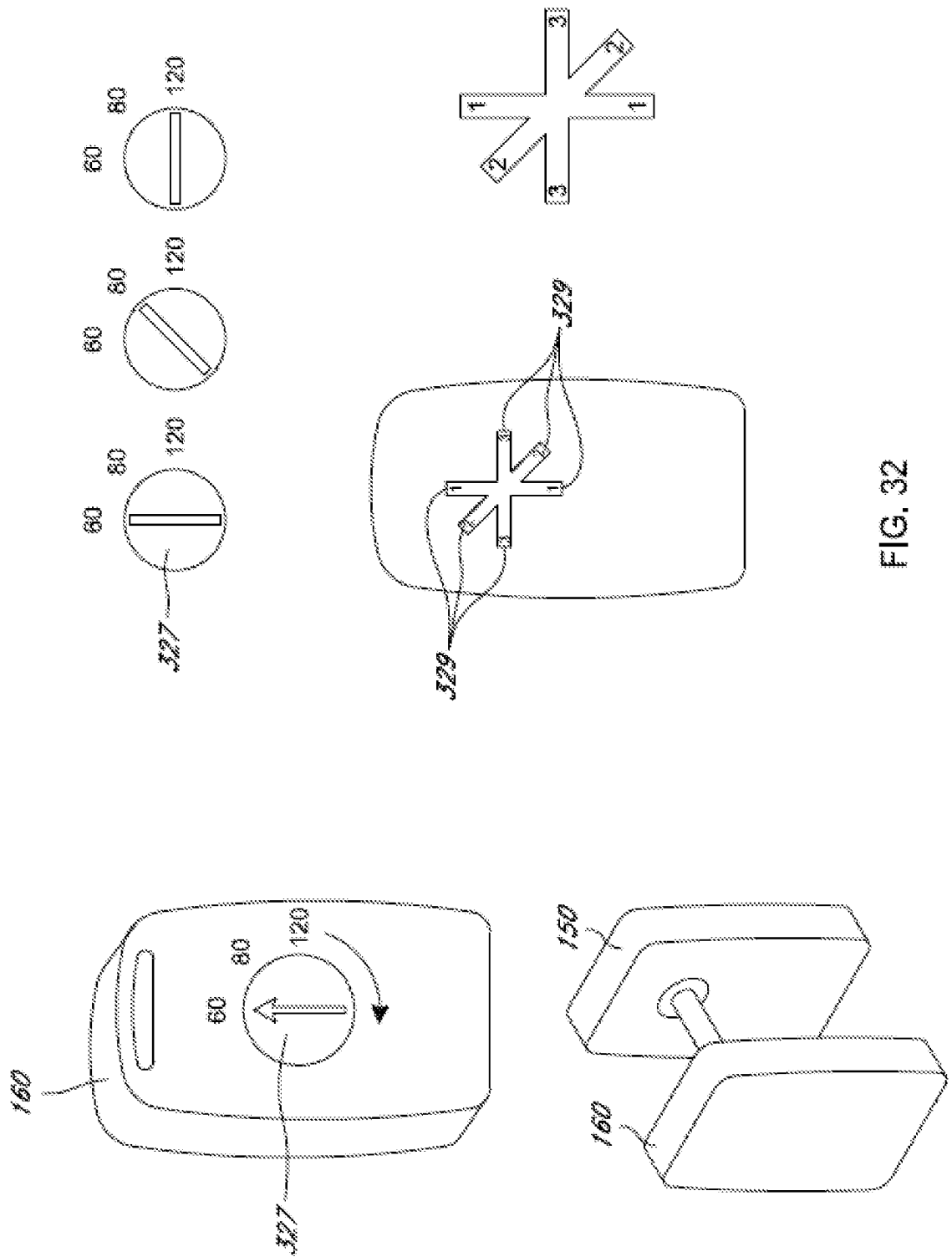
FIG. 32 illustrates a TNP system having a pressure-setting dial.

FIG. 32 illustrates that the canister 160 can include a dial 327 that allows pressure selection on the pump assembly 150. The dial 327 can be adapted to turn only with a special tool. The position of the dial indicates to the pump assembly 150 the setting by making a positive connection with switches 329. In some arrangements, the pressure setting cannot be changed without the canister 160 attached to the pump assembly 150, In some embodiments, the dial 327 is located on a side of the pump assembly. For example, the alarm indicator 116A shown in FIG. 4C can be replaced with a dial 327 configured to allow pressure selection on the pump assembly 150, as described above.

Figure 33:
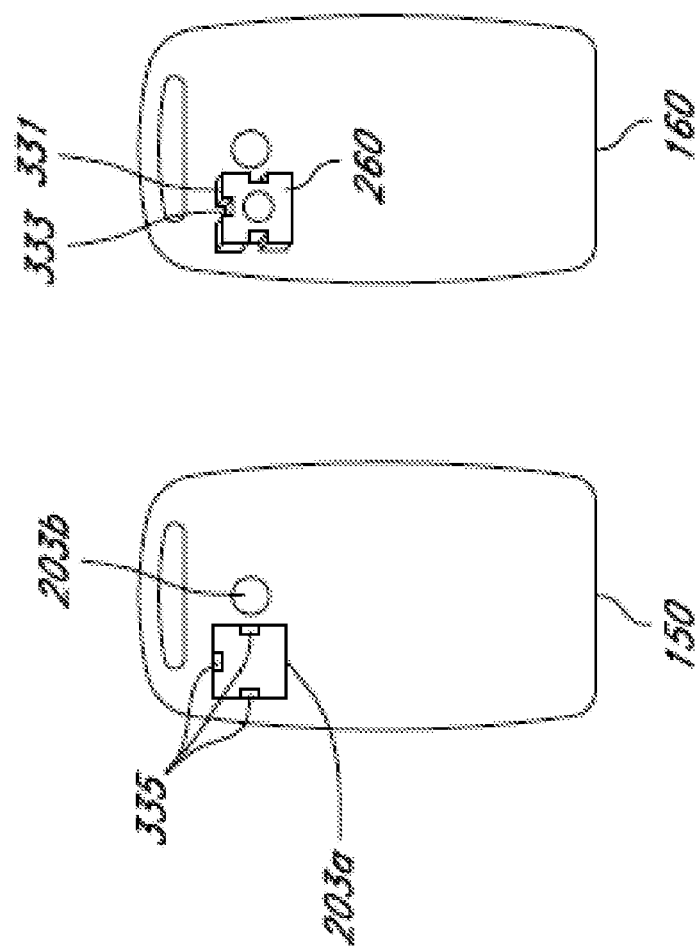
FIG. 33 illustrates a TNP system having two differently-shaped connector ports.

FIG. 33 illustrates that the pump assembly 150 can have a first connector port 203a that is differently shaped from a second connector port 203b thereby preventing misuse of attaching the incorrect connector 201 to the connector port 203. The first connector port 203a can be adapted to connect the pump assembly 150 to a canister connector 260. The second connector port 203b can be adapted to connect the pump assembly 150 to a canisterless connector 262. The canister connector 260 can include a knob 331 that allows a user to select the pressure setting for the pump assembly. The knob 331 can include contacts 333. The pump assembly 150 can have corresponding contacts 335 that are adapted to detect the position of the knob 331 by sensing the position of the contacts 333. The pump assembly 150 can adjust its pressure settings according to the position of the knob 331.

FIG. 34 illustrates that the pump assembly 150 can have a switch 337 attached to a battery cover 339 that signals whether a canister connector 260 or a canisterless connector 262 is connected to the pump assembly 150. In some arrangements, a battery pack 341 can be integrated with the canister 160. The pump assembly 150 can include a "cartridge" style battery door 343. The canister 160 can include a pneumatic coupling to remove user error of connecting the wrong dressing to the pump assembly 150. The battery door 343 can be adapted so that it cannot close on an invalid pressure setting.

Figure 35:
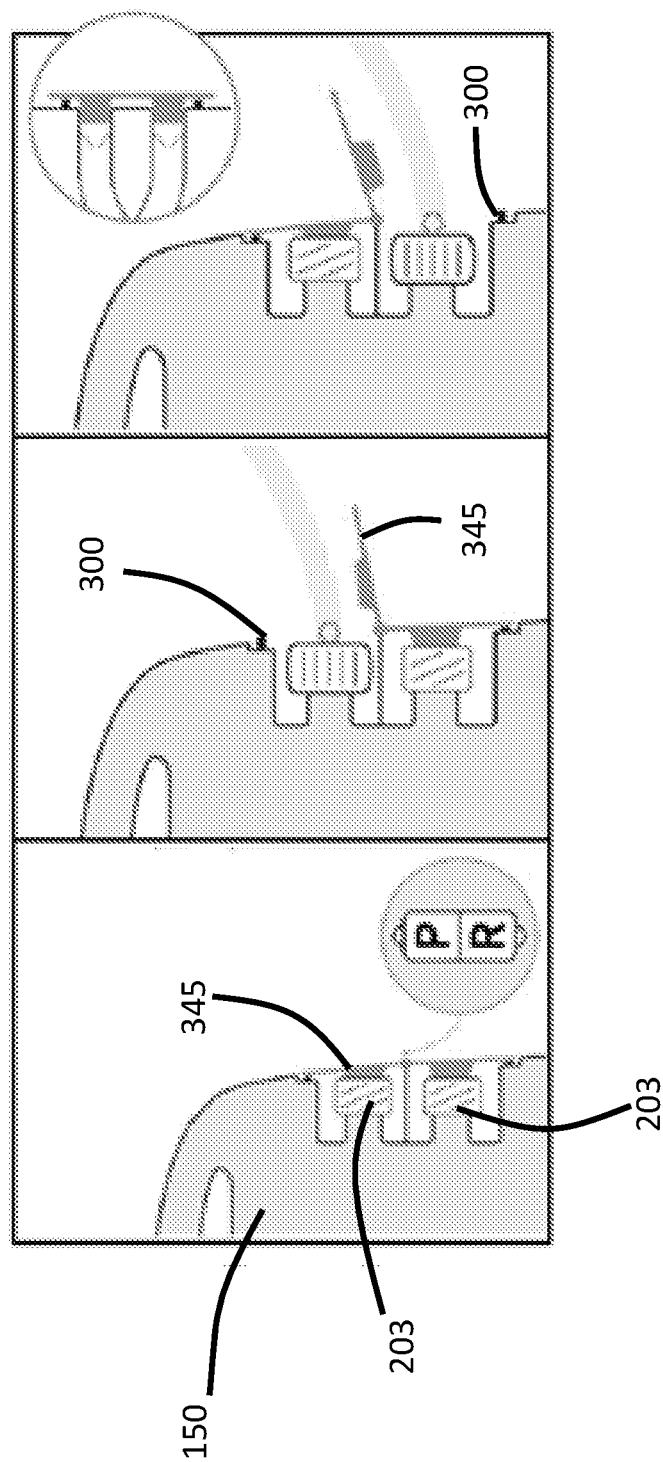
FIG. 35 illustrates a TNP system having two connector ports mounted on the pump assembly.

FIG. 35 illustrates that the pump assembly 150 can two connector ports 203 mounted on the side of the pump assembly 150. Each of the connector ports 203 can have its own clearly marked silicone flap 345. The connector ports 203 can branch to a common flow path. Each flap 345 hides a connector port 203. Each flap 345 depresses a controller switch 300 when closed to signal to the control board 206 which flap 345 is being used. The flap 345 can be made of silicone or other similar pliable material, thereby allowing the flap 345 to form an air-tight seal with the unused connector port 203.

FIG. 36 illustrates that the pump assembly 150 can include two connector ports 203 that connect to a manifold 347. The pump assembly 150 can include a pressure sensor 349 adapted to allow the pump assembly 150 to detect whether the connector 201 is securely attached to the connector port 203. The pump assembly 150 can include a switch 351 that opens and closes the manifold 347 to check whether the connector 201 has a fluid tight seal with the connector port 203.

Figure 37:
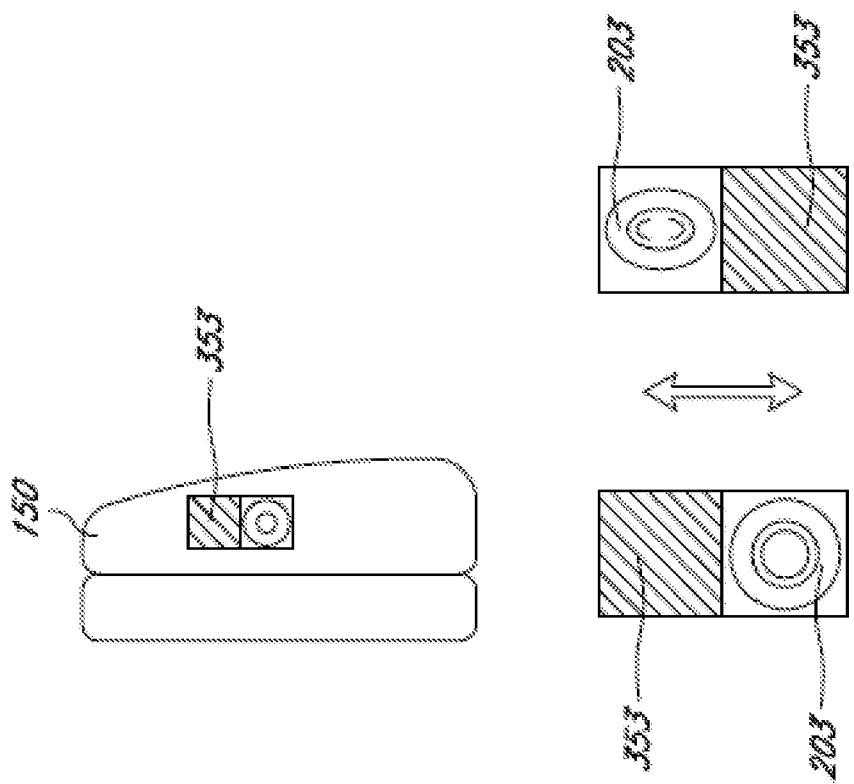
FIG. 37 illustrates a TNP system having two connector ports and a sliding cover that covers one or the other of the connector ports.

FIG. 37 illustrates that the pump assembly 150 can include two connector ports 203 and a sliding cover 353 that covers one or the other of the two connector ports 203. The sliding cover 353 can act as an electro-mechanical switch. The control board 206 of the pump assembly can detect the position of the sliding cover 353, allowing the pump assembly 150 to determine whether a canister connector 260 or canisterless connector is attached to the connector port 203. In some arrangements, the two connector ports 203 are differently shaped to avoid misuse of connecting the incorrect connector 201 to the connector port 203. In some embodiments, the two connector ports 201 are differently colored. The color of the connector port 203 can match the color of the connector 201 that is the correct connector 201 for connecting to the connector port 203.

FIG. 38 illustrates that the pump assembly 150 can include a user interface 240. The user interface 240 can include a button 241 that activates and deactivates therapy (such as a play/pause button) and one or more indicators. For example, the interface 240 can include a low battery indicator 242, a full canister indicator 244, a leak indicator 246, and a blockage indicator 248. In certain implementation, the full canister indicator 244 can be disabled and a full dressing indicator (not shown) can be enabled. Alternatively, in some embodiments, the indicator for canister full and dressing full can share the same indicator (e.g., light) and the indication changes depending on the mode of operation (e.g., light color changes to indicate canister full or dressing full).

Figure 39:
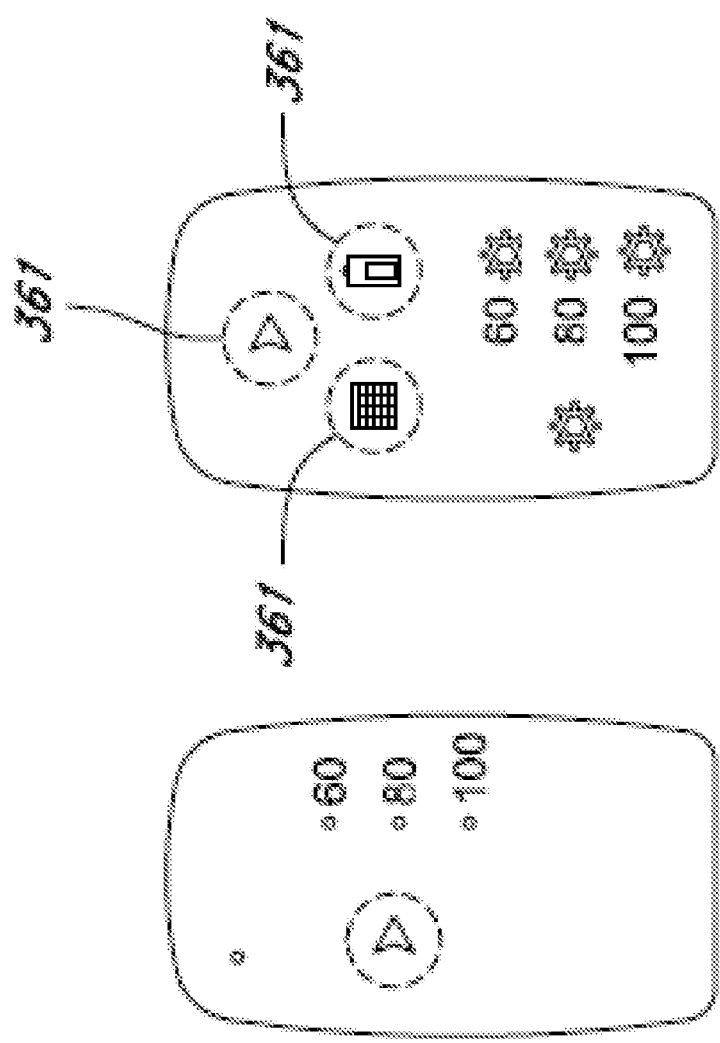
FIG. 39 illustrates embodiments of control buttons of the TNP system.

FIG. 39 illustrates that the pump assembly 150 can include one or more control buttons 361 that allow a user to modify the operation of the pump assembly 150. The buttons described here or elsewhere in the specification may be physical buttons, or may be virtual depictions of a button on a touchscreen interface. Two embodiments are depicted in FIG. 39 on the left and on the right. In the embodiment on the left, a single control button may be provided to start or pause operation of the pump assembly. In the embodiment on the right, multiple buttons may be provided to allow a user to start and stop operation of the device, and to set the level of negative pressure to be applied. For example, in a canister mode of operation, a user may be able to select between three negative pressure magnitudes of −60 mm Hg, −80 mm Hg, or −120 mm Hg. In some embodiments, certain buttons may be activated or usable in one mode of operation (for example in a canister mode of operation), but not be usable in another mode of operation (for example in a canisterless mode of operation). In some embodiments, the controls shown on the left and right side of FIG. 39 may be alternative screens of a touchscreen, with a first screen being utilized for a first mode of operation (e.g., a canisterless mode) and a second screen being utilized for a second mode of operation (e.g., a canister mode). In some embodiments, the control buttons can be adapted to allow a user to specify whether the pump assembly 150 is being used in canister or canisterless mode. In some arrangements, the control buttons can remove the need for the pump assembly 150 to have automatic detection capabilities.

Figure 40:
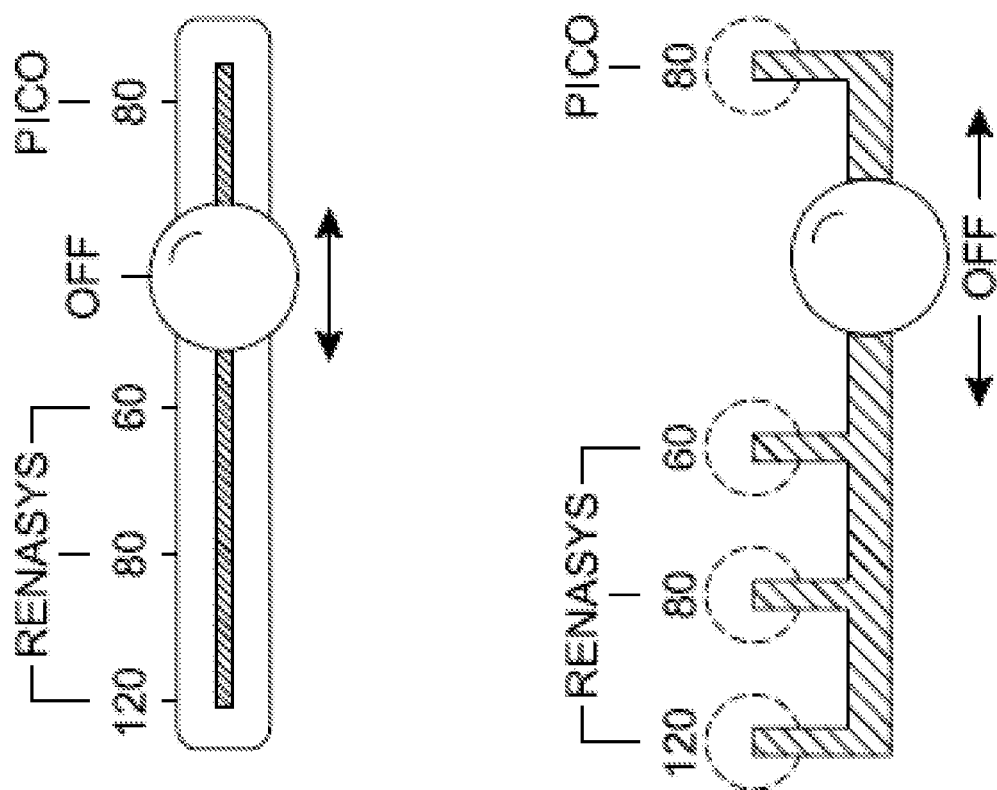
FIG. 40 illustrates an embodiment of a pressure-setting switch of the TNP system.

FIG. 40 illustrates that the pump assembly 150 can include a simple switch to choose the mode of operation of the pump assembly 150 at the same time as choosing the pressure.

Figure 41:
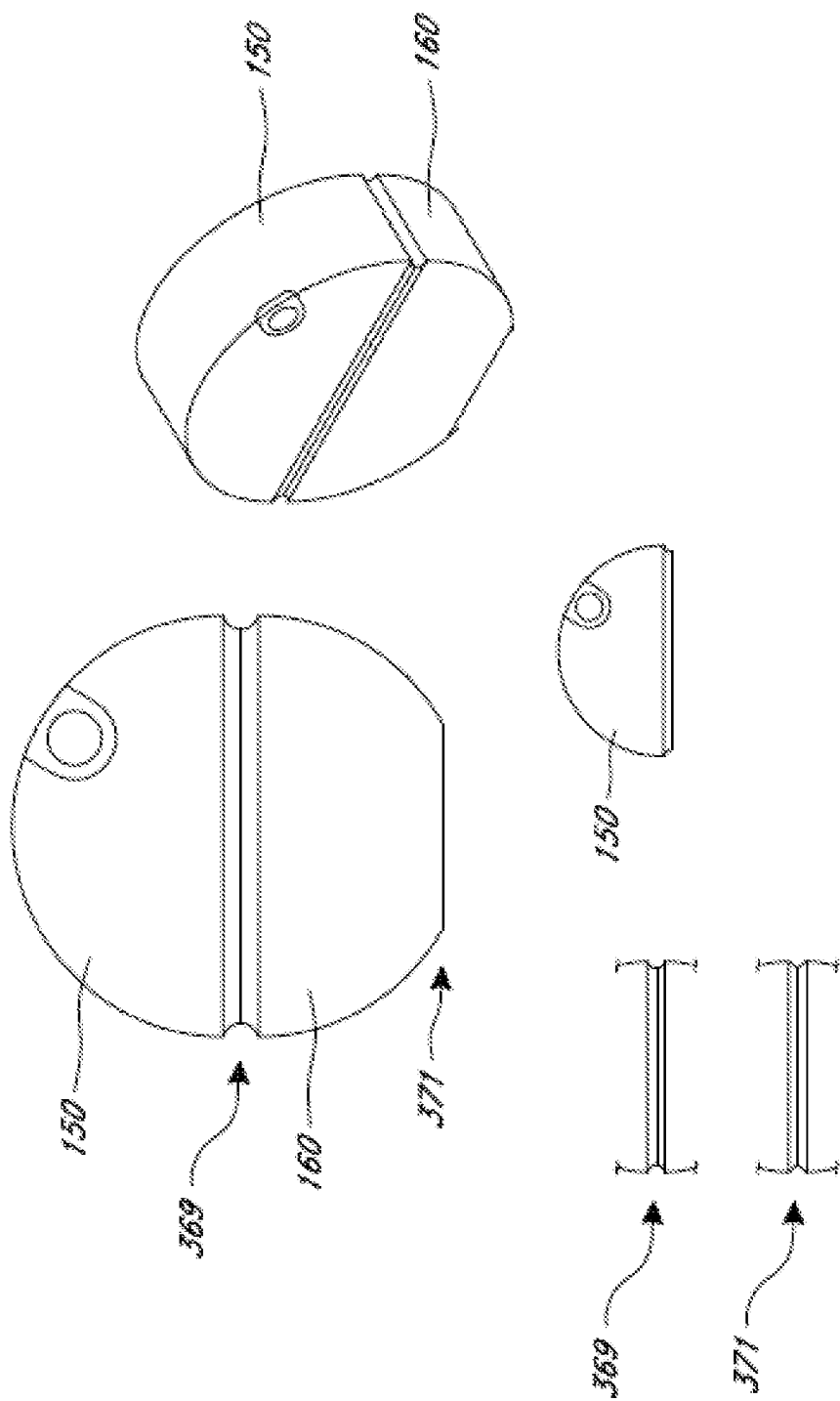
FIG. 41 illustrates an embodiment of a TNP system that has a disc-like shape when the pump assembly is connected to a canister.
Figure 42:
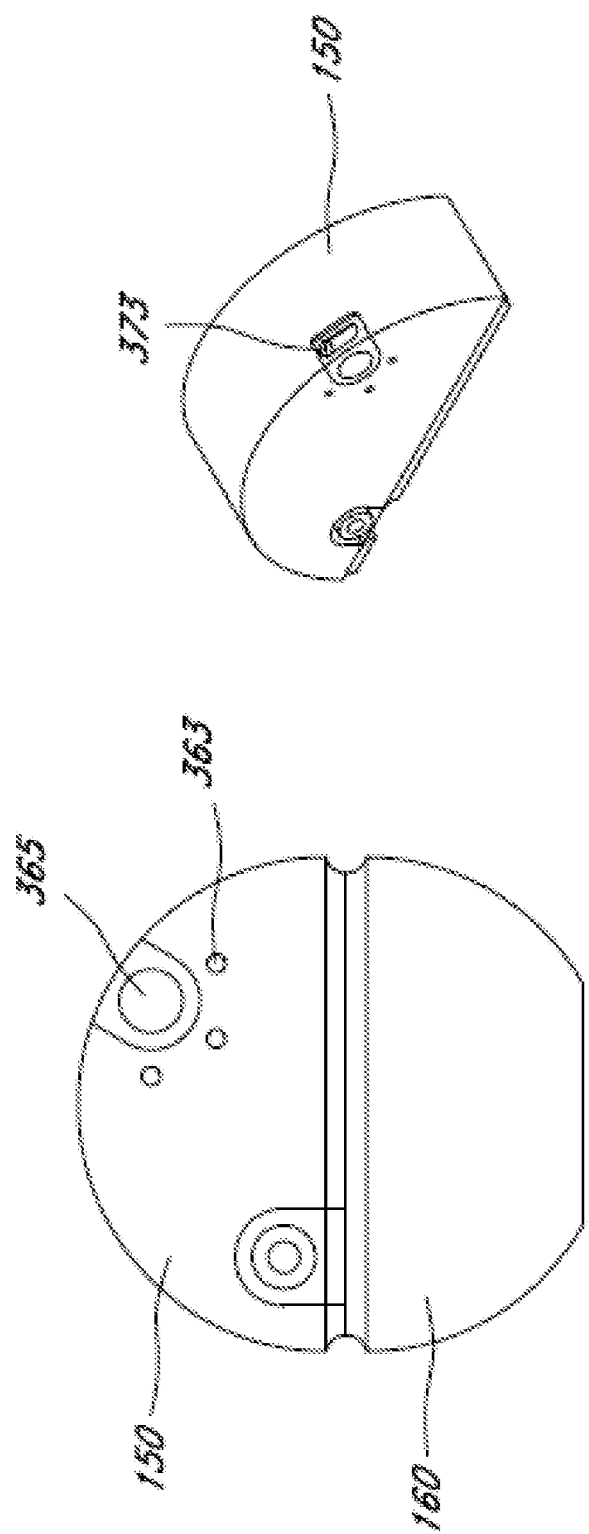
FIG. 42 illustrates another embodiment of a TNP system that has a disc-like shape when the pump assembly is connected to a canister.

FIGS. 41 and 42 illustrate different designs for that the pump assembly 150. The pump assembly 150 can form a disc-like structure when the pump assembly 150 is attached to the canister 160. The canister housing can have a bottom step 367. The pump assembly 150 and canister 160 can form a top step 369 when attached to one another. The pump assembly 150 can include back lit icons 363. The canister 160 can be made of a clear material. The pump assembly 150 can include a large alarm light 365. The pump assembly 150 can have a slide on/off switch 373.

FIG. 43 illustrates that the canister connector 260 can be adapted to increase the size of the bore between the pump assembly 150 and the canister 160 to reduce the peak pressure. The canisterless connector 262 can have a small bore allowing the peak pressure to remain unchanged. The difference peak pressure as a result of this difference in bore size can provide the pump assembly 150 greater differentiation between the two modes of operation.

Figure 44:
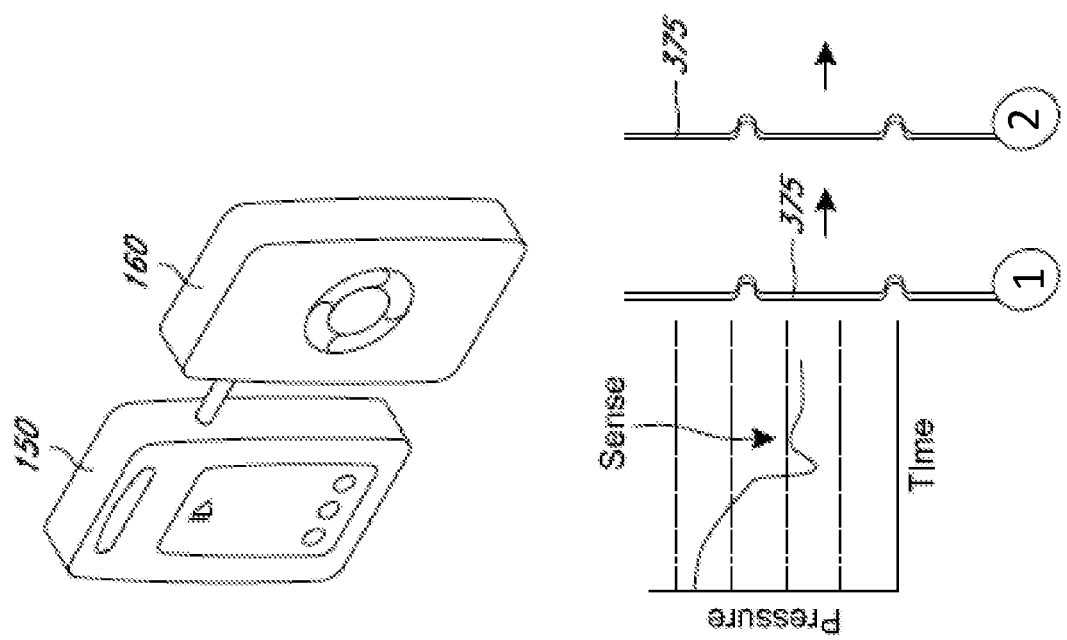
FIG. 44 illustrates an embodiment of a TNP system having a canister with a flexible membrane.

FIG. 44 illustrates that the canister 160 can include a flexible membrane 375. The membrane 375 can be adapted to deflect when the pressure drops. The pump assembly 150 can be adapted to detect movement of the membrane 375 when the pressure drops.

Figure 45:
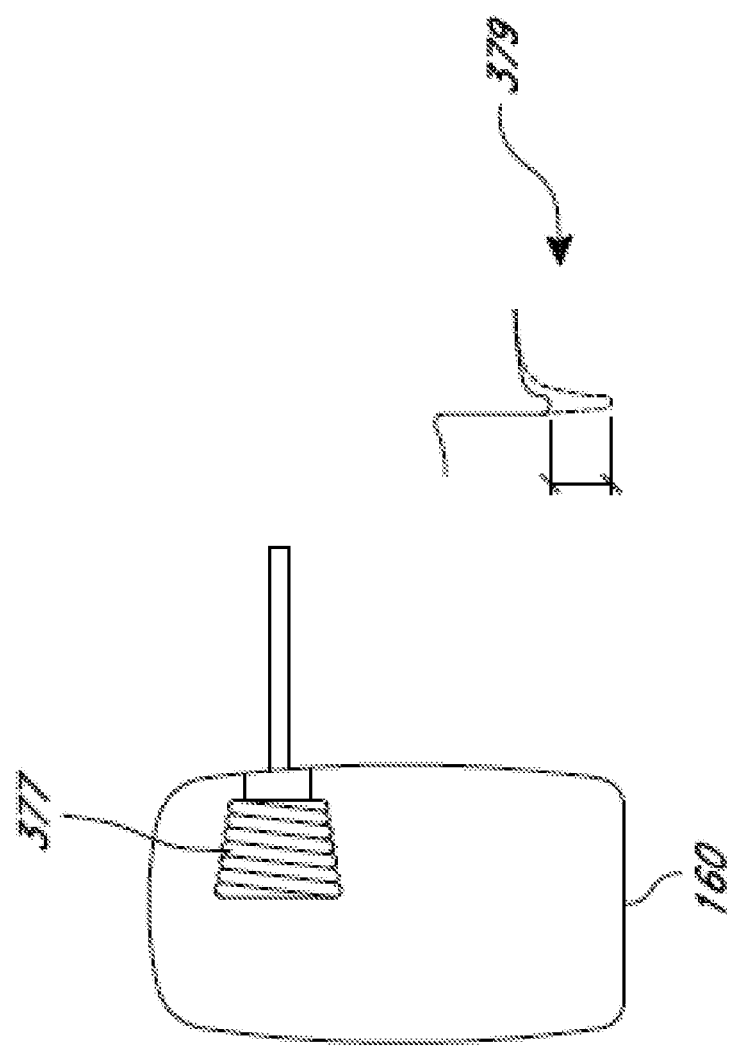
FIG. 45 illustrates an embodiment of a TNP system having a flexible bellows.

FIG. 45 illustrates that the canister 160 can include a flexible bellows 377 that magnifies the pressure overshoot signal 379 for the canister 160. The bellows 379 can be arranged so that work is needed to collapse the bellows.

Figure 46:
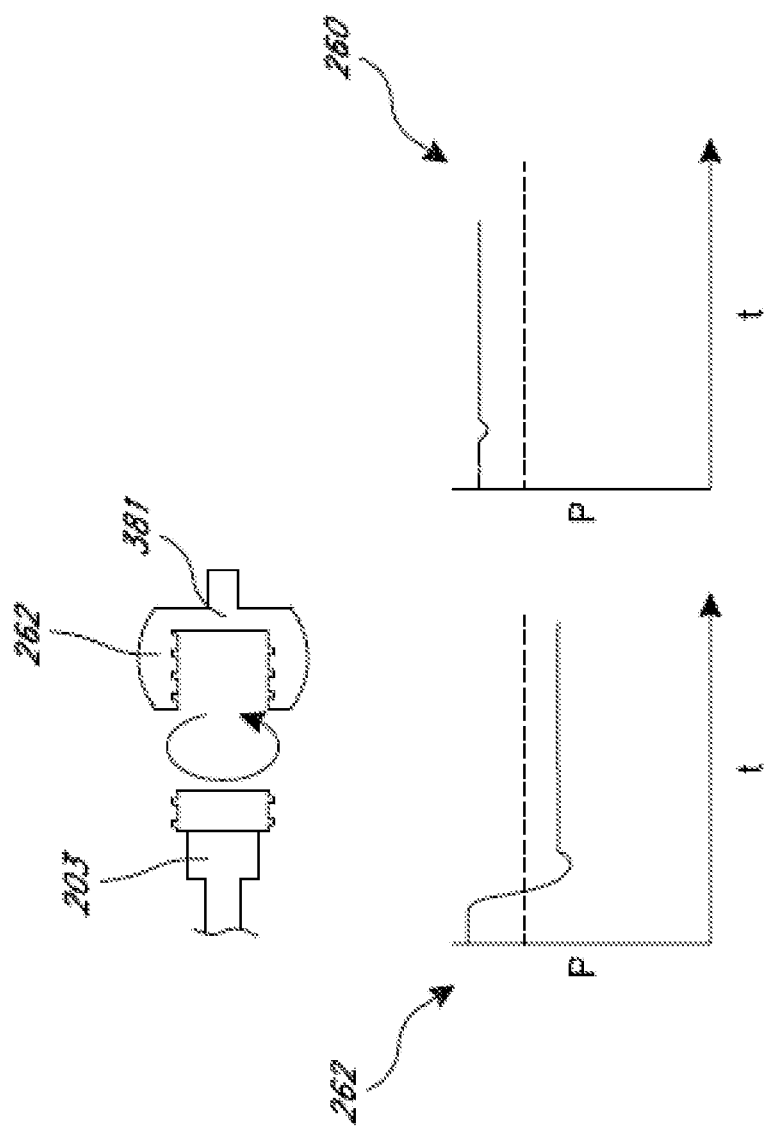
FIG. 46 illustrates an embodiment of a connector that includes a check valve.

FIG. 46 illustrates that the canisterless connector 262 can include a check valve 381 with a set cracking pressure (e.g., −40 mmHg). The pump assembly 150 can be activated for a fraction of a second (e.g., 100 ms pulse) in the canisterless mode of operation. The check valve 381 will not crack and the pump assembly can measure depressurization. When the canister connector 260 is connected to the pump assembly 150, the unrestricted path will elicit no pressure change in response to the pulse of pressure from the pump assembly 150.

Figure 47:
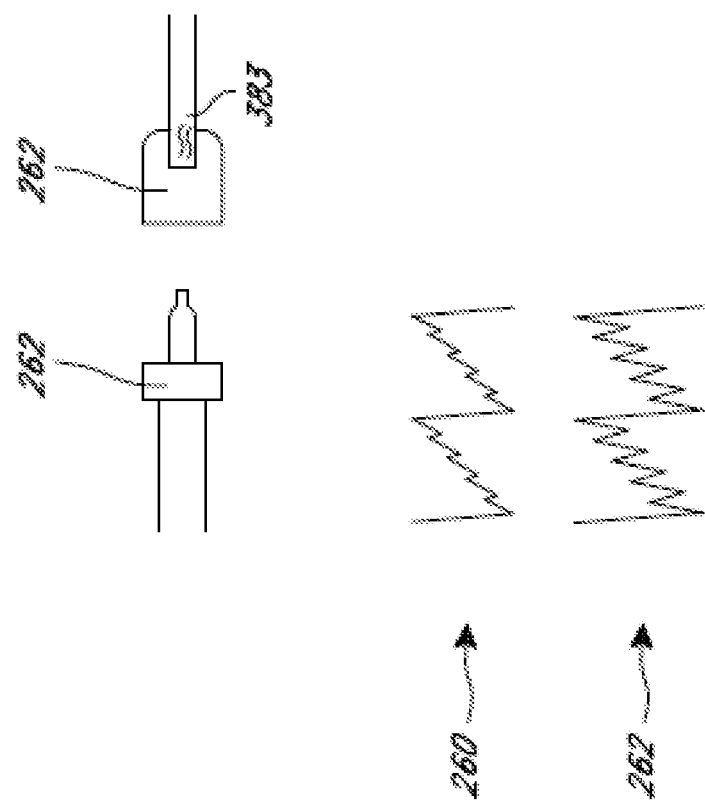
FIG. 47 illustrates an embodiment of a connector that includes a mechanical flap.

FIG. 47 illustrates that the canisterless connector 262 can include a flap 383 and the canister connector 260 can not include the flap 383. The flap 383 can be adapted to create a different pressure signal (e.g., mechanical vibration) for the canisterless connector 262 compared to the signal for the canister connector 260 that does not include a flap 383. The mechanical vibration of the flap 383 can create a pressure vibration that can be detected by the pump assembly 150. In some embodiments, the connector 201 can include a structure that produces a sound when air passes through the connector 201. The pump assembly 150 can include a pressure sensor that can detect the noise made by the connector 201. For example, the canister connector 260 can be arranged to produce a "kazoo" type of sound while the canisterless connector 262 produces a "whistle" type sound. The pressure sensor 209 of the pump assembly 150 can be adapted to distinguish between the "kazoo" type of sound of the canister connector 260 and the "whistle" type sound of the canisterless connector 262.

Figure 48:
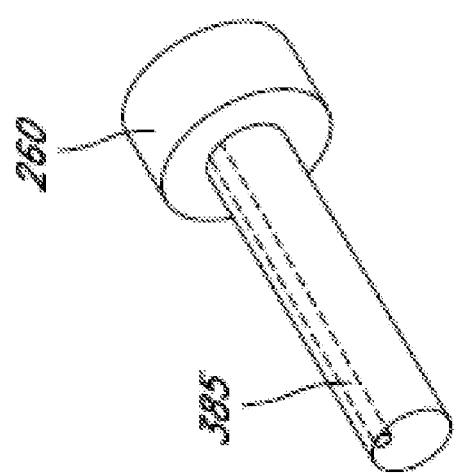
FIG. 48 illustrates an embodiment of a connector that includes a dual lumen tubing.

FIG. 48 illustrates that the canister connector 260 can include a dual lumen tubing 385 that allows the pump assembly 150 to identify the canister 160 by a pressure change or mechanical confirmation.

As described herein, various detectors can be used to detect presence of a canister according to some embodiments. Detectors can include one or more of proximity detectors (such as, capacitive, photoelectric, inductive, or the like), optical detectors, electromagnetic detectors (such as a reed detector, Hall effect detector, magnetic detector, or the like), radio frequency identification (RFID) detectors, bar code detectors, QR code detectors, or the like.

Figure 49:
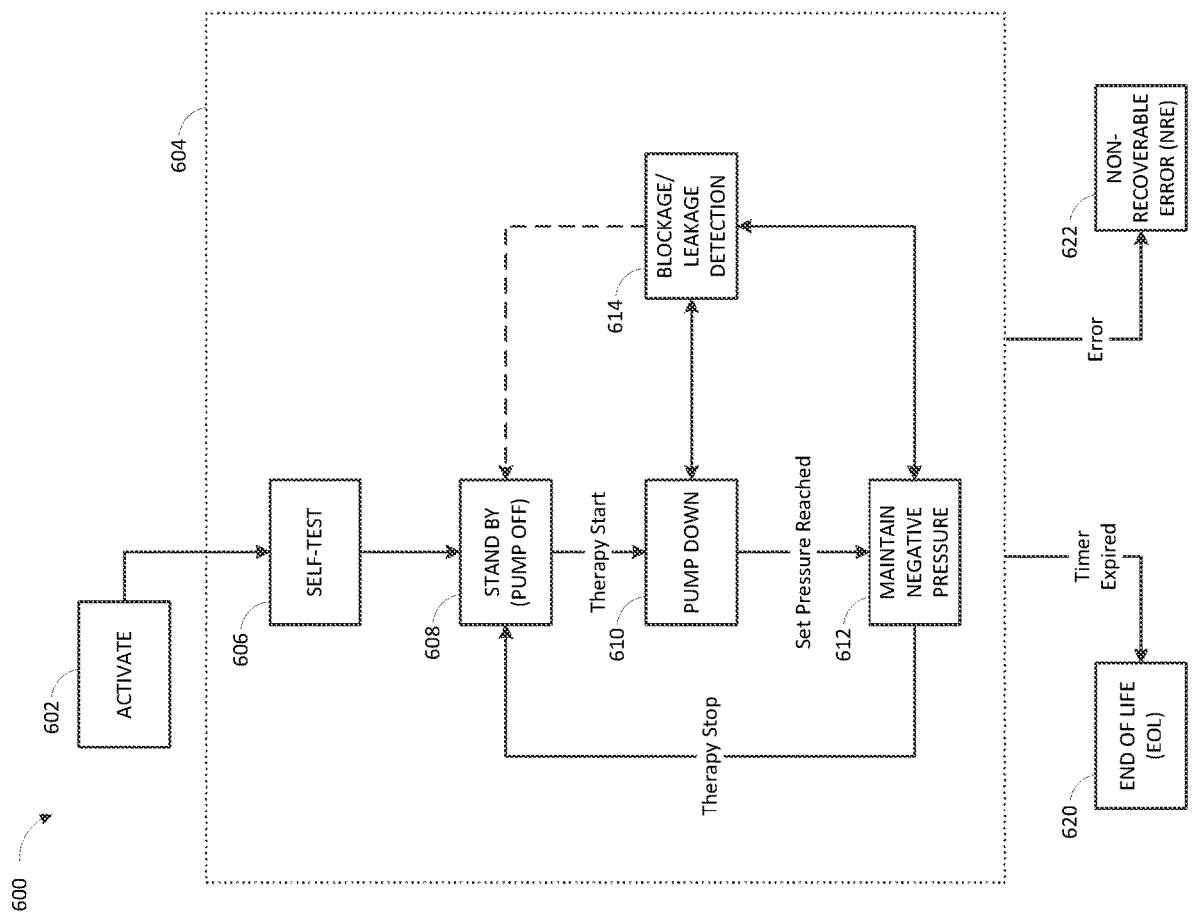
FIG. 49 illustrates an operational state diagram of a TNP system according to some embodiments.

FIG. 49 illustrates an operational state diagram 600 of a TNP system according to some embodiments. The state diagram 600 can be implemented by the control board 206 of the apparatus 150. For example, the state diagram 600 can be executed by a controller. The state diagram 600 includes an activate state 602, an operational state 604 (in which negative pressure wound therapy is being provided), end of life (EOL) state 620, and a non-recoverable error (NRE) state 622.

The state diagram 600 can enter the active state 602 when the TNP system has been activate by a user. Activation can, for example, include applying power to the system in the field for the first time (such as, by turning the system on). In some embodiments, the TNP system can be configured to operate over a particular lifetime (such as 7 days, 10 days, 20 days, 30 days, or the like) from initial activation and discontinue operation after the duration of time has passed. The TNP system can track a duration of time since the initial activation and transition to the EOL state 620 when the tracked duration of time reaches the lifetime duration. Provision of negative pressure wound therapy may not allowed in once the EOL state 620 has been reached.

After activation in state 602, the state diagram 600 can transition to state 606 where one or more tests are performed to determine that the TNP system is operating as intended. For example, in state 606 one or more of the following tests can be performed: memory test, controller watchdog test, I/O test, user interface test, pressure sensor test, or the like. Pressure sensor test can be performed utilizing an electric circuit that includes a resistor positioned in series with the pressure sensor and a feedback circuit that senses at least one of current or voltage across the resistor and detects if there is a pressure sensor malfunction (such as a short circuit, open circuit, or the like). In some implementations, the resistor can be positioned in parallel with the pressure sensor, more than one resistor or another circuit element can be utilized, and the like. If the one or more tests fails, the state diagram 600 can transition to the NRE state 622, in which provision of negative pressure wound therapy may not be allowed.

If the TN system passes the one or more tests in state 606, the state diagram 600 can transition to a stand-by state 608, in which it can wait for activation of negative pressure wound therapy. Such activation can be performed by a user (for example, by pressing a button 202) or automatically upon expiration of a period of time. The negative pressure source may not be active in the stand-by state 608.

The state diagram can transition to a pump down state 610 upon activation of negative pressure wound therapy in state

608. In state 610, the TNP system can activate the negative pressure source to provide or achieve a particular target level of negative pressure at the wound (for example, under the wound dressing). As the TNP system can be configured to operate with a canister or without the canister (refer to FIG. 50), provision of negative pressure wound therapy can be performed according to canister and canisterless modes, in which one or more operating parameters may be different. In some embodiments, the target level of negative pressure provided by the negative pressure source to the wound can be adjustable or selectable when the TNP system operates in canister mode. In canisterless mode, the target level of negative pressure may be set to a particular value and may not be adjustable.

In some implementations, the controller can operate the negative pressure source differently depending on canister or canisterless mode of operation. For example, in canister mode of operation, the negative pressure source can be operated continuously based on feedback from a pressure sensor that measures pressure in the fluid flow path (which can directly or indirectly indicate pressure at the wound). The negative pressure source can be operated using pulse width modulation (PWM) control, proportional integral derivative (PID) control, or another suitable control mechanism in order to minimize the error between the target level of negative pressure and actual negative pressure at the wound. This type of continuous control based on the feedback pressure measurement can be effective particularly when a controlled air leak is introduced in the fluid flow path (for example, through a dressing port).

In certain implementations, canisterless mode of operation can involve controlling the negative pressure source to be activated while the target level of negative pressure is being established at the wound and, subsequently, be deactivated. When, due to one or more leaks, negative pressure at the wound falls below the target level of negative pressure (for example, below an threshold level in relation to the target level of negative pressure), the negative pressure source can be re-activated to re-establish the target level of negative pressure at the wound. In canisterless mode, the negative pressure source may not be operated continuously.

When the target level of negative pressure at the wound has been reached, the state diagram 600 can transition from the pump down state 610 to a maintenance state 612, in which the target level of negative pressure is maintained. As explained above, maintenance can be performed differently depending on whether the TNP system is operating in canister or canisterless mode. The state diagram can remain in the maintenance state 612 until therapy is stopped (for example, by the user pressing the button to pause therapy), in which case a transition to the stand-by state 608 can be made.

In some embodiments, while negative pressure wound therapy is being provided, the state diagram 600 can perform at least one of a blockage or leakage detection in state 614. For example, state 614 can be periodically executed while the negative pressure source is active. Blockage detection can involve monitoring at least one of the pressure at the wound or activity level of the negative pressure source (for example, as indicated by a duty cycle of an actuator of the negative pressure source). Blockage can be detected when the pressure at the wound is below the target level of negative pressure and the activity level satisfies a threshold associated with a blockage in the fluid flow path. Blockage detection can be performed differently in canister or canisterless modes of operation. For example, different activity level thresholds can be used in canister and canisterless modes. As another example, blockage detection can be suspended in one of the modes.

In some implementations, leakage detection can involve monitoring at least one of the pressure at the wound or activity level of the negative pressure source (for example, the duty cycle). Leakage can be detected when the pressure at the wound is below the target level of negative pressure and the activity level satisfied a threshold associated with a leak in the fluid flow path. Leakage detection can be performed differently in canister or canisterless modes of operation. For example, leakage can be detected in canisterless mode when the duty cycle of the negative pressure source satisfies a leakage threshold (such as, 20%, 30%, and the like) over a duration of time (such as 5 minutes, 7 minutes, 10 minutes, and the like). In canister mode, leakage can be detected when a target negative pressure has not been reached over a duration of time (such as 5 minutes, 7 minutes, 10 minutes, and the like). As another example, blockage detection can be suspended in one of the modes.

In certain implementations, at least one of blockage or leakage detection can be performed differently depending on whether the state diagram 600 is in the pump down state 610 or maintenance state 612. For example, the duration of time for detecting a leak can be shorter in the pump down state 610 than in the maintenance state 612. This difference can be due to a greater concern with one or more leaks present in the dressing seal (for example, due to incorrect placement of the dressing over the wound) preventing the target level of negative pressure from being reached during initial pump down than during maintenance of the target negative pressure at the wound.

In some embodiments, the TNP system can provide one or more indications associated with reaching one or more of states or performing one or more transitions in the state diagram 600. As disclosed herein, the one or more indications can be visual, audible, tactile, and the like. In some cases, indication can alternatively or additionally involve deactivating the source of negative pressure. For example, the negative pressure source can be deactivated when at least one of a blockage or leakage has been detected.

Figure 50:
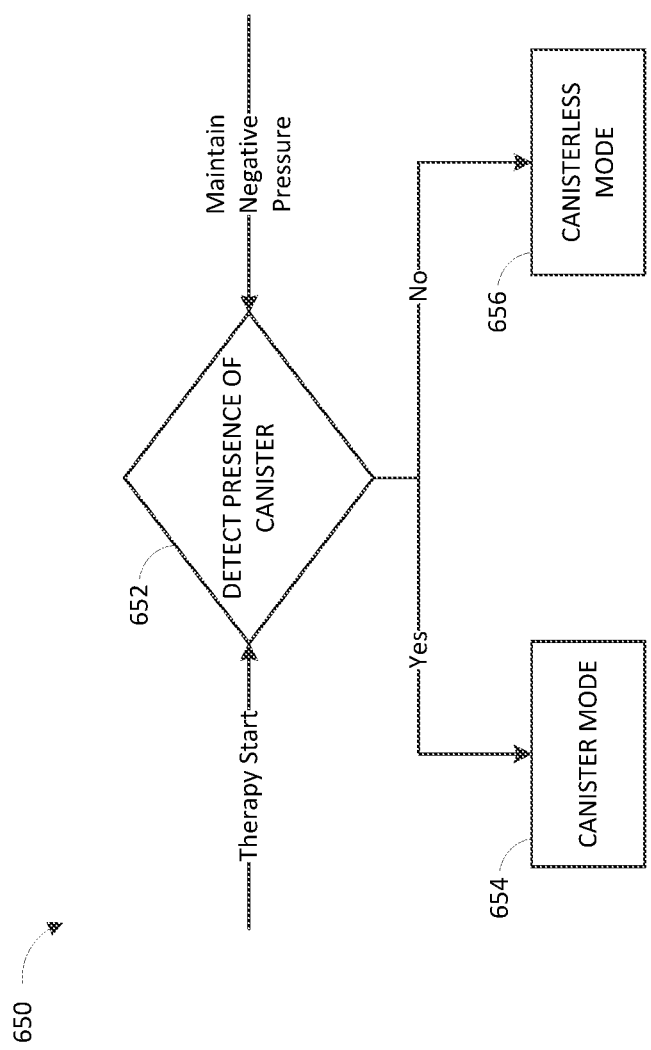
FIG. 50 illustrates a process of operation of a TNP system according to some embodiments.

FIG. 50 illustrates a process 650 of operation of a TNP system according to some embodiments. The process 650 can be implemented by the control board 206 of the apparatus 150. For example, the process 650 can be executed by a controller. The process 650 starts in state 652 in which presence of a canister in the fluid flow path is detected. Detection can be performed using any of the approaches and detectors described herein. State 652 can be executed when therapy is started (transition from the stand-by state 608 to the pump down state 610 in FIG. 51) or when the target level of negative pressure at the wound is being maintained (in state 612 in FIG. 51). In some embodiments, the TNP system can be switched from canister to canisterless mode or vice versa while negative pressure therapy is being provided (for example, while the negative pressure source is active) without interrupting therapy. For instance, while negative pressure therapy is being provided, a canister can be removed or attached, and the TNP system can be configured to detect this change without deactivating the negative pressure source. In certain implementations, negative pressure wound therapy can be interrupted when the TNP system is switched from canister to canisterless mode or vice versa.

In state 652, if the canister is detected, the process 650 transitions to state 654 in which the TNP system operates in the canister mode as described herein. If the canister is not detected, the process 650 transitions to state 656 in which the TNP system operates in the canisterless mode as described herein.

Figure 51A:
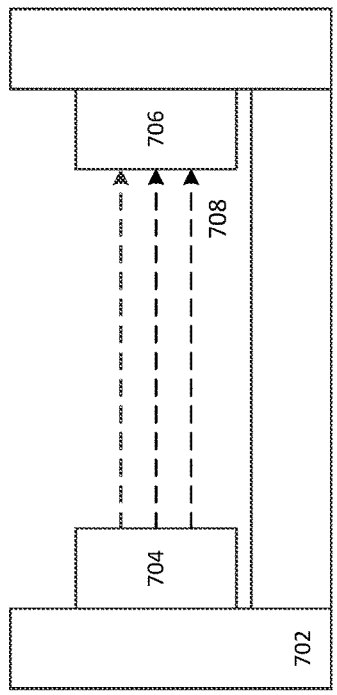
FIGS. 51A-C illustrate optical detection according to some embodiments.
Figure 51B:
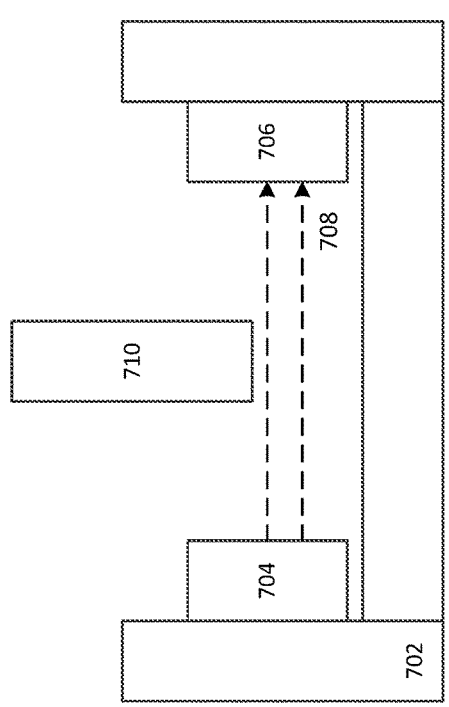
Figure 51C:
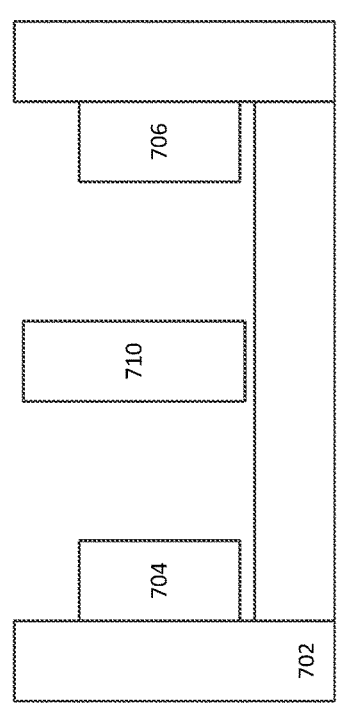

FIGS. 51A-C illustrate optical detection according to some embodiments. As is illustrated, an optical detector can include an emitter 704 (such as an LED) that emits light 708 and a detector 706 (such as a photodiode, phototransistor, or the like) that detects emitted light 708. In some implementations, a reflective detector can be used in which the emitter and detector are co-located. In some embodiments, the optical detector can be positioned in a recess 702 of the housing of a pump assembly. A canister can include a protrusion 710 (such as the fin 170A) that is inserted and fits into the recess 702 when the canister is being positioned in the fluid flow path. As is illustrated in FIGS. 51B-C respectively, the protrusion 710 can partially or substantially fully block the emitted light 708, which can be detected by the detector 706. Incorrect (FIG. 51B) and correct positioning (for example, insertion) of the canister (FIG. 51C) can be detected by the optical detector.

In some implementations, a detector can alternatively or additionally detect one or more indicators positioned on the canister. For example, canister housing and/or tube can include one or more of a color pattern, a shape, a bar code pattern, label, or the like that can be detected by the detector. The indicator can be used to encode information corresponding to one or more parameters of the canister, such as canister size, for use in provision of negative pressure wound therapy. In addition, detection of the indicators can provide information regarding correct positioning of the canister. For example, a bar code detector can count the number of bars of a canister bar code to determine that the canister is correctly positioned.

In certain embodiments, a canister can have one or more magnets embedded in the housing and/or the tube. The pump assembly can include a magnetic field detector (such as a reed switch, Hall effect sensor, or the like) that detects magnetic field of the one or more magnet when the canister is being positioned in the fluid flow path. The magnet can be a spherical magnet (having a substantially uniform radial magnetic field, which may be detected more reliably) or a magnet of any other suitable shape and strength. Proper positioning of the canister can be detected based on the detected strength of the magnetic field.

Figure 52:
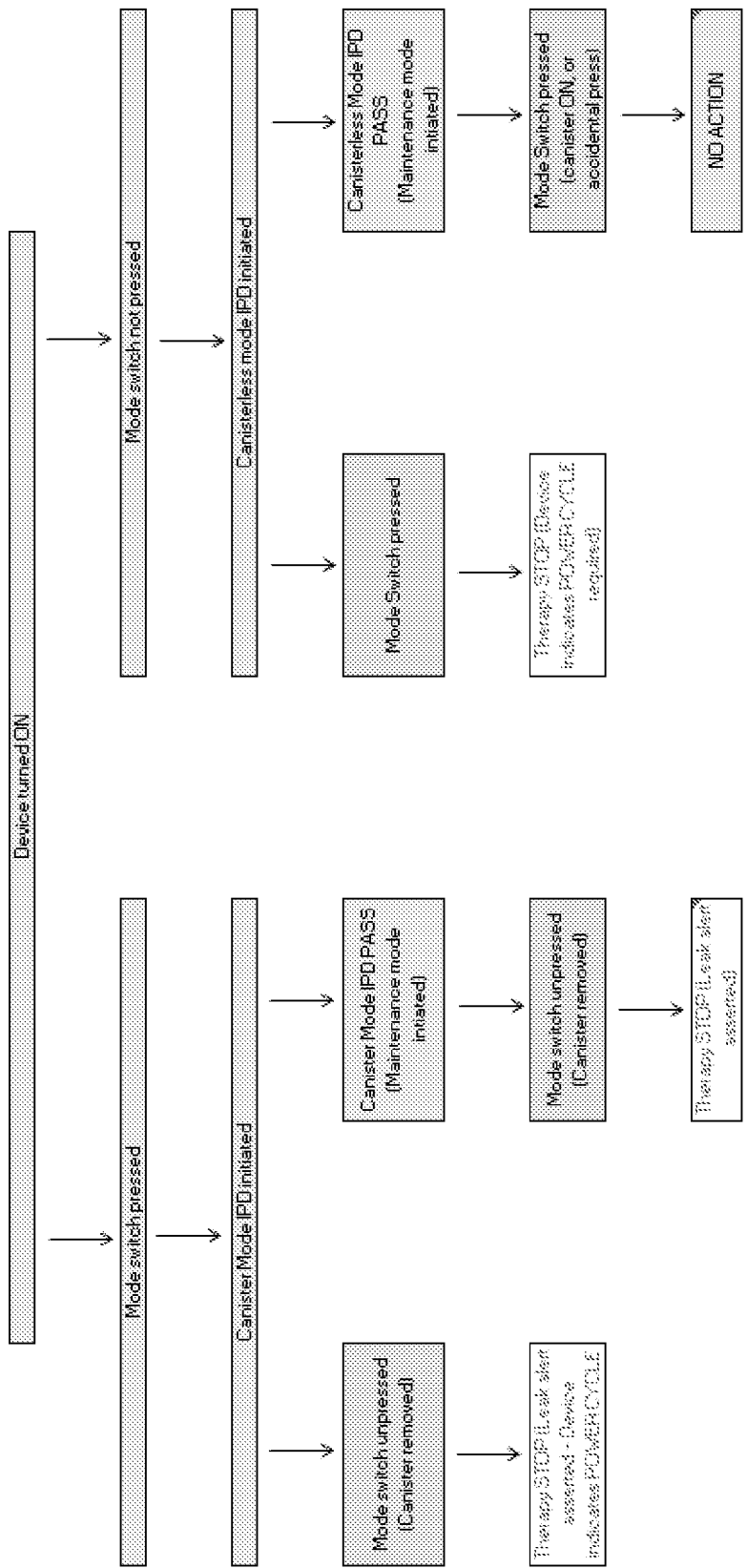
FIG. 52 illustrates a logic path set according to some embodiments.

FIG. 52 shows a logic path set of a TNP system according to some embodiments. The logic path set in one embodiment can prevent the TNP system from operating at an undesired negative pressure. In certain arrangements, the TNP system can allow a user to adjust a parameter (e.g., magnitude) of the applied negative pressure. The TNP system may allow a user to adjust the parameter in one operational mode (e.g., canister mode) and not allow a user to adjust the parameter in another operational mode (e.g., canisterless mode). For example, when a canister is connected in the flow path (e.g., canister or RENASYS™ mode), the TNP system may allow a user to select from a set of possible negative pressure magnitudes (e.g., −60 mmHg, −80 mmHg, −120 mmHg). When a canisterless dressing is connected to the TNP system (e.g., canisterless or PICO™ mode), in some embodiments the TNP system may be configured to operate at only one magnitude of negative pressure (e.g., −80 mmHg), and not provide for user selectability. Further details regarding how negative pressure may be activated and selected for canister and canisterless modes are described elsewhere in this specification, including with respect to FIGS. 38 and 39 below. The TNP system may further include a power or on/off switch that may be operated by a user, and in some embodiments as described further below, the TNP system may be configured to require that the user power off and on the device after the occurrence of certain events in order for particular features of the system to be operational.

With continued reference to FIG. 52, the logic path set can be arranged to prevent the TNP system from operating in canisterless mode at a pressure other than a preset negative pressure value (e.g., −80 mmHg). The TNP system can include a mode switch (e.g., switch 158A, shown in FIG. 7B) that indicates whether the pump assembly 150 is to operate in canister mode or canisterless mode. In the illustrated embodiment, the default mode of operation is the canisterless mode, in that the TNP system operates in canisterless mode when the mode switch is not pressed or activated. The system can include a therapy button that signals to the TNP system to begin applying negative pressure to the wound, such as described with respect to FIGS. 38 and 39 below. Once the device is powered on and the therapy button is pressed, the device can perform an initial pump down (IPD) to determine whether a fluidic seal is established between the pump assembly 150 and the wound. The IPD parameters can differ depending on the operational mode of the TNP system. For example, the TNP system can have an IPD pass condition when the system is operating in canister mode that is different from an IPD pass condition when the system is operating in canisterless mode. If the TNP system is able to meet the IPD pass condition for the selected mode of operation, the system can initiate maintenance mode. The system can apply a selected negative pressure to the wound in the maintenance mode. If the TNP system is not able to meet the IPD pass condition for the selected mode, the system can stop operation of the pump assembly and signal a leak alert.

The logic path set can be arranged to interrupt operation of the TNP system when the state of the mode switch is changed during the IPD. For example, referring to the right side of the logic path set shown in FIG. 52, once the device is powered on and the therapy button is pressed without a canister connector detected (e.g., the mode switch is not pressed), the TNP system begins the IPD for canisterless mode. If the system detects that the mode switch has been pressed before the maintenance mode has begun, the TNP system can flash an alert and depower the pump. The alert can indicate that a power cycle is required. After the pump has been deactivated, it is necessary to turn off the device and then turn back on the device in order to restore power to the pump.

This alert and depowering of the pump, and subsequent requirement of turning the pump off and on again, may be advantageous in an embodiment where for a canisterless mode of operation, only a single preset negative pressure value is desired or mandated for treatment. For example, this can prevent a user from starting to use the device in canisterless mode, and then pressing the mode switch which would allow the user to select a negative pressure other than the preset value (e.g., −80 mmHg).

As indicated in the far right path of the logic path set shown in FIG. 52, once the maintenance mode has been initiated for the canisterless mode, the mode switch can be deactivated so that pressing the switch after this time has no effect on operation of the TNP system. This again can be advantageous to ensure that in the canisterless mode of operation, only the single preset negative pressure value is utilized. In some embodiments, for a user to be able to utilize the device in a canister mode thereafter, the device needs to be powered off and back on.

Referring to the left-hand side of logic flow path of FIG. 52, the system can be configured so that when the TNP system is operating in canister mode, a detection of the mode switch becoming unpressed during initial pump down and before maintenance mode is initiated may cause a leak alarm to alert and may cause the pump to deactivate. This then requires that the device go through a power cycle (off then on) in order to be able to operate the pump. This can prevent a user from choosing a pressure to be used in a canister mode of operation (e.g., −120 mmHg), and then removing the canister and attaching a canisterless dressing to the system to operate at a negative pressure (e.g., −120 mm Hg) that is different from the negative pressure value desired or mandated for a canisterless mode of operation (e.g., −80 mm Hg).

If in canister mode the device passes the initial pump down and enters maintenance mode, a subsequent unpressing of the switch while the pump is operating may trigger a leak alarm which would deactivate operation of the pump. In some embodiments, the device is powered off and on again before it can be operated again. In some configurations, the TNP system can be arranged so that if the system is operating in canister mode, and a therapy button is pressed to pause or stop therapy, and then the canister is removed, the TNP system can thereafter operate in canisterless mode (e.g., at −80 mmHg) and does not require power cycling.

All of the features disclosed in this specification (including any accompanying exhibits, claims, abstract and drawings), and/or all of the steps of any method or process so disclosed, may be combined in any combination, except combinations where at least some of such features and/or steps are mutually exclusive. The disclosure is not restricted to the details of any foregoing embodiments. The disclosure extends to any novel one, or any novel combination, of the features disclosed in this specification (including any accompanying claims, abstract and drawings), or to any novel one, or any novel combination, of the steps of any method or process so disclosed.

Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Likewise the term "and/or" in reference to a list of two or more items, covers all of the following interpretations of the word: any one of the items in the list, all of the items in the list, and any combination of the items in the list. Further, the term "each," as used herein, in addition to having its ordinary meaning, can mean any subset of a set of elements to which the term "each" is applied. Additionally, the words "herein," "above," "below," and words of similar import, when used in this application, refer to this application as a whole and not to any particular portions of this application.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein. Certain embodiments of the disclosure are encompassed in the claim set listed below or presented in the future.

What is claimed is:

1. A negative pressure wound therapy apparatus comprising:
a negative pressure source configured to provide, via a fluid flow path, negative pressure to a wound covered by a wound dressing;
a connector port in fluid communication with an inlet of the negative pressure source and configured to be fluidically connected to either (i) a canister configured to store fluid aspirated from the wound or (ii) the wound dressing without a canister between the connector port and the wound dressing;
a plurality of switches disposed at the connector port; and
a controller configured to:
based on a signal received from at least one switch of the plurality of switches, determine that the canister is positioned in the fluid flow path; and
adjust one or more operational parameters of negative pressure wound therapy based on the determination.

2. The apparatus of claim 1, wherein the at least one switch is disposed within a recess of the connector port.

3. The apparatus of claim 1, wherein the plurality of switches comprises at least one electrical switch.

4. The apparatus of claim 1, wherein the controller is further configured to determine that the canister is positioned in the fluid flow path in response to the at least one switch of the plurality of switches being activated.

5. The apparatus of claim 1, wherein the controller is further configured to determine that the canister is positioned in the fluid flow path in response to each of the plurality of switches being activated.

6. The apparatus of claim 1, wherein the at least one switch is configured to be activated when the canister is positioned in the fluid flow path, the at least one switch further configured to be not activated when the wound dressing without a canister is positioned in the fluid flow path.

7. The apparatus of claim 1, wherein the plurality of switches comprises first and second switches positioned on opposite walls of a recess of the connector port.

8. The apparatus of claim 1, wherein the at least one switch comprises a radial switch or a rotational switch.

9. The apparatus of claim 1, wherein the at least one switch is configured to detect a change of a magnetic field generated by a magnet of the canister.

10. The apparatus of claim 1, wherein the plurality of switches comprises at least one a capacitive sensor, an inductive sensor, an infrared sensor, an ultrasonic sensor, an optical sensor, or a photodetector.

11. The apparatus of claim 1, wherein:
the one or more operational parameters of negative pressure wound therapy comprise mode of operation of the negative pressure source;
responsive to a determination that the canister is positioned in the fluid flow path, the negative pressure source is activated continuously; and
responsive to a determination that the canister is not positioned in the fluid flow path, the negative pressure source is activated intermittently.

12. The apparatus of claim 1, wherein:
the one or more operational parameters of negative pressure wound therapy comprise leak detection;
responsive to a determination that the canister is positioned in the fluid flow path, leak detection is performed based on monitoring a time duration for establishing a target negative pressure level in the fluid flow path; and
responsive to a determination that the canister is not positioned in the fluid flow path, leak detection is performed based on monitoring a duty cycle of the negative pressure source.

13. The apparatus of claim 1, wherein:
the one or more operational parameters of negative pressure wound therapy comprise blockage detection;
responsive to a determination that the canister is positioned in the fluid flow path, blockage detection is performed using a first threshold; and
responsive to a determination that the canister is not positioned in the fluid flow path, blockage detection is performed using a second threshold different from the first threshold.

* * * * *

UNITED STATES PATENT AND TRADEMARK OFFICE
CERTIFICATE OF CORRECTION

| | | |
|---|---|---|
| PATENT NO. | : 11,395,870 B2 | Page 1 of 2 |
| APPLICATION NO. | : 16/486131 | |
| DATED | : July 26, 2022 | |
| INVENTOR(S) | : Ben Alan Askem et al. | |

It is certified that error appears in the above-identified patent and that said Letters Patent is hereby corrected as shown below:

In the Specification

Column 11, Line 17, delete "4A," and insert -- 4A. --.

Column 11, Line 49, delete "assembly," and insert -- assembly. --.

Column 12, Line 50, delete "reader" and insert -- reader. --.

Column 13, Line 36, delete "tubing," and insert -- tubing. --.

Column 13, Line 54, delete "2993" and insert -- 29.93 --.

Column 15, Line 7, delete "206," and insert -- 206. --.

Column 15, Line 17, delete "can by" and insert -- can be --.

Column 15, Line 43, delete "cansterless" and insert -- canisterless --.

Column 17, Line 36, delete "fill" and insert -- full --.

Column 19, Line 51, delete "157," and insert -- 157. --.

Column 21, Line 36, delete "4(C" and insert -- 4C --.

Column 21, Line 46, delete "10A" and insert -- 100A --.

Column 25, Line 43, delete "10A" and insert -- 100A --.

Column 26, Line 27, delete "150A" and insert -- 150A. --.

Signed and Sealed this
Seventeenth Day of December, 2024

Derrick Brent
*Acting Director of the United States Patent and Trademark Office*

CERTIFICATE OF CORRECTION (continued)
U.S. Pat. No. 11,395,870 B2

Column 26, Line 32, delete "150A" and insert -- 150A. --.

Column 27, Line 63, delete "203F," and insert -- 203F. --.

Column 30, Line 1, delete "10" and insert -- 1° --.

Column 30, Line 50, delete "153G" and insert -- 153G. --.

Column 31, Line 21, delete "2250." and insert -- 225G. --.

Column 31, Line 23, delete "2270" and insert -- 227G --.

Column 31, Line 27, delete "2250." and insert -- 225G. --.

Column 33, Line 3, delete "262," and insert -- 262. --.

Column 34, Line 16, delete "260," and insert -- 260. --.

Column 34, Line 43, delete "16B," and insert -- 16B. --.

Column 36, Line 35, delete "203," and insert -- 203. --.

Column 36, Line 44, delete "203," and insert -- 203. --.

Column 37, Line 56, delete "4" and insert -- 1/4 --.

Column 37, Line 67, delete "300," and insert -- 300. --.

Column 39, Line 27, delete "port," and insert -- port. --.

Column 39, Line 40, delete "150," and insert -- 150. --.

Column 42, Line 59, delete "TN" and insert -- TNP --.